(12) United States Patent
Regnier et al.

(10) Patent No.: US 12,208,133 B2
(45) Date of Patent: Jan. 28, 2025

(54) ENGINEERING THE RRM2 SUBUNIT OF RIBONUCLEOTIDE REDUCTASE TO RESIST DEGRADATION

(71) Applicant: UNIVERSITY OF WASHINGTON, Seattle, WA (US)

(72) Inventors: Michael Regnier, Seattle, WA (US); Charles E. Murry, Seattle, WA (US); Xuan Guan, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 1120 days.

(21) Appl. No.: 16/457,441

(22) Filed: Jun. 28, 2019

(65) Prior Publication Data

US 2020/0000886 A1    Jan. 2, 2020

Related U.S. Application Data

(60) Provisional application No. 62/692,217, filed on Jun. 29, 2018.

(51) Int. Cl.
| | | |
|---|---|---|
| *A61K 38/44* | (2006.01) | |
| *A61K 48/00* | (2006.01) | |
| *C12N 15/52* | (2006.01) | |
| *C12N 15/86* | (2006.01) | |

(52) U.S. Cl.
CPC .......... *A61K 38/44* (2013.01); *A61K 48/0066* (2013.01); *C12N 15/52* (2013.01); *C12N 15/86* (2013.01); *C12Y 117/04001* (2013.01)

(58) Field of Classification Search
None
See application file for complete search history.

(56) References Cited

U.S. PATENT DOCUMENTS

| | | | | |
|---|---|---|---|---|
| 6,682,917 | B1 * | 1/2004 | Nakamura ........... | C12N 9/0093 |
| | | | | 424/94.4 |
| 10,046,010 | B2 * | 8/2018 | Gothelf .............. | C12N 5/0662 |
| 11,078,247 | B2 * | 8/2021 | Fotin-Mleczek .... | C12N 15/113 |
| 2010/0021713 | A1 | 1/2010 | Lane et al. | |
| 2010/0166714 | A1 | 7/2010 | Chien et al. | |
| 2011/0003327 | A1 | 1/2011 | Chien et al. | |
| 2011/0033430 | A1 | 2/2011 | Chien et al. | |

FOREIGN PATENT DOCUMENTS

| | | |
|---|---|---|
| WO | 2008/054819 A2 | 5/2008 |
| WO | 2010/042856 A2 | 4/2010 |
| WO | 2010/144678 A2 | 12/2010 |

OTHER PUBLICATIONS

Manohar et al. (J. Biol. Chem., vol. 298 (2), 2022, pp. 1-18).*
Chimploy et al., "Mouse Ribonucleotide Reductase Control: Influence of Substrate Binding Upon Interactions with Allosteric Effectors", J of Biol. Chem 276(10): 7093-7100 (2001).
Gallo et al., "A lentiviral vector with a short troponin-I promoter for tracking cardiomyocyte differentiation of human embryonic stem cells", Gene Therapy 15:161-170 (2008).
Griscelli et al., "Expression from cardiomyocyte-specific promoter after adenovirus-mediated gene transfer in vitro and in vivo", C R Acad Sci III. 320(2):103-12 (1997).
Guo et al., "Targeted Deletion of the A3 Adenosine Receptor Confers Resistance to Myocardial Ischemic Injury and does not Prevent Early Preconditioning." Journal of molecular and cellular cardiology 33(4): 825-830 (2001).
Headrick et al., "Acute adenosinergic cardioprotection in ischemic-reperfused hearts." American Journal of Physiology—Heart and Circulatory Physiology 285(5): H1797-H1818 (2003).
Hendricks et al., "Allosteric Regulation of Vaccinia Virus Ribonucleotide Reductase, Analyzed by Simultaneous Monitoring of Its Four Activities", J of Biol. Chem. 273(45): 29512-29518 (1998).
Hendricks et al., "Regulation of T4 Phage Aerobic Ribonucleotide Reductase: Simultaneous Assay of the Four Activities", J of Biol. Chem. 272(5): 2861-2865 (1997).
Kolwicz et al., "AAV6-mediated cardiac-specific overexpression of ribonucleotide reductase enhances myocardial contractility", Mol. Ther. 24(2):240-250 (2016).
Korte et al., "Upregulation of cardiomyocyte ribonucleotide reductase increases intracellular 2 deoxy-ATP, contractility, and relaxation", J Mol Cell Cardiol. 51(6):894-901 (2011).
Murray "Abstract 369: Engineering Rrm2 to Elevate 2-deoxy-ATP and Improve Cardiomyocyte Function", Circulation Research 121:A369 (2017).
Nicholas et al., "Alternative promoters and cardiac muscle cell-specific expression of the Na+/Ca2+ exchanger gene." American Journal of Physiology—Heart and Circulatory Physiology 274(1): H217-H232 (1998).
Radivojac et al. "Identification, analysis, and prediction of protein ubiquitination sites", Proteins 78(2): 365-380 (2010).
Yang et al., "Cardiac overexpression of A1-adenosine receptor protects intact mice against myocardial infarction", American Journal of Physiology—Heart and Circulatory Physiology 282(3): H949-H955 (2002).

* cited by examiner

*Primary Examiner* — Hope A Robinson
(74) *Attorney, Agent, or Firm* — Nixon Peabody LLP; Mark J. FitzGerald; Jeanne Jodoin

(57) ABSTRACT

Provided herein are isolated nucleic acids that encode a stable form of Rrm2 for the use of increasing the intracellular Rrm2 protein levels and cytosolic 2-deoxy-ATP (dATP) levels. Further provided herein are methods for treating a cardiac disease or disorder, e.g., myocardial infarction or myocardial ischemia, by administering the isolated nucleic acids, a polypeptide encoded by the isolated nucleic acids, or composition comprising the isolated nucleic acids to a subject in need thereof.

10 Claims, 10 Drawing Sheets
Specification includes a Sequence Listing.

Fig. 8

ENGINEERING THE RRM2 SUBUNIT OF RIBONUCLEOTIDE REDUCTASE TO RESIST DEGRADATION

CROSS REFERENCE TO RELATED APPLICATION

This application is a 35 U.S.C. § 111 (a) Utility Application which claims benefit under 35 U.S.C. § 119 (e) of U.S. Provisional Application No. 62/692,217, filed on Jun. 29, 2018, the content of which is incorporated herein by reference in its entirety.

GOVERNMENT SUPPORT

This invention was made with government support under grant numbers IR01HL128368, HL094374, and HL111197 awarded by the National Institutes of Health. The Government has certain rights in the invention.

SEQUENCE LISTING

The instant application contains a Sequence Listing which has been filed electronically in ASCII format and is hereby incorporated by reference in its entirety. Said ASCII copy, created on Jul. 16, 2019, is named 034186-095510USPT-_SL.txt and is 54,317 bytes in size.

TECHNICAL FIELD

The technology described herein relates to methods of increasing ribonucleotide reductase activity and deoxynucleotide levels in a cell.

BACKGROUND

Overexpression of ribonucleotide reductase (RNR) in cardiomyocytes increases the amount of cytosolic 2-deoxy-ATP (dATP), which can be used by myosin and significantly increases the performance of normal, damaged, and diseased heart muscle. While cardiomyocyte-specific overexpression of the Rrm1 subunit of RNR is stable, the Rrm2 subunit is expressed with high variability in multiple disease models. Described herein are compositions and methods of increasing ribonucleotide reductase activity and deoxynucleotide levels in a cell.

SUMMARY

The present technology is based, in part, on the finding that virally-mediated overexpression of the RNR complex elevated dATP and increased the rate and magnitude of contraction and increased left ventricular contraction in normal hearts as well as rodent models of myocardial infarction and dilated cardiomyopathy. However, the variability in Rrm2 subunit expression between particular cardiac diseases and disease models can attenuate the efficacy of simply overexpressing the RNR subunits Rrm1 and/or Rrm2 to elevate dATP levels. Given the variability for the expression of the Rrm2 subunit, it was hypothesized that Rrm2 is regulated via degradation. Pharmacological inhibition of proteasome activity led to increased expression of Rrm2 in virally-transduced cardiomyocytes in vitro. Mutant Rrm2 proteins modified to interfere with proteasome-mediated degradation are described herein. It is demonstrated herein that introducing these mutants to human induced pluripotent stem cell (IPS)-derived cardiomyocytes resulted in higher levels of Rrm2 than those overexpressing wild-type protein and resulted in higher levels of cytosolic dATP as measured by Liquid chromatography-mass spectrometry. Described herein are improved Rrm2 polypeptides that are resistant to degradation through the ubiquitin-proteasome pathway, thereby permitting more stable and consistent RNR enzyme activity and increased deoxynucleotide levels in cardiomyocytes transduced in vivo. Vectors encoding the improved Rrm2 polypeptides, alone or together with sequence encoding Rrm1, are described herein, as well as methods of increasing intracellular dATP using such vectors and methods of treating disease, e.g., cardiac disease, using the polypeptides or vectors encoding them.

Accordingly, one aspect of the technology provided herein is an isolated nucleic acid molecule encoding an Rrm2 polypeptide that, together with Rrm1 polypeptide comprises ribonucleotide reductase activity, the encoded Rrm2 polypeptide comprising a mutation that increases the intracellular level of the polypeptide as compared to wild-type Rrm2 polypeptide.

In one embodiment of any aspect, the mutation increases the intracellular stability of the Rrm2 polypeptide relative to wild-type. For example, stability can be increased at least 10%, at least 20%, at least 30%, at least 40%, at least 50%, at least 60%, at least 70%, at 80%, at least 90%, at least 95%, at least 99% or more as compared to wild-type Rrm2.

In one embodiment, the Rrm2 polypeptide comprises two mutations relative to wild-type Rrm2 polypeptide. In another embodiment, the Rrm2 polypeptide comprises three, four, five, six, seven, eight, nine or to mutations relative to wild-type Rrm2 polypeptide. In another embodiment, the Rrm2 polypeptide comprises ten or fewer mutations, nine or fewer mutations, eight or fewer mutations, seven or fewer mutations, six or fewer mutations, five or fewer mutations, four or fewer mutations, three or fewer mutations, or two or fewer mutations. In one embodiment of any aspect, the wild-type Rrm2 gene sequence is SEQ ID NOs: 3 or 5, and the wild-type Rrm2 polypeptide sequence is SEQ ID NO: 4.

In one embodiment of any aspect, the mutation is in a ubiquitin-binding degron. In one embodiment of any aspect, the mutation in the ubiquitin-binding degron prevents or inhibits ubiquitin-mediated degradation of the Rrm2 gene product.

In one embodiment of any aspect, the ubiquitin-binding degron is at amino acids 30, 31, 32, 33, 49, 50, and/or 51 of SEQ ID NO: 4 or encoded at nucleotides 88-96, 97-99, and/or 145-153 of SEQ ID NO: 3 or SEQ ID NO: 5.

In one embodiment of any aspect, the mutation comprises an amino acid substitution, deletion, or insertion, or a combination of these.

In one embodiment of any aspect, the Rrm2 gene sequence encodes an Rrm2 polypeptide having 2 to 10 amino acid changes as compared to a Rrm2 polypeptide encoded by a wild-type Rrm2 gene.

In one embodiment of any aspect, the mutation is a mutation of an amino acid selected from the group consisting of: 30, 31, 32, 33, 49, 50, and/or 51 positions. In one embodiment of any aspect, the mutation is a mutation of a nucleic acid selected from the group consisting of: 88, 89, 90, 91, 92, 93, 94, 95, 96, 97, 98, 99, 145, 146, 147, 148, 149, 150, 151, 152, and/or 153.

In one embodiment of any aspect, the mutated amino acid sequence is selected from SEQ ID NOs: 21-25. In one embodiment of any aspect, the mutated nucleic acid sequence is selected from SEQ ID NOs: 16-20.

In one embodiment of any aspect, the mutation increases the level of cytosolic 2-deoxy-ATP (dATP) in a cell when the isolated nucleic acid molecule is expressed in a cell as compared to expression of wild-type Rrm2. For example, the level is increased at least 50%, at least 60%, at least 70%, at 80%, at least 90%, at least 95%, at least 99% or more as compared to wild-type Rrm2.

In one embodiment of any aspect, operably linked to a sequence that permits expression of the encoded polypeptide in a cell.

In one embodiment of any aspect, the sequence that permits expression of the encoded polypeptide in a cell comprises a promoter. Exemplary promotes include a constitutive promoter, a ubiquitous promoter, an inducible promoter, a viral promoter, a tissue specific promoter, and a synthetic promoter. In one embodiment of any aspect, the tissue specific promoter is a cardiac tissue specific promoter.

Another aspect of the technology described herein provides a vector comprising any of the isolated nucleic acid molecules described herein.

In one embodiment of any aspect, the vector is a viral vector. Exemplary viral vectors include an adeno associated virus (AAV), a lentivirus (LV), a herpes simplex virus (HSV), an adeno virus (AV), or a pox virus (PV) vector.

In one embodiment of any aspect, the vector is a DNA or RNA virus.

Another aspect of the technology described herein provides a polypeptide encoded by any of the isolated nucleic acid molecules described herein.

In one embodiment of any aspect, the polypeptide sequence is selected from SEQ ID NO: 4, 16-20.

Another aspect of the technology described herein provides a protein complex comprising any of the mutant Rrm2 polypeptides described herein and at least one polypeptide of a different sequence.

In one embodiment, the complex comprises an Rrm1 polypeptide.

Another aspect of the technology described herein provides a composition comprising any of the isolated nucleic acid molecules described herein, any of the vectors described herein, any of the polypeptides described herein, or a cell comprising such nucleic acid molecule, vector or polypeptide.

In one embodiment of any aspect, the composition further comprises a pharmaceutically acceptable carrier.

Another aspect of the technology described herein provides a pharmaceutical composition comprising any of the isolated nucleic acid molecules, vectors, or polypeptides described herein.

Another aspect of the technology described herein provides a method of treating a cardiac disease or disorder, the method comprising administering to a subject in need thereof any of the compositions or pharmaceutical compositions described herein.

In one embodiment of any aspect, the cardiac disease or disorder is myocardial infarction or myocardial ischemia.

In one embodiment of any aspect, the composition is administered directly to a cardiac cell. In one embodiment of any aspect, the cardiac cell is a cardiomyocyte.

In one embodiment of any aspect, administering increases dATP in a cardiac cell as compared to an appropriate control. For example, dATP is increased at least 50%, least 60%, at least 70%, at 80%, at least 90%, at least 95%, at least 99% or more as compared to an appropriate control.

In one embodiment of any aspect, dATP levels are measured via HPLC and/or mass spectrometry.

In one embodiment of any aspect, administering increases RNR enzymatic activity in a cell as compared to an appropriate control. For example, RNR enzymatic activity is increased at least 50%, least 60%, at least 70%, at 80%, at least 90%, at least 95%, at least 99% or more as compared to an appropriate control.

In one embodiment of any aspect, the method further comprises, prior to administering, diagnosing a subject as having a cardiac disease or disorder.

In one embodiment of any aspect, the method further comprises, prior to administering, receiving the results of an assay that diagnoses a subject as having a cardiac disease or disorder.

In one embodiment of any aspect, the method further comprises administering at least a second therapeutic.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN 1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The terms "increased" or "increase" are all used herein to mean an increase by a statically significant amount. In some embodiments, the terms "increased" or "increase" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level (e.g. the absence of an isolated nucleic acid molecule, polypeptide, vector, composition, or pharmaceutical composition described herein), or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of an isolated nucleic acid molecule, polypeptide, vector, composition, or pharmaceutical composition described herein) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that provide animal models of disease e.g., cardiac disease or disorder, such as myocardial infarction or myocardial ischemia. A subject can be male or female.

A subject can be one who has been previously diagnosed with or identified as suffering from or having a condition in need of treatment (e.g. myocardial infarction or myocardial ischemia) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

A "subject in need" of treatment for a particular condition can be a subject having that condition (e.g., myocardial infarction or myocardial ischemia), diagnosed as having that condition, or at risk of developing that condition. Risk factors for myocardial infarction or myocardial ischemia include, but are not limited to high blood pressure, obesity, high cholesterol levels, having diabetes, or the subject is a smoker.

As used herein, "ubiquitin-binding degron" refers to a region of a polypeptide sequence that is highly targeted by ubiquitin. A ubiquitin-binding degron can be a short amino acid sequence, a structural motif, or exposed amino acids (e.g., a lysine or an arginine). One skilled in the art can determine if a region of a polypeptide sequence is a ubiquitin-binding degron as described herein, e.g., by determining if the mutation or deletion of the sequence in the protein results in decreased levels of ubiquitination (e.g., as identified by a decrease in ubiquitin-mediated degradation). Alternatively, a ubiquitin-binding degron can be identified, if, e.g., the insertion of the sequence into the sequence of another protein leads to increased ubiquitin-mediated degradation of the protein.

Replacement of one or more amino acids (e.g., 1 amino acid, 2 amino acids, 3 amino acids, 4 amino acids, 5 amino acids, 6 amino acids, 7 amino acids, 8 amino acids, 9 amino acids, or 10 amino acids, or alternatively, 10 or fewer amino acids, 9 or fewer amino acids, 8 or fewer amino acids, 7 or fewer amino acids, 6 or fewer amino acids, 5 or fewer amino acids, 4 or fewer amino acids, 3 or fewer amino acids, or two or fewer amino acids) in a ubiquitination site or ubiquitin-binding degron can abrogate the ubiquitination site or reduce the efficiency of ubiquitination at that site. Where it is important to maintain the function of the mutant polypeptide, i.e., complex formation with Rrm1 and/or ribonucleotide reductase activity in complex with Rrm1, it can be beneficial to modify a ubiquitination site or sites via conservative amino acid substitution(s). In a conservative substitution, a given amino acid can be replaced by a residue having similar physicochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., complex formation with Rrm1 and/or ribonucleotide reductase activity for the Rrm1/Rrm2 mutant polypeptide complex is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val;

Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure. Indeed, it can be helpful in determining whether a given region of a polypeptide is likely to tolerate mutation, whether conservative or not, by alignment of the polypeptide's sequence from one species, e.g., human, with the sequence of one or more homologous polypeptides from other species, e.g., the sequences of the homologous polypeptide from one or more of rat, mouse, chicken, bovine, porcine or other species in order to determine which regions of the polypeptide molecule are more highly conserved than others throughout evolution. Indeed, it can also help, for a polypeptide connected to a process as centrally important as dATP production, to consider alignments with Rrm2 sequences from more distantly-related eukaryotes, such as fish, reptiles or others. Those regions more highly conserved are more likely to be important for function, meaning that if a ubiquitination site occurs in such region, care should be taken when choosing mutations to introduce so as not to overly interfere with enzymatic function. In such instances, it can be helpful to try several different conservative substitutions at a chosen site—if the change is not marked enough to interfere sufficiently with ubiquitination, no benefit would be expected for such mutant, but a more dramatic change is more likely to interfere with other function(s) of the polypeptide. On the other hand, if a ubiquitination site or ubiquitin-binding degron occurs in a less conserved region of the polypeptide, the polypeptide may well tolerate substitution with one or more non-conservative amino acids to interfere with ubiquitination, as well as tolerating conservative substitution(s).

In some embodiments, a polypeptide described herein (or a nucleic acid encoding such a polypeptide) can be a functional fragment of one of the polypeptides described herein, e.g., a functional fragment of an Rrm2 polypeptide. As used herein, a "functional fragment" is a fragment or segment of a peptide which retains at least 50% of the wildtype reference polypeptide's activity according to an assay known in the art or described below herein. For example, a functional fragment described herein would retain at least 50% of the Rrm2 function, e.g., can form a complex with Rrm1 and together catalyze the reaction(s) catalyzed by RNR. One skilled in the art can assess the function of an Rrm2 enzyme using standard techniques, for example those described herein below. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant or other reference (e.g., homologue, variant, etc.) sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

As used herein, the term "DNA" is defined as deoxyribonucleic acid. The term "polynucleotide" is used herein interchangeably with "nucleic acid" to indicate a polymer of nucleosides. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule)

are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

As used herein, "half-life" is a measure of the stability of a biological molecule in a biological system, e.g., within a cell or tissue. The "half-life" of a polypeptide (or a nucleic acid, such as an RNA molecule) refers to the time it takes for a given quantity of the polypeptide, e.g., an Rrm2 polypeptide, to be decreased by half Factors other than ubiquitination can contribute to overall degradation of intracellular polypeptides, and thus the half-life of the molecules, but the stability of Rrm2 was found to be significantly influenced by ubiquitin-mediated degradation. As used herein, "increase in half-life" refers to the positive change in half-life of a modified biologically active molecule relative to its non-modified form. Half-life of modified Rrm2 can be measured by, e.g., pulse chase or cycloheximide treatment. Measurement of intracellular half-life of Rrm2 for a modified polypeptide as described herein can be performed in culture, e.g., in cultured IPS-derived human cardiomyocytes following introduction of nucleic acid sequences or a vector encoding the modified polypeptide to the cultured cells. Following administration of a composition as described herein that provides expression of a modified Rrm2 polypeptide, half-life of Rrm2 can be measured by pulse-chase labeling or by cycloheximide treatment to shut down new protein biosynthesis. Rrm2 can be detected by immunological methods, e.g., Western Blot, ELISA, immunoprecipitation, etc. as known to those of ordinary skill in the art. An increase in half-life will generally lead to an increase in steady state level of the polypeptide. The increase in the steady-state level is desirably at least about two-fold, but a smaller increase can be useful, for example where it permits a satisfactory increase in dATP in the cell. Preferably the increase is at least 10%, at least 20%, at least 30%, at least 40%, at least 50%, at least 60%, at least 70%, at least 80%, at least 90%, at least 95%, at least 99% or more, or at least 1-fold, at least 2-fold, at least 3-fold, at least 4-fold, at least 5-fold, at least 6-fold, at least 7-fold, at least 8-fold, at least 9-fold, at least 10-fold or more.

As used herein, "vector" refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "viral vector" refers to a nucleic acid vector construct that includes at least one element of viral origin and has the capacity to be packaged into a viral particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "administering," refers to the placement of a therapeutic or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the technology.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined within the description of the various aspects and embodiments of the technology of the following.

BRIEF DESCRIPTION OF DRAWINGS

FIG. 1A is a line graph showing that isometric force of demembranated cardiac trabeculae increases with 2% dATP, 98% ATP vs. 100% ATP. FIG. 1A is adapted from Korte et al., J Mol Cell Cardiol. 2011 December; 51(6):894-901. FIG. 1B-FIG. 1E are a series of graphs and schematics showing that AAV6-mediated cardiac-specific overexpression of ribonucleotide reductase enhances myocardial contractility. FIG. 1B is a schematic showing an AAV6 vector expressing human RRM1 cDNA and human RRM2 cDNA. FIG. 1C is a series of bar graphs showing that cardiac function was increased with RRM1 and RRM2 overexpression. Cardiac function was assessed in isolated perfused mouse hearts 4 weeks post-rAAV6 injection (grey hatched) or control (white). Left ventricular (LV) developed pressure denotes the difference of LV systolic and LV diastolic pressures. Positive rate of pressure change calculated by the first derivative of the ascending LV pressure wave (+dP/dt) is used as an index of the rate of pressure development. Negative rate of pressure change calculated by the first derivative of the descending LV pressure wave (−dP/dt) is used as an index of the rate of ventricular relaxation. FIG. 1D shows Western blot analysis of Rrm1 and Rrm2 protein levels in mouse liver, heart, and skeletal muscle 4 weeks postsystemic rAAV6 delivery. Significant overexpression of both Rrm1 and Rrm2 was detected in ventricles but not in the livers of treated mice, and essentially no expression of either endogenous subunit was detected in control heart or liver. FIG. 1E is a line graph showing that injection of rAAV6-rat(R1R2)cTnT455 improves in vivo cardiac function in rats subjected to myocardial infarction (MI). Direct injection of rAAV6-rat(R1R2) into the noninfarcted myocardium was made 5 days after ligation of the left anterior descending artery (MI±R1R2) or sham surgery. Serial echocardiography measures were performed at 2, 4, and 8 weeks postinfarction. FIG. 1B-FIG. 1E are adapted from Kolwicz et al., Mol Ther. 2016 February; 24(2):240-250.

FIG. 5A shows a Western blot analysis of Rrm1 and Rrm2 proteins in neonatal rat cardiomyocytes transduced for three days in vitro with AV-RNR, with or without a 3-hour incubation in MG-132, a potent proteasome inhibitor. FIG. 5B is a bar graph showing dATP levels. Note that Rrm2 protein levels and dATP levels are highest with MG132 treatment.

FIG. 6A shows a Western blot analysis of Rrm1 and Rrm2 proteins in WT or Rrm2 mutant cells. FIG. 6B is a dot plot showing the ratio of the Rrm2 protein levels for each Rrm mutant compared to the protein level for wild-type (WT) Rrm2. FIG. 6C is a bar graph showing the ratio of dATP levels to ATP levels for each Rrm mutant or WT Rrm2.

FIG. 8 is a series of schematics showing degron locations and engineered mutations in the Rrm2 nucleic acid sequence. Rrm2 is shown on top with five exemplary Rrm2 mutants aligned at the bottom: 30AAA, 30AAN, 33A, 49ARA, and 30AAA/49ARA double mutant. Note that the nucleic acid sequences shown are the non-coding sequence of each, i.e., reverse complement of the coding sequence. For coding sequences of each mutant see e.g., SEQ ID NOs: 16-20. Figure discloses SEQ ID NOS 26-27, 26, and 28-32, respectively, in order of appearance. Figure also discloses "KEN," "T," and "RRI" as SEQ ID NOS 13-15, respectively.

DETAILED DESCRIPTION

Ribonucleotide Reductase Complex

Figure 1A:
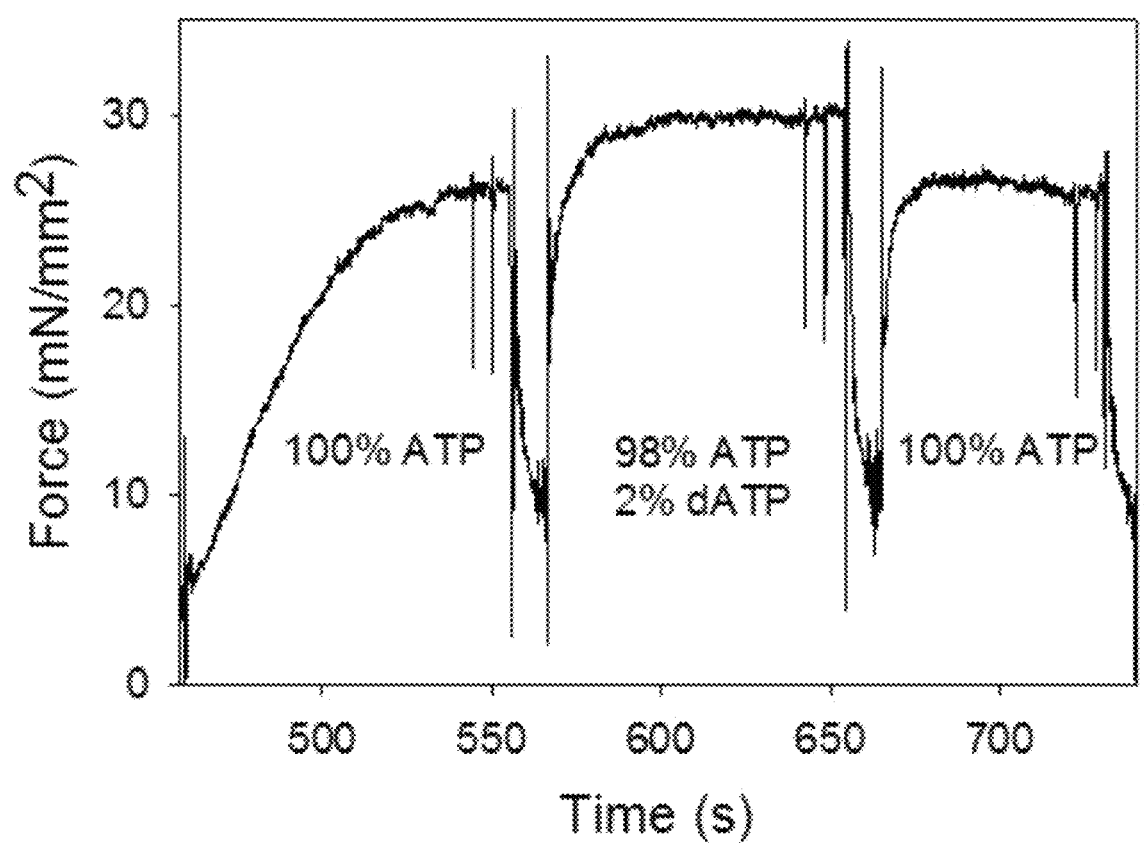
FIG. 1A-FIG. 1E are a series of graphs and schematics showing that dATP increases contractility in cardiac myosin.
Figure 1B:
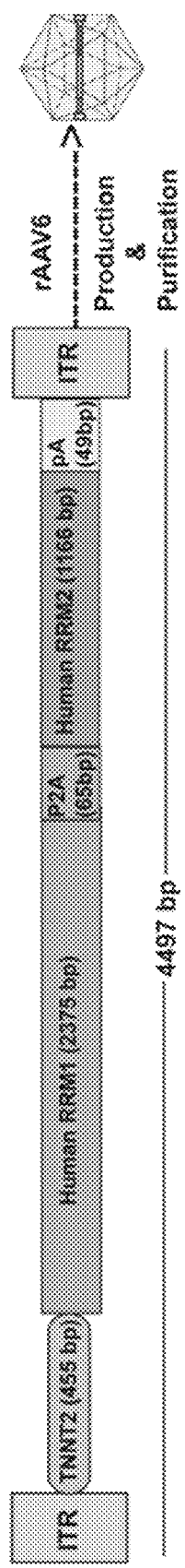
Figure 1C:
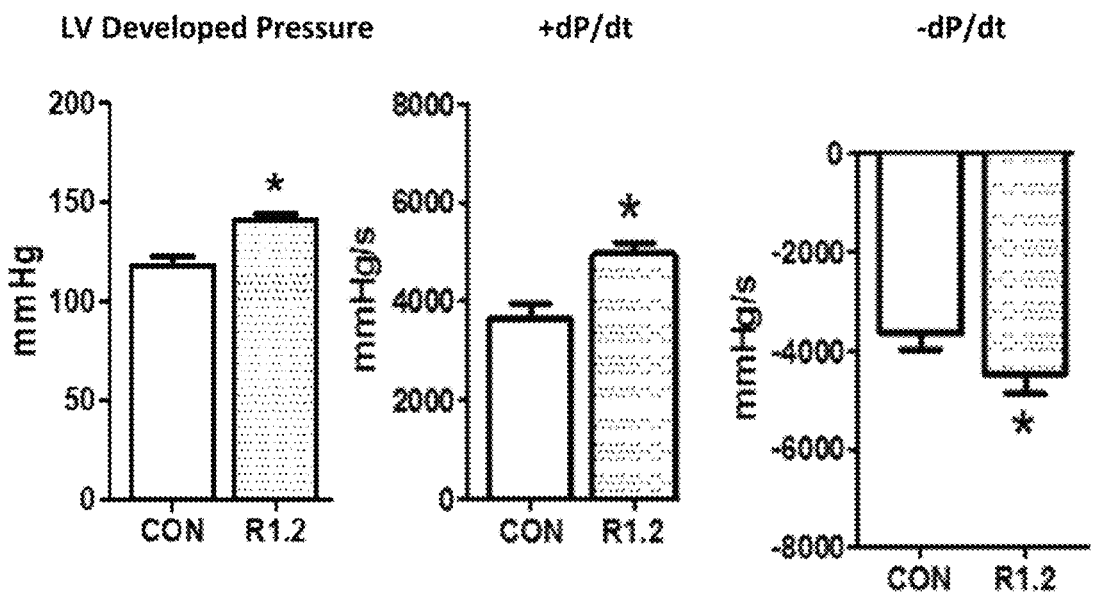
Figure 1D:
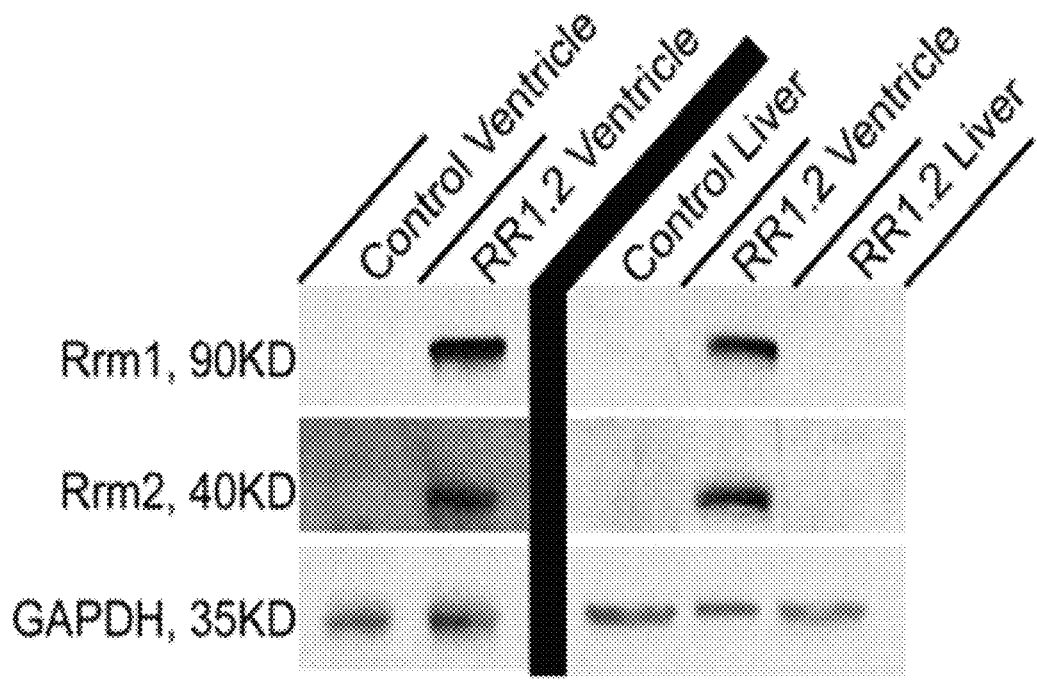
Figure 1E:
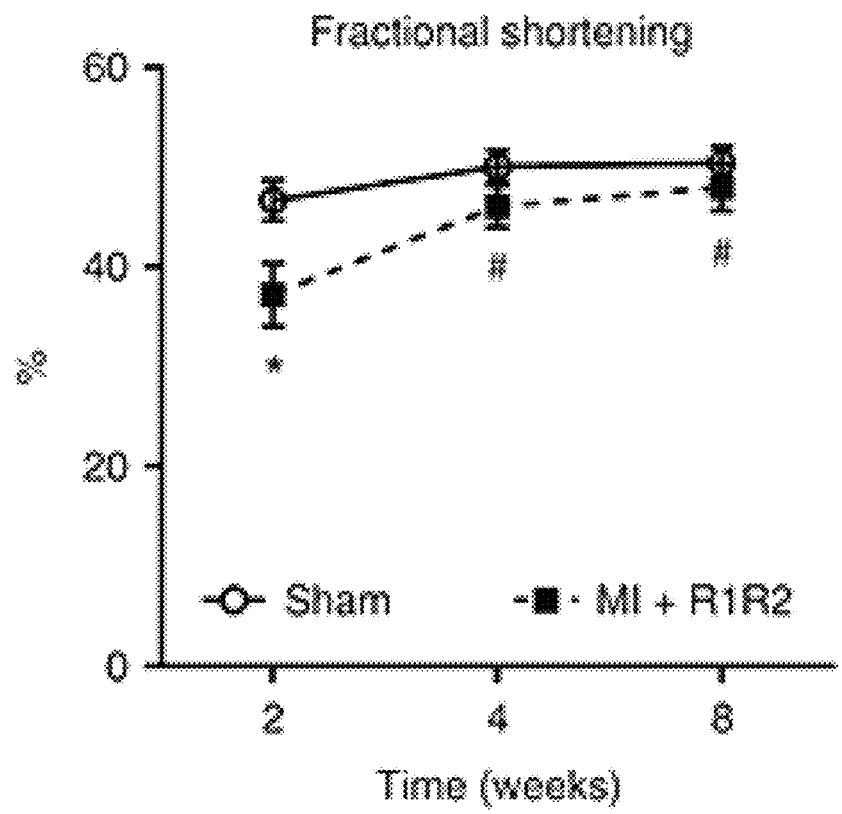

Ribonucleotide reductase (RNR), also known as ribonucleotide diphosphate reductase (rNDP), is an enzyme that catalyzes the reaction of ribonucleotides to deoxyribonucleotides, which are essential components in the synthesis of DNA. RNR is conserved in all living organisms. The RNR enzyme catalyzes the de novo synthesis of dNDPs. Catalysis of ribonucleoside 5'-diphosphates (NDPs) involves a reduction at the 2'-carbon of ribose 5-phosphate to form the 2'-deoxy derivative-reduced 2'-deoxyribonucleoside 5'-diphosphates (dNDPs). This reduction is initiated with the generation of a free radical. Following a single reduction, RNR requires electrons donated from the dithiol groups of the protein thioredoxin. Regeneration of thioredoxin occurs when nicotinamide adenine dinucleotide phosphate (NADPH) provides two hydrogen atoms that are used to reduce the disulfide groups of thioredoxin.

Three classes of RNR have similar mechanisms for the reduction of NDPs. All classes use free-radical chemistry. Class I reductases use an iron center with ferrous to ferric conversion to generate a tyrosyl free radical. Reduction of NDP substrates occurs under aerobic conditions. Class I reductases are divided into IA and IB due to differences in regulation. Class IA reductases are distributed in eukaryotes, eubacteria, bacteriophages, and viruses. Class IB reductases are found in eubacteria. Class IB reductases can also use a radical generated with the stabilization of a binuclear manganese center. Class II reductases generate the free radical 5'-deoxyadenosyl radical from cobalamin (coenzyme B12) and have a simpler structure than class I and class III reductases. Reduction of NDPs or ribonucleotide 5'-triphosphates (NTPs) occurs under either aerobic or anaerobic conditions. Class II reductases are distributed in archaebacteria, eubacteria, and bacteriophages. Class III reductases use a glycine radical generated with the help of an S-adenosyl methionine and an iron sulphur center. Reduction of NTPs is limited to anaerobic conditions. Class III reductases are distributed in archaebacteria, eubacteria, and bacteriophages. Organisms are not limited to having one class of enzymes. For example, $E.\ coli$ have both class I and class III RNR.

The RNR complex consists of two subunits—Rrm1 and Rrm2. The larger Rrm1 subunit contains the catalytic site and 2 allosteric sites that can bind dATP, whereas the smaller Rrm2 subunit contains the free radical generator. The RNR complex is tightly allosterically regulated, with ≤5% of the ATP pool present as dATP. Each RNR1 monomer consists of three domains: (1) one mainly helical domain comprising the 220 N-terminal residues; (2) a second large ten-stranded $\alpha/\beta$ structure comprising 480 residues; and (3) a third small five-stranded $\alpha/\beta$ structure comprising 70 residues.

As used herein, "Rrm1" or "ribonucleotide reductase catalytic subunit M1" refers to the large, catalytic site containing, subunit of the RNR complex. Sequences for Rrm1 are known for a number of species, e.g., human Rrm1 (NCBI Gene ID: 6240) mRNA (NCBI Ref Seq: NM_001033.5) and polypeptide (NCBI Ref Seq: NP_001024.1). In some embodiments of any of the aspects, the Rrm1 nucleic acid or polypeptide can be an isoform, ortholog, variant, and/or allele of SEQ ID NO: 1 or 2, respectively.

As used herein, "Rrm2" or "ribonucleotide reductase catalytic subunit M2" refers to the small subunit of the RNR complex. Sequences for Rrm2 are known for a number of species, e.g., human Rrm2 (NCBI Gene ID: 6241) mRNA (NCBI Ref Seq: NM_001034.4) and polypeptide (NCBI Ref Seq: NP_001025.1). In some embodiments of any of the aspects, the Rrm2 nucleic acid or polypeptide can be an isoform, ortholog, variant, and/or allele of SEQ ID NO: 3 or 4, respectively.

```
SEQ ID NO: 1 is the nucleotide sequence encoding Rrm1, isoform 1.
                                                         (SEQ ID NO: 1)
                                        atgcat gtgatcaagc gagatggccg 241    ccaagaacga gtcatgtttg acaaaattac atctcgaatc cagaagcttt gttatggact 301    caatatggat tttgttgatc ctgctcagat caccatgaaa gtaatccaag gcttgtacag 361    tggggtcacc acagtggaac tagatacttt ggctgctgaa acagctgcaa ccttgactac 421    taagcaccct gactatgcta tcctggcagc caggatcgct gtctctaact tgcacaaaga 481    aacaaagaaa gtgttcagtg atgtgatgga agacctctat aactacataa atccacataa 541    tggcaaacac tctcccatgg tggccaagtc aacattggat attgttctgg ccaataaaga 601    tcgcctgaat tctgctatta tctatgaccg agatttctct tacaattact tcggctttaa 661    gacgctagag cggtcttatt tgttgaagat caatggaaaa gtggctgaaa gaccacaaca 721    tatgttgatg agagtatctg ttgggatcca caaagaagac attgatgcag caattgaaac 781    atataatctt ctttctgaga ggtggtttac tcatgcttcg cccactctct tcaatgctgg 841    taccaaccgc ccacaacttt ctagctgttt tcttctgagt atgaaagatg acagcattga 901    aggcatttat gacactctaa agcaatgtgc attgatttct aagtctgctg gaggaattgg 961    tgttgctgtg agttgtattc gggctactgg cagctacatt gctgggacta atggcaattc 1021    caatggcctt gtaccgatgc tgagagtata taacaacaca gctcgatatg tggatcaagg 1081    tgggaacaag cgtcctgggg catttgctat ttacctggag ccttggcatt tagacatctt 1141    tgaattcctt gatttaaaga agaacacagg aaaggaagag cagcgtgcca gagatctttt 1201    ctttgctctt tggattccgg atctcttcat gaaacgagtg gagactaatc aggactggtc 1261    tttgatgtgt ccaaatgagt gtcctggtct ggatgaggtt tggggagagg aatttgagaa 1321    actatatgca agttatgaga aacaaggtcg tgtccgcaaa gttgtaaaag ctcagcagct 1381    ttggtatgcc atcattgagt ctcagacgga aacaggcacc ccgtatatgc tctacaaaga 1441    ttcctgtaat cgaaagagca accagcagaa cctgggaacc atcaaatgca gcaacctgtg 1501    cacagaaata gtggagtaca ccagcaaaga tgaggttgct gtttgtaatt tggcttccct
```

-continued

```
1561  ggccctgaat atgtatgtca catcagaaca cacatacgac tttaagaagt tggctgaagt
1621  cactaaagtc gttgtccgaa acttgaataa aattattgat ataaactact atcctgtacc
1681  agaggcatgc ctatcaaata aacgccatcg ccccattgga attggggtac aaggtctggc
1741  agatgctttt atcctgatga gatacccttt tgagagtgca gaagcccagt tactgaataa
1801  gcagatcttt gaaactattt attatggtgc tctggaagcc agctgtgacc ttgccaagga
1861  gcagggccca tacgaaacct atgagggctc tccagttagc aaaggaattc ttcagtatga
1921  tatgtggaat gttactccta cagacctatg ggactggaag gttctcaagg agaagattgc
1981  aaagtatggt ataagaaaca gtttacttat tgccccgatg cctacagctt ccactgctca
2041  gatcctgggg aataatgagt ccattgaacc ttacaccagc aacatctata ctcgcagagt
2101  cttgtcagga gaatttcaga ttgtaaatcc tcacttattg aaagatctta ccgagcgggg
2161  cctatggcat gaagagatga aaaccagat tattgcatgc aatggctcta ttcagagcat
2221  accagaaatt cctgatgacc tgaagcaact ttataaaact gtgtgggaaa tctctcagaa
2281  aactgttctc aagatggcag ctgagagagg tgctttcatt gatcaaagcc aatctttgaa
2341  catccacatt gctgagccta actatggcaa actcactagt atgcacttct acggctggaa
2401  gcagggtttg aagactggga tgtattattt aaggacaaga ccagcggcta atccaatcca
2461  gttcactcta aataaggaga agctaaaaga taagaaaaag gtatcaaaag aggaagaaga
2521  gaaggagagg aacacagcag ccatggtgtg ctctttggag aatagagatg aatgtctgat
2581  gtgtggatcc tga
```

SEQ ID NO: 2 is the amino acid sequence for Rrm1, isoform 1.
(SEQ ID NO: 2)

MHVIKRDGRQERVMFDKITSRIQKLCYGLNMDFVDPAQITMKVI
QGLYSGVTTVELDTLAAETAATLTTKHPDYAILAARIAVSNLHKETKKVFSDVMEDLY
NYINPHNGKHSPMVAKSTLDIVLANKDRLNSAITYDRDFSYNYFGEKTLERSYLLKIN
GKVAERPQHMLRVSVGIHKEDIDAAIETYNLLSERWFTHASPTLFNAGTNRPQLSSC
FLLSMKDDSIEGIYDTLKQCALISKSAGGIGVAVSCIRATGSYIAGTNGNSNGLVPML
RVYNNTARYVDQGGNKRPGAFAIYLEPWHLDIFEFLDLKKNTGKEEQRARDLFFALWI
PDLFMKRVETNQDWSLMCPNECPGLDEVWGEEFEKLYASYEKQGRVRKVVKAQQLWYA
IIESQTETGTPYMLYKDSCNRKSNQQNLGTIKCSNLCTEIVEYTSKDEVAVCNLASLA
LNMYVTSEHTYDFKKLAEVTKVVVRNLNKIIDINYYPVPEACLSNKRHRPIGIGVQGL
ADAFILMRYPFESAEAQLLNKQIFETIYYGALEASCDLAKEQGPYETYEGSPVSKGIL
QYDMWNVTPTDLWDWKVLKEKIAKYGIRNSLLIAPMPTASTAQILGNNESIEPYTSNI
YTRRVLSGEFQIVNPHLLKDLTERGLWHEEMKNQIIACNGSIQSIPEIPDDLKQLYKT
VWEISQKTVLKMAAERGAFIDQSQSLNIHIAEPNYGKLTSMHFYGWKQGLKTGMYYLR
TRPAANPIQFTLNKEKLKDKEKVSKEEEEKERNTAAMVCSLENRDECLMCGS

SEQ ID NO: 3 is the nucleotide sequence encoding Rrm2, isoform 2.
(SEQ ID NO: 3)

ATGCTCTCCCTCCGTGTCCCGCTCGCGCCCATCACGGACCCGCAGCAGCTGCAGCTCTCGCCGCTGAAGGGGC
TCAGCTTGGTCGACAAGGAGAACACGCCGCCGGCCCTGAGCGGGACCCGCGTCCTGGCCAGCAAGACCGCGAG
GAGGATCTTCCAGGAGCCCACGGAGCCGAAAACTAAAGCAGCTGCCCCCGGCGTGGAGGATGAGCCGCTGCTG
AGAGAAAACCCCCGCCGCTTTGTCATCTTCCCCATCGAGTACCATGATATCTGGCAGATGTATAAGAAGGCAG
AGGCTTCCTTTTGGACCGCCGAGGAGGTGGACCTCTCCAAGGACATTCAGCACTGGGAATCCCTGAAACCCGA
GGAGAGATATTTTATATCCCATGTTCTGGCTTTCTTTGCAGCAAGCGATGGCATAGTAAATGAAAACTTGGTG

-continued

```
GAGCGATTTAGCCAAGAAGTTCAGATTACAGAAGCCCGCTGTTTCTATGGCTTCCAAATTGCCATGGAAAACA

TACATTCTGAAATGTATAGTCTTCTTATTGACACTTACATAAAAGATCCCAAAGAAAGGGAATTTCTCTTCAA

TGCCATTGAAACGATGCCTTGTGTCAAGAAGAAGGCAGACTGGGCCTTGCGCTGGATTGGGGACAAAGAGGCT

ACCTATGGTGAACGTGTTGTAGCCTTTGCTGCAGTGGAAGGCATTTTCTTTTCCGGTTCTTTTGCGTCGATAT

TCTGGCTCAAGAAACGAGGACTGATGCCTGGCCTCACATTTTCTAATGAACTTATTAGCAGAGATGAGGGTTT

ACACTGTGATTTTGCTTGCCTGATGTTCAAACACCTGGTACACAAACCATCGGAGGAGAGAGTAAGAGAAATA

ATTATCAATGCTGTTCGGATAGAACAGGAGTTCCTCACTGAGGCCTTGCCTGTGAAGCTCATTGGGATGAATT

GCACTCTAATGAAGCAATACATTGAGTTTGTGGCAGACAGACTTATGCTGGAACTGGGTTTTAGCAAGGTTTT

CAGAGTAGAGAACCCATTTGACTTTATGGAGAATATTTCACTGGAAGGAAAGACTAACTTCTTTGAAGAGA

GTAGGCGAGTATCAGAGGATGGGAGTGATGTCAAGTCCAACAGAGAATTCTTTTACCTTGGATGCTGACTTCT

AA
```

SEQ ID NO: 4 is the amino acid sequence for Rrm2, isoform 2.
(SEQ ID NO: 4)

```
MLSLRVPLAPITDPQQLQLSPLKGLSLVDKENTPPALSGTRVLASKTARRIFQEPTEPKTKAAAPGVEDEPLL

RENPRRFVIFPIEYHDIWQMYKKAEASFWTAEEVDLSKDIQHWESLKPEERYFISHVLAFFAASDGIVNENLV

ERFSQEVQITEARCFYGFQIAMENIHSEMYSLLIDTYIKDPKEREFLFNAIETMPCVKKKADWALRWIGDKEA

TYGERVVAFAAVEGIFESGSFASIFWLKKRGLMPGLTFSNELISRDEGLHCDFACLMFKHLVHKPSEERVREI

IINAVRIEQEFLTEALPVKLIGMNCTLMKQYIEFVADRLMLELGESKVERVENPFDEMENISLEGKTNFFEKR

VGEYQRMGVMSSPTENSFTLDADF
```

One aspect described herein is an RNR complex comprising, consisting of, or consisting essentially of, a wild type Rrm1 protein and a Rrm2 protein encoded by any of the isolated nucleic acids described herein. As used herein, "RNR complex" refers to Rrm1 and Rrm2 in physical association with each other in the form that provides RNR activity. One skilled in the art can assess whether the RNR complex is formed, for example, by sucrose gradient analysis or co-immunoprecipitation under non-denaturing conditions.

In one embodiment, the RNR complex provided herein comprises the same enzymatic function of a wild-type RNR complex, for example, catalyzing the formation of deoxyribonucleotides from ribonucleotides. Assays for assessing the enzymatic function of a complex provided herein include, but are not limited to nucleotide binding assays, for example, as described in Chimploy, K., and Mathews, C K. J of Biol Chem, 2001; Hendricks, S P, and Mathews C K. J of Biol Chem, 1997; and Hendricks, S P, and Mathews C K. J of Biol Chem, 1998; the content of which are incorporated herein by reference.

In one embodiment, the nucleic acid (or vector comprising a nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In one embodiment, the expression system is an organism other than the source of the native/wild-type sequence (or a cell obtained from such organism). In one embodiment, the vector and/or nucleic acid sequence described herein is codon-optimized for expression in a mammal or mammalian cell, e.g., a mouse, a murine cell, or a human cell. In one embodiment, the vector and/or nucleic acid sequence described herein is codon-optimized for expression in a human cell. In one embodiment, the vector and/or nucleic acid sequence described herein is codon-optimized for expression in a yeast or yeast cell. In one embodiment, the vector and/or nucleic acid sequence described herein is codon-optimized for expression in a bacterial cell. In one embodiment, the vector and/or nucleic acid sequence described herein is codon-optimized for expression in an E. coli cell. In one embodiment, the Rrm2 (and/or Rrm1) nucleic acid sequence is codon-optimized (see e.g., SEQ ID NO: 5).

SEQ ID NO: 5 is an exemplary codon-optimized Rrm2 nucleic acid sequence.

```
ATGCTGAGTCTGAGGGTCCCACTGGCACCTATCACCGATCCACAGCAGCT

GCAGCTGAGCCCACTGAAAGGCCTGAGTCTGGTCGATAAAGAGAACACAC

CACCTGCACTGAGTGGCACTCGGGTGCTGGCATCAAAGACCGCCCGGAGA

ATTTTCCAGGAGCCAACCGAACCCAAAACAAAGGCCGCTGCACCTGGGGT

CGAGGACGAACCACTGCTGAGAGAGAATCCCAGGCGCTTCGTGATTTTTC

CTATCGAATACCACGATATTTGGCAGATGTATAAGAAAGCTGAGGCAAGT

TTCTGGACAGCTGAGGAAGTGGACCTGAGCAAAGACATCCAGCACTGGGA

ATCCCTGAAGCCAGAGGAAAGGTACTTCATTTCTCATGTGCTGGCATTCT

TTGCCGCTAGTGACGGGATCGTGAACGAGAATCTGGTCGAACGCTTTAGC

CAGGAGGTGCAGATCACTGAAGCCCGATGCTTCTATGGATTTCAGATTGC

TATGGAGAACATCCATTCAGAAATGTACAGCCTGCTGATTGACACCTATA

TCAAAGATCCTAAGGAGCGCGAGTTCCTGTTTAATGCCATTGAGACAATG

CCATGTGTGAAGAAAAAGGCAGACTGGGCTCTGCGATGGATCGGCGATAA
```

```
GGAGGCTACTTACGGGGAAAGAGTGGTCGCATTCGCAGCCGTGGAGGGAA

TTTTCTTTTCTGGCAGTTTCGCTTCCATCTTTTGGCTGAAAAAGCGAGGC

CTGATGCCTGGGCTGACCTTTTCCAACGAGCTGATTTCTCGCGACGAAGG

CCTGCACTGCGATTTCGCCTGTCTGATGTTTAAACACCTGGTGCATAAGC

CCTCTGAGGAACGAGTCCGGGAGATCATTATCAACGCAGTGAGGATCGAG

CAGGAGTTCCTGACAGAAGCCCTGCCTGTCAAACTGATTGGCATGAATTG

CACTCTGATGAAGCAGTACATCGAGTTTGTGGCCGACAGGCTGATGCTGG

AACTGGGATTCTCAAAGGTGTTTCGCGTCGAGAACCCATTCGATTTTATG

GAGAATATCAGCCTGGAAGGCAAAACAAACTTCTTTGAGAAGAGAGTCGG
```

```
GGAATATCAGAGGATGGGCGTGATGAGCAGCCCCACTGAGAATAGCTTCA

CCCTGGACGCCGATTTTTGA
```

In one embodiment, the Rrm2 and Rrm1 mRNAs are bicistronic, i.e., on the same vector and/or under the control of the same promoter. In one embodiment, the Rrm2 nucleic acid is linked to Rrm1, e.g., through a P2A sequence. P2A is a non-limiting example of a 2A self-cleaving peptide, which can induce the cleaving of the recombinant protein in cell. In one embodiment, the Rrm2 nucleic acid is linked to Rrm1, e.g., through a 2A self-cleaving peptide sequence. Non-limiting examples of 2A self-cleaving peptides include T2A, P2A, E2A, and F2A. Any self-cleaving peptide sequence known in the art can be used to link Rrm2 to Rrm2.

SEQ ID NO: 6 is an exemplary nucleic acid sequence comprising a Kozak sequence, Rrm1, P2A, and Rrm2.

```
GCTAGCGAATTCGCCACCATGCACGTCATCAAGAGAGACGGGAGGCAGGAAAGAGTCATGT

TCGATAAAATCACTTCAAGAATCCAGAAACTGTGTTACGGGCTGAACATGGACTTCGTCGAT

CCTGCCCAGATTACCATGAAAGTGATCCAGGGACTGTACTCTGGCGTCACCACAGTGGAGCT

GGACACACTGGCCGCTGAAACCGCAGCCACACTGACTACCAAACACCCAGATTATGCAATT

CTGGCTGCACGGATCGCCGTGAGTAATCTGCATAAGGAGACAAAGAAAGTCTTCTCAGACG

TGATGGAGGACCTGTACAATTATATCAACCCTCACAATGGGAAACATTCACCAATGGTCGCT

AAGAGCACTCTGGACATTGTGCTGGCCAACAAAGATCGGCTGAACAGCGCTATCATCTACG

ACCGGGATTTCAGTTACAACTACTTCGGCTTTAAGACACTGGAGAGATCATATCTGCTGAAA

ATCAATGGGAAGGTGGCCGAACGGCCTCAGCACATGCTGATGAGAGTCAGCGTGGGCATTC

ATAAGGAGGACATTGATGCCGCTATCGAAACTTACAACCTGCTGAGCGAGCGCTGGTTCAC

CCACGCTTCCCCTACACTGTTTAACGCAGGAACCAATCGACCACAGCTGAGCAGCTGCTTCC

TGCTGAGCATGAAGGACGATTCCATCGAGGGCATCTACGACACCCTGAAACAGTGCGCACT

GATTTCTAAGAGTGCCGGCGGGATCGGAGTCGCTGTGAGTTGTATTCGGGCAACCGGCTCAT

ATATCGCCGGCACAAACGGCAACAGCAACGGGCTGGTCCCCATGCTGAGGGTGTACAACAA

TACAGCCCGCTATGTGGATCAGGGAGGCAACAAGAGACCAGGAGCATTTGCCATCTACCTG

GAACCCTGGCACCTGGACATTTTCGAGTTTCTGGATCTGAAGAAAAATACTGGCAAAGAGG

AACAGAGGGCTCGCGACCTGTTCTTTGCACTGTGGATTCCCGACCTGTTCATGAAGAGGGTG

GAGACCAACCAGGACTGGAGCCTGATGTGCCCCAATGAGTGTCCTGGGCTGGATGAAGTGT

GGGGAGAGGAATTTGAAAAACTGTACGCCAGTTATGAGAAGCAGGGCCGAGTGCGGAAAG

TGGTCAAGGCCCAGCAGCTGTGGTACGCTATCATTGAGAGCCAGACAGAAACTGGCACCCC

CTACATGCTGTATAAAGACTCTTGCAACCGCAAGAGTAACCAGCAGAATCTGGGGACCATC

AAATGCAGCAATCTGTGTACAGAGATTGTGGAATATACTTCCAAGGATGAGGTCGCCGTGT

GTAACCTGGCATCACTGGCCCTGAATATGTACGTCACAAGCGAGCACACTTATGACTTCAAG

AAACTGGCTGAAGTGACCAAAGTGGTCGTGAGGAATCTGAACAAGATCATTGACATCAACT

ACTATCCCGTGCCTGAGGCCTGCCTGAGCAATAAGAGACATAGGCCCATCGGGATTGGAGT

GCAGGGCCTGGCTGACGCATTCATCCTGATGCGCTACCCTTTTGAGTCCGCCGAAGCTCAGC

TGCTGAACAAGCAGATTTTTGAAACAATCTACTACGGGGCTCTGGAGGCATCTTGTGACCTG

GCCAAAGAACAGGGACCCTACGAGACTTATGAAGGCTCCCCTGTGTCTAAGGGCATCCTGC

AGTACGATATGTGGAACGTCACACCAACTGACCTGTGGGATTGGAAAGTGCTGAAGGAGAA
```

-continued

```
AATTGCAAAGTATGGCATCCGGAACAGCCTGCTGATCGCCCAATGCCCACTGCCTCTACCG

CTCAGATTCTGGGCAACAATGAGTCCATCGAACCATACACTTCTAACATCTACACCCGGAGA

GTCCTGAGCGGGGAGTTCCAGATCGTGAATCCCCACCTGCTGAAAGACCTGACCGAACGGG

GACTGTGGCATGAGGAAATGAAGAACCAGATCATTGCCTGCAATGGCAGTATCCAGTCAAT

TCCTGAGATCCCAGACGATCTGAAACAGCTGTACAAGACAGTCTGGGAGATCAGCCAGAAA

ACTGTGCTGAAGATGGCAGCCGAAAGAGGGGCTTTCATTGATCAGTCACAGAGCCTGAACA

TCCACATTGCCGAGCCCAATTACGGAAAGCTGACCTCCATGCATTTTTATGGGTGGAAACAG

GGACTGAAGACTGGCATGTACTATCTGCGCACCCGACCAGCTGCAAACCCCATCCAGTTTAC

CCTGAATAAGGAGAAACTGAAGGACAAAGAAAGGTGTCCAAAGAGGAAGAGGAAAAGG

AGAGAAACACAGCCGCTATGGTGTGTTCTCTGGAGAATAGGGATGAATGCCTGATGTGTGG

CAGTGGAAGCGGAGCTACTAACTTCAGCCTGCTGAAGCAGGCTGGAGACGTGGAGGAGAAC

CCTGGACCTCTGAGTCTGAGGGTCCCACTGGCACCTATCACCGATCCACAGCAGCTGCAGCT

GAGCCCACTGAAAGGCCTGAGTCTGGTCGATAAAGAGAACACACCACCTGCACTGAGTGGC

ACTCGGGTGCTGGCATCAAAGACCGCCCGGAGAATTTTCCAGGAGCCAACCGAACCCAAAA

CAAAGGCCGCTGCACCTGGGGTCGAGGACGAACCACTGCTGAGAGAGAATCCCAGGCGCTT

CGTGATTTTTCCTATCGAATACCACGATATTTGGCAGATGTATAAGAAAGCTGAGGCAAGTT

TCTGGACAGCTGAGGAAGTGGACCTGAGCAAAGACATCCAGCACTGGGAATCCCTGAAGCC

AGAGGAAAGGTACTTCATTTCTCATGTGCTGGCATTCTTTGCCGCTAGTGACGGGATCGTGA

ACGAGAATCGGTCGAACGCTTTAGCCAGGAGGTGCAGATCACTGAAGCCCGATGCTTCTA

TGGATTTCAGATTGCTATGGAGAACATCCATTCAGAAATGTACAGCCTGCTGATTGACACCT

ATATCAAAGATCCTAAGGAGCGCGAGTTCCTGTTTAATGCCATTGAGACAATGCCATGTGTG

AAGAAAAAGGCAGACTGGGCTCTGCGATGGATCGGCGATAAGGAGGCTACTTACGGGGAA

AGAGTGGTCGCATTCGCAGCCGTGGAGGGAATTTTCTTTTCTGGCAGTTTCGCTTCCATCTTT

TGGCTGAAAAAGCGAGGCCTGATGCCTGGGCTGACCTTTTCCAACGAGCTGATTTCTCGCGA

CGAAGGCCTGCACTGCGATTTCGCCTGTCTGATGTTTAAACACCTGGTGCATAAGCCCTCTG

AGGAACGAGTCCGGGAGATCATTATCAACGCAGTGAGGATCGAGCAGGAGTTCCTGACAGA

AGCCCTGCCTGTCAAACTGATTGGCATGAATTGCACTCTGATGAAGCAGTACATCGAGTTTG

TGGCCGACAGGCTGATGCTGGAACTGGGATTCTCAAAGGTGTTTCGCGTCGAGAACCCATTC

GATTTTATGGAGAATATCAGCCTGGAAGGCAAAACAAACTTCTTTGAGAAGAGAGTCGGGG

AATATCAGAGGATGGGCGTGATGAGCAGCCCCACTGAGAATAGCTTCACCCTGGACGCCGA

TTTTTGAGCTAGC
```

SEQ ID NO: 7 is an exemplary Kozak sequence (as found in SEQ ID NO: 6).
GCCACC

SEQ ID NO: 8 is an exemplary Rrm1 sequence (as found in SEQ ID NO: 6).
```
ATGCACGTCATCAAGAGAGACGGGAGGCAGGAAAGAGTCATGTTCGATAAAATCACTTCAA

GAATCCAGAAACTGTGTTACGGGCTGAACATGGACTTCGTCGATCCTGCCCAGATTACCATG

AAAGTGATCCAGGGACTGTACTCTGGCGTCACCACAGTGGAGCTGGACACACTGGCCGCTG

AAACCGCAGCCACACTGACTACCAAACACCCAGATTATGCAATTCTGGCTGCACGGATCGC

CGTGAGTAATCTGCATAAGGAGACAAAGAAAGTCTTCTCAGACGTGATGGAGGACCTGTAC

AATTATATCAACCCTCACAATGGGAAACATTCACCAATGGTCGCTAAGAGCACTCTGGACAT

TGTGCTGGCCAACAAAGATCGGCTGAACAGCGCTATCATCTACGACCGGGATTTCAGTTACA

ACTACTTCGGCTTTAAGACACTGGAGAGATCATATCTGCTGAAAATCAATGGGAAGGTGGC
```

```
-continued
CGAACGGCCTCAGCACATGCTGATGAGAGTCAGCGTGGGCATTCATAAGGAGGACATTGAT

GCCGCTATCGAAACTTACAACCTGCTGAGCGAGCGCTGGTTCACCCACGCTTCCCCTACACT

GTTTAACGCAGGAACCAATCGACCACAGCTGAGCAGCTGCTTCCTGCTGAGCATGAAGGAC

GATTCCATCGAGGGCATCTACGACACCCTGAAACAGTGCGCACTGATTTCTAAGAGTGCCG

GCGGGATCGGAGTCGCTGTGAGTTGTATTCGGGCAACCGGCTCATATATCGCCGGCACAAA

CGGCAACAGCAACGGGCTGGTCCCCATGCTGAGGGTGTACAACAATACAGCCCGCTATGTG

GATCAGGGAGGCAACAAGAGACCAGGAGCATTTGCCATCTACCTGGAACCCTGGCACCTGG

ACATTTTCGAGTTTCTGGATCTGAAGAAAAATACTGGCAAAGAGGAACAGAGGGCTCGCGA

CCTGTTCTTTGCACTGTGGATTCCCGACCTGTTCATGAAGAGGGTGGAGACCAACCAGGACT

GGAGCCTGATGTGCCCCAATGAGTGTCCTGGGCTGGATGAAGTGTGGGGAGAGGAATTTGA

AAAACTGTACGCCAGTTATGAGAAGCAGGGCCGAGTGCGGAAAGTGGTCAAGGCCCAGCA

GCTGTGGTACGCTATCATTGAGAGCCAGACAGAAACTGGCACCCCCTACATGCTGTATAAA

GACTCTTGCAACCGCAAGAGTAACCAGCAGAATCTGGGGACCATCAAATGCAGCAATCTGT

GTACAGAGATTGTGGAATATACTTCCAAGGATGAGGTCGCCGTGTGTAACCTGGCATCACTG

GCCCTGAATATGTACGTCACAAGCGAGCACACTTATGACTTCAAGAAACTGGCTGAAGTGA

CCAAAGTGGTCGTGAGGAATCTGAACAAGATCATTGACATCAACTACTATCCCGTGCCTGA

GGCCTGCCTGAGCAATAAGAGACATAGGCCCATCGGGATTGGAGTGCAGGGCCTGGCTGAC

GCATTCATCCTGATGCGCTACCCTTTTGAGTCCGCCGAAGCTCAGCTGCTGAACAAGCAGAT

TTTTGAAACAATCTACTACGGGGCTCTGGAGGCATCTTGTGACCTGGCCAAAGAACAGGGA

CCCTACGAGACTTATGAAGGCTCCCCTGTGTCTAAGGGCATCCTGCAGTACGATATGTGGAA

CGTCACACCAACTGACCTGTGGGATTGGAAAGTGCTGAAGGAGAAAATTGCAAAGTATGGC

ATCCGGAACAGCCTGCTGATCGCCCCAATGCCCACTGCCTCTACCGCTCAGATTCTGGGCAA

CAATGAGTCCATCGAACCATACACTTCTAACATCTACACCCGGAGAGTCCTGAGCGGGGAG

TTCCAGATCGTGAATCCCCACCTGCTGAAAGACCTGACCGAACGGGGACTGTGGCATGAGG

AAATGAAGAACCAGATCATTGCCTGCAATGGCAGTATCCAGTCAATTCCTGAGATCCCAGA

CGATCTGAAACAGCTGTACAAGACAGTCTGGGAGATCAGCCAGAAAACTGTGCTGAAGATG

GCAGCCGAAAGAGGGGCTTTCATTGATCAGTCACAGAGCCTGAACATCCACATTGCCGAGC

CCAATTACGGAAAGCTGACCTCCATGCATTTTTATGGGTGGAAACAGGGACTGAAGACTGG

CATGTACATCTGCGCACCCGACCAGCTGCAAACCCCATCCAGTTTACCCTGAATAAGGAGA

AACTGAAGGACAAAGAAAAGGTGTCCAAAGAGGAAGAGGAAAAGGAGAGAAACACAGCC

GCTATGGTGTGTTCTCTGGAGAATAGGGATGAATGCCTGATGTGTGGCAGT

SEQ ID NO: 9 is an exemplary P2A sequence (as found in SEQ ID NO: 6).
GCTACTAACTTCAGCCTGCTGAAGCAGGCTGGAGACGTGGAGGAGAACCCTGGACCT
```

Rrm2 Mutant

Mutations found within the ubiquitin binding domain (i.e., the site of ubiquitin addition or ubiquitination) of Rrm2 are shown herein to decrease ubiquitination of Rrm2, increase Rrm2 stability (e.g., half-life of Rrm2), and result in increased dATP in the cell. Accordingly, provided herein is an isolated nucleic acid molecule encoding an Rrm2 polypeptide that, together with Rrm1 polypeptide comprises ribonucleotide reductase activity, the encoded Rrm2 polypeptide comprising a mutation that increases the intracellular level of the polypeptide as compared to wild-type Rrm2 polypeptide. In one embodiment, the mutation is in a ubiquitin binding degron of Rrm2. In one embodiment, the ubiquitin binding degrons of Rrm2 are found at nucleotides 88-96 (which encode amino acids that can associate with the APC/FZR1 proteasome) and nucleotides 97-99 and 145-153 (which can associate with the SCF/CyclinF proteasome) of wild-type Rrm2 (SEQ ID NO: 3). In one embodiment, the ubiquitin binding degrons of Rrm2 are found at amino acids 30-32 (which can associate with the APC/FZR1 proteasome) and amino acids 33 and 49-51 (which can associate with the SCF/CyclinF proteasome) of wild-type Rrm2 (SEQ ID NO: 4).

In one embodiment, the ubiquitin binding degrons of Rrm2 have the nucleic acid sequence of SEQ ID NOs: 10-12 or the amino acid sequence of SEQ ID NOs: 13-15. SEQ ID NO: 10 AAGGAGAAC; SEQ ID NO: 11 ACG; SEQ ID NO: 12 AGGAGGATC; SEQ ID NO: 13 KEN; SEQ ID NO: 14 T; SEQ ID NO: 15 RRI.

In one embodiment, the mutant Rrm2 having mutations within the ubiquitin binding degrons of Rrm2 have one mutation, at least one mutation, at least 2 mutations, at least 3 mutations, at least 4 mutations, at least 5 mutations, at least 6 mutations, at least 7 mutations, at least 8 mutations, at least 9 mutations, or 10 mutations, or more. Alternatively, the mutant Rrm2 can include 1 mutation, two or fewer mutations, three or fewer mutations, four or fewer mutations, five or fewer mutations, six or fewer mutations, seven or fewer mutations, eight or fewer mutations, nine or fewer mutations or 10 or fewer mutations, relative to wild-type Rrm2 polypeptide. Mutations found within a ubiquitin binding degron can be in succession, e.g., two or three amino acids in a row can be mutated. Alternatively, mutations found within a ubiquitin binding degron can be have wild-type amino acids in between. A mutation described herein can be an amino acid substitution, deletion, or insertion. It is contemplated herein that a mutation can be any amino acid change within the ubiquitin binding domain that results in at least decreased ubiquitination of Rrm2, increased stability of Rrm2, and/or increased dATP levels in the cell. Considerations for mutating a ubiquitination site while maintaining Rrm2 activity in terms of complex formation and ribonucleotide reductase activity with Rrm1 are discussed herein above. In some embodiments, the mutation is found near a ubiquitin binding degron, e.g., within 1-10 nucleotides of a ubiquitin binding degron, i.e., nucleotides not encoding a ubiquitin binding degron. In some embodiments, the mutation is found near a ubiquitin binding degron, e.g., within 1-10 amino acids of a ubiquitin binding degron, i.e., amino acids not encoding a ubiquitin binding degron.

In one embodiment, the mutation is selected from Table 1.

TABLE 1

| Rrm2 mutations (amino acid and its corresponding number in SEQ ID NO: 3 shown) | | | | | | |
|---|---|---|---|---|---|---|
| | Positon | | | | | |
| | 30 | 31 | 32 | 33 | 49 | 51 |
| Wild-type | K | E | N | T | R | I |
| Mutant | A | A | A | A | A | A |

In one embodiment, the isolated nucleic acid has a sequence of SEQ ID NOs: 16-20. In one embodiment, the isolated nucleic acid consists of or consists essentially of the sequence of SEQ ID NO: 16-20.

```
SEQ ID NO: 16 is an exemplary nucleic acid sequence for Rrm2 mutant 30AAA
ATGCTGAGTCTGAGGGTCCCACTGGCACCTATCACCGATCCACAGCAGCTGCAGCTGAGCCC

ACTGAAAGGCCTGAGTCTGGTCGATGCAGCGGCCACACCACCTGCACTGAGTGGCACTCGG

GTGCTGGCATCAAAGACCGCCCGGAGAATTTTCCAGGAGCCAACCGAACCCAAAACAAAGG

CCGCTGCACCTGGGGTCGAGGACGAACCACTGCTGAGAGAGAATCCCAGGCGCTTCGTGAT

TTTTCCTATCGAATACCACGATATTTGGCAGATGTATAAGAAAGCTGAGGCAAGTTTCTGGA

CAGCTGAGGAAGTGGACCTGAGCAAAGACATCCAGCACTGGGAATCCCTGAAGCCAGAGG

AAAGGTACTTCATTTCTCATGTGCTGGCATTCTTTGCCGCTAGTGACGGGATCGTGAACGAG

AATCTGGTCGAACGCTTTAGCCAGGAGGTGCAGATCACTGAAGCCCGATGCTTCTATGGATT

TCAGATTGCTATGGAGAACATCCATTCAGAAATGTACAGCCTGCTGATTGACACCTATATCA

AAGATCCTAAGGAGCGCGAGTTCCTGTTTAATGCCATTGAGACAATGCCATGTGTGAAGAA

AAAGGCAGACTGGGCTCTGCGATGGATCGGCGATAAGGAGGCTACTTACGGGGAAAGAGT

GGTCGCATTCGCAGCCGTGGAGGGAATTTTCTTTTCTGGCAGTTTCGCTTCCATCTTTTGGCT

GAAAAAGCGAGGCCTGATGCCTGGGCTGACCTTTTCCAACGAGCTGATTTCTCGCGACGAA

GGCCTGCACTGCGATTTCGCCTGTCTGATGTTTAAACACCTGGTGCATAAGCCCTCTGAGGA

ACGAGTCCGGGAGATCATTATCAACGCAGTGAGGATCGAGCAGGAGTTCCTGACAGAAGCC

CTGCCTGTCAAACTGATTGGCATGAATTGCACTCTGATGAAGCAGTACATCGAGTTTGTGGC

CGACAGGCTGATGCTGGAACTGGGATTCTCAAAGGTGTTTCGCGTCGAGAACCCATTCGATT

TTATGGAGAATATCAGCCTGGAAGGCAAAACAAACTTCTTTGAGAAGAGAGTCGGGGAATA

TCAGAGGATGGGCGTGATGAGCAGCCCCACTGAGAATAGCTTCACCCTGGACGCCGATTTTT

GA

SEQ ID NO: 17 is an exemplary nucleic acid sequence for Rrm2 mutant 30AAN
ATGCTGAGTCTGAGGGTCCCACTGGCACCTATCACCGATCCACAGCAGCTGCAGCTGAGCCC

ACTGAAAGGCCTGAGTCTGGTCGATGCAGCGAACACACCACCTGCACTGAGTGGCACTCGG

GTGCTGGCATCAAAGACCGCCCGGAGAATTTTCCAGGAGCCAACCGAACCCAAAACAAAGG
```

-continued

```
CCGCTGCACCTGGGGTCGAGGACGAACCACTGCTGAGAGAGAATCCCAGGCGCTTCGTGAT

TTTTCCTATCGAATACCACGATATTTGGCAGATGTATAAGAAAGCTGAGGCAAGTTTCTGGA

CAGCTGAGGAAGTGGACCTGAGCAAAGACATCCAGCACTGGGAATCCCTGAAGCCAGAGG

AAAGGTACTTCATTTCTCATGTGCTGGCATTCTTTGCCGCTAGTGACGGGATCGTGAACGAG

AATCTGGTCGAACGCTTTAGCCAGGAGGTGCAGATCACTGAAGCCCGATGCTTCTATGGATT

TCAGATTGCTATGGAGAACATCCATTCAGAAATGTACAGCCTGCTGATTGACACCTATATCA

AAGATCCTAAGGAGCGCGAGTTCCTGTTTAATGCCATTGAGACAATGCCATGTGTGAAGAA

AAAGGCAGACTGGGCTCTGCGATGGATCGGCGATAAGGAGGCTACTTACGGGGAAAGAGT

GGTCGCATTCGCAGCCGTGGAGGGAATTTTCTTTTCTGGCAGTTTCGCTTCCATCTTTTGGCT

GAAAAAGCGAGGCCTGATGCCTGGGCTGACCTTTTCCAACGAGCTGATTTCTCGCGACGAA

GGCCTGCACTGCGATTTCGCCTGTCTGATGTTTAAACACCTGGTGCATAAGCCCTCTGAGGA

ACGAGTCCGGGAGATCATTATCAACGCAGTGAGGATCGAGCAGGAGTTCCTGACAGAAGCC

CTGCCTGTCAAACTGATTGGCATGAATTGCACTCTGATGAAGCAGTACATCGAGTTTGTGGC

CGACAGGCTGATGCTGGAACTGGGATTCTCAAAGGTGTTTCGCGTCGAGAACCCATTCGATT

TTATGGAGAATATCAGCCTGGAAGGCAAAACAAACTTCTTTGAGAAGAGAGTCGGGGAATA

TCAGAGGATGGGCGTGATGAGCAGCCCCACTGAGAATAGCTTCACCCTGGACGCCGATTTTT

GA
```

SEQ ID NO: 18 is an exemplary nucleic acid sequence for Rrm2 mutant 33A
```
ATGCTGAGTCTGAGGGTCCCACTGGCACCTATCACCGATCCACAGCAGCTGCAGCTGAGCCC

ACTGAAAGGCCTGAGTCTGGTCGATAAAGAGAACGCACCACCTGCACTGAGTGGCACTCGG

GTGCTGGCATCAAAGACCGCCCGGAGAATTTTCCAGGAGCCAACCGAACCCAAAACAAAGG

CCGCTGCACCTGGGGTCGAGGACGAACCACTGCTGAGAGAGAATCCCAGGCGCTTCGTGAT

TTTTCCTATCGAATACCACGATATTTGGCAGATGTATAAGAAAGCTGAGGCAAGTTTCTGGA

CAGCTGAGGAAGTGGACCTGAGCAAAGACATCCAGCACTGGGAATCCCTGAAGCCAGAGG

AAAGGTACTTCATTTCTCATGTGCTGGCATTCTTTGCCGCTAGTGACGGGATCGTGAACGAG

AATCTGGTCGAACGCTTTAGCCAGGAGGTGCAGATCACTGAAGCCCGATGCTTCTATGGATT

TCAGATTGCTATGGAGAACATCCATTCAGAAATGTACAGCCTGCTGATTGACACCTATATCA

AAGATCCTAAGGAGCGCGAGTTCCTGTTTAATGCCATTGAGACAATGCCATGTGTGAAGAA

AAAGGCAGACTGGGCTCTGCGATGGATCGGCGATAAGGAGGCTACTTACGGGGAAAGAGT

GGTCGCATTCGCAGCCGTGGAGGGAATTTTCTTTTCTGGCAGTTTCGCTTCCATCTTTTGGCT

GAAAAAGCGAGGCCTGATGCCTGGGCTGACCTTTTCCAACGAGCTGATTTCTCGCGACGAA

GGCCTGCACTGCGATTTCGCCTGTCTGATGTTTAAACACCTGGTGCATAAGCCCTCTGAGGA

ACGAGTCCGGGAGATCATTATCAACGCAGTGAGGATCGAGCAGGAGTTCCTGACAGAAGCC

CTGCCTGTCAAACTGATTGGCATGAATTGCACTCTGATGAAGCAGTACATCGAGTTTGTGGC

CGACAGGCTGATGCTGGAACTGGGATTCTCAAAGGTGTTTCGCGTCGAGAACCCATTCGATT

TTATGGAGAATATCAGCCTGGAAGGCAAAACAAACTTCTTTGAGAAGAGAGTCGGGGAATA

TCAGAGGATGGGCGTGATGAGCAGCCCCACTGAGAATAGCTTCACCCTGGACGCCGATTTTT

GA
```

SEQ ID NO: 19 is an exemplary nucleic acid sequence for Rrm2 mutant 49ARA
```
ATGCTGAGTCTGAGGGTCCCACTGGCACCTATCACCGATCCACAGCAGCTGCAGCTGAGCCC

ACTGAAAGGCCTGAGTCTGGTCGATAAAGAGAACACACCACCTGCACTGAGTGGCACTCGG

GTGCTGGCATCAAAGACCGCCCGCGAGAGCTTTCCAGGAGCCAACCGAACCCAAAACAAAGG
```

```
CCGCTGCACCTGGGGTCGAGGACGAACCACTGCTGAGAGAGAATCCCAGGCGCTTCGTGAT

TTTTCCTATCGAATACCACGATATTTGGCAGATGTATAAGAAAGCTGAGGCAAGTTTCTGGA

CAGCTGAGGAAGTGGACCTGAGCAAAGACATCCAGCACTGGGAATCCCTGAAGCCAGAGG

AAAGGTACTTCATTTCTCATGTGCTGGCATTCTTTGCCGCTAGTGACGGGATCGTGAACGAG

AATCTGGTCGAACGCTTTAGCCAGGAGGTGCAGATCACTGAAGCCCGATGCTTCTATGGATT

TCAGATTGCTATGGAGAACATCCATTCAGAAATGTACAGCCTGCTGATTGACACCTATATCA

AAGATCCTAAGGAGCGCGAGTTCCTGTTTAATGCCATTGAGACAATGCCATGTGTGAAGAA

AAAGGCAGACTGGGCTCTGCGATGGATCGGCGATAAGGAGGCTACTTACGGGGAAAGAGT

GGTCGCATTCGCAGCCGTGGAGGGAATTTTCTTTTCTGGCAGTTTCGCTTCCATCTTTTGGCT

GAAAAAGCGAGGCCTGATGCCTGGGCTGACCTTTTCCAACGAGCTGATTTCTCGCGACGAA

GGCCTGCACTGCGATTTCGCCTGTCTGATGTTTAAACACCTGGTGCATAAGCCCTCTGAGGA

ACGAGTCCGGGAGATCATTATCAACGCAGTGAGGATCGAGCAGGAGTTCCTGACAGAAGCC

CTGCCTGTCAAACTGATTGGCATGAATTGCACTCTGATGAAGCAGTACATCGAGTTTGTGGC

CGACAGGCTGATGCTGGAACTGGATTCTCAAAGGTGTTTCGCGTCGAGAACCCATTCGATT

TTATGGAGAATATCAGCCTGGAAGGCAAAACAAACTTCTTTGAGAAGAGAGTCGGGGAATA

TCAGAGGATGGGCGTGATGAGCAGCCCCACTGAGAATAGCTTCACCCTGGACGCCGATTTTT

GA

SEQ ID NO: 20 is an exemplary nucleic acid sequence for Rrm2 mutant 30AAA/49ARA
ATGCTGAGTCTGAGGGTCCCACTGGCACCTATCACCGATCCACAGCAGCTGCAGCTGAGCCC

ACTGAAAGGCCTGAGTCTGGTCGATGCAGCGGCCACACCACCTGCACTGAGTGGCACTCGG

GTGCTGGCATCAAAGACCGCCGCGAGAGCTTTCCAGGAGCCAACCGAACCCAAAACAAAGG

CCGCTGCACCTGGGGTCGAGGACGAACCACTGCTGAGAGAGAATCCCAGGCGCTTCGTGAT

TTTTCCTATCGAATACCACGATATTTGGCAGATGTATAAGAAAGCTGAGGCAAGTTTCTGGA

CAGCTGAGGAAGTGGACCTGAGCAAAGACATCCAGCACTGGGAATCCCTGAAGCCAGAGG

AAAGGTACTTCATTTCTCATGTGCTGGCATTCTTTGCCGCTAGTGACGGGATCGTGAACGAG

AATCTGGTCGAACGCTTTAGCCAGGAGGTGCAGATCACTGAAGCCCGATGCTTCTATGGATT

TCAGATTGCTATGGAGAACATCCATTCAGAAATGTACAGCCTGCTGATTGACACCTATATCA

AAGATCCTAAGGAGCGCGAGTTCCTGTTTAATGCCATTGAGACAATGCCATGTGTGAAGAA

AAAGGCAGACTGGGCTCTGCGATGGATCGGCGATAAGGAGGCTACTTACGGGGAAAGAGT

GGTCGCATTCGCAGCCGTGGAGGGAATTTTCTTTTCTGGCAGTTTCGCTTCCATCTTTTGGCT

GAAAAAGCGAGGCCTGATGCCTGGGCTGACCTTTTCCAACGAGCTGATTTCTCGCGACGAA

GGCCTGCACTGCGATTTCGCCTGTCTGATGTTTAAACACCTGGTGCATAAGCCCTCTGAGGA

ACGAGTCCGGGAGATCATTATCAACGCAGTGAGGATCGAGCAGGAGTTCCTGACAGAAGCC

CTGCCTGTCAAACTGATTGGCATGAATTGCACTCTGATGAAGCAGTACATCGAGTTTGTGGC

CGACAGGCTGATGCTGGAACTGGATTCTCAAAGGTGTTTCGCGTCGAGAACCCATTCGATT

TTATGGAGAATATCAGCCTGGAAGGCAAAACAAACTTCTTTGAGAAGAGAGTCGGGGAATA

TCAGAGGATGGGCGTGATGAGCAGCCCCACTGAGAATAGCTTCACCCTGGACGCCGATTTTT

GA
```

In one embodiment, an isolated nucleic acid comprises, consists of, or consists essentially of a sequence at least 90%, at least 91%, at least 92%, at least 93%, at least 94%, at least 95%, at least 96%, at least 97%, at least 98%, at least 99%, or more, identical to one of SEQ ID NO: 16-20, and retains at least 50% of the function of one of SEQ ID NO: 16-20, e.g., complex formation with Rrm1 and increasing the cellular level of dATP.

In one embodiment, the isolated polypeptide has a sequence of SEQ ID NOs: 21-25. In one embodiment, the isolated polypeptide consists of or consists essentially of a polypeptide having the sequence of SEQ ID NO: 21-25.

```
SEQ ID NO: 21 is an exemplary amino acid sequence
for Rrm2 mutant 30AAA
MLSLRVPLAPITDPQQLQLSPLKGLSLVDAAATPPALSGTRVLASKTARR

IFQEPTEPKTKAAAPGVEDEPLLRENPRRFVIFPIEYHDIWQMYKKAEAS

FWTAEEVDLSKDIQHWESLKPEERYFISHVLAFFAASDGIVNENLVERFS

QEVQITEARCFYGFQIAMENIHSEMYSLLIDTYIKDPKEREFLFNAIETM

PCVKKKADWALRWIGDKEATYGERVVAFAAVEGIFFSGSFASIFWLKKRG

LMPGLTFSNELISRDEGLHCDFACLMFKHLVHKPSEERVREIINAVRIE

QEFLTEALPVKLIGMNCTLMKQYIEFVADRLMLELGFSKVFRVENPFDFM

ENISLEGKTNFFEKRVGEYQRMGVMSSPTENSFTLDADF

SEQ ID NO: 22 is an exemplary amino acid sequence
for Rrm2 mutant 30AAN
MLSLRVPLAPITDPQQLQLSPLKGLSLVDAANTPPALSGTRVLASKTARR

IFQEPTEPKTKAAAPGVEDEPLLRENPRRFVIFPIEYHDIWQMYKKAEAS

FWTAEEVDLSKDIQHWESLKPEERYFISHVLAFFAASDGIVNENLVERFS

QEVQITEARCFYGFQIAMENIHSEMYSLLIDTYIKDPKEREFLFNAIETM

PCVKKKADWALRWIGDKEATYGERVVAFAAVEGIFFSGSFASIFWLKKRG

LMPGLTFSNELISRDEGLHCDFACLMFKHLVHKPSEERVREIINAVRIE

QEFLTEALPVKLIGMNCTLMKQYIEFVADRLMLELGFSKVFRVENPFDFM

ENISLEGKTNFFEKRVGEYQRMGVMSSPTENSFTLDADF

SEQ ID NO: 23 is an exemplary amino acid sequence
for Rrm2 mutant 33A
MLSLRVPLAPITDPQQLQLSPLKGLSLVDKENAPPALSGTRVLASKTARR

IFQEPTEPKTKAAAPGVEDEPLLRENPRRFVIFPIEYHDIWQMYKKAEAS

FWTAEEVDLSKDIQHWESLKPEERYFISHVLAFFAASDGIVNENLVERFS

QEVQITEARCFYGFQIAMENIHSEMYSLLIDTYIKDPKEREFLFNAIETM

PCVKKKADWALRWIGDKEATYGERVVAFAAVEGIFFSGSFASIFWLKKRG

LMPGLTFSNELISRDEGLHCDFACLMFKHLVHKPSEERVREIINAVRIE

QEFLTEALPVKLIGMNCTLMKQYIEFVADRLMLELGFSKVFRVENPFDFM

ENISLEGKTNFFEKRVGEYQRMGVMSSPTENSFTLDADF

SEQ ID NO: 24 is an exemplary amino acid sequence
for Rrm2 mutant 49ARA
MLSLRVPLAPITDPQQLQLSPLKGLSLVDKENTPPALSGTRVLASKTAAR

AFQEPTEPKTKAAAPGVEDEPLLRENPRRFVIFPIEYHDIWQMYKKAEAS

FWTAEEVDLSKDIQHWESLKPEERYFISHVLAFFAASDGIVNENLVERFS

QEVQITEARCFYGFQIAMENIHSEMYSLLIDTYIKDPKEREFLFNAIETM

PCVKKKADWALRWIGDKEATYGERVVAFAAVEGIFFSGSFASIFWLKKRG

LMPGLTFSNELISRDEGLHCDFACLMFKHLVHKPSEERVREIINAVRIE

QEFLTEALPVKLIGMNCTLMKQYIEFVADRLMLELGFSKVFRVENPFDFM

ENISLEGKTNFFEKRVGEYQRMGVMSSPTENSFTLDADF

SEQ ID NO: 25 is an exemplary amino acid sequence
for Rrm2 mutant 30AAA/49ARA
MLSLRVPLAPITDPQQLQLSPLKGLSLVDAAATPPALSGTRVLASKTAAR

AFQEPTEPKTKAAAPGVEDEPLLRENPRRFVIFPIEYHDIWQMYKKAEAS

FWTAEEVDLSKDIQHWESLKPEERYFISHVLAFFAASDGIVNENLVERFS

QEVQITEARCFYGFQIAMENIHSEMYSLLIDTYIKDPKEREFLFNAIETM

PCVKKKADWALRWIGDKEATYGERVVAFAAVEGIFFSGSFASIFWLKKRG

LMPGLTFSNELISRDEGLHCDFACLMFKHLVHKPSEERVREIINAVRIE

QEFLTEALPVKLIGMNCTLMKQYIEFVADRLMLELGFSKVFRVENPFDFM

ENISLEGKTNFFEKRVGEYQRMGVMSSPTENSFTLDADF
```

In one embodiment, an isolated polypeptide comprises, consists of, or consists essentially of polypeptide having a sequence having at least 90%, at least 91%, at least 92%, at least 93%, at least 94%, at least 95%, at least 96%, at least 97%, at least 98%, at least 99%, or more, identical to one of SEQ ID NO: 21-25, and retains as least 50% of the function of one of SEQ ID NO: 21-25, e.g., complex formation with Rrm1 and increasing the cellular level of dATP.

Ubiquitin-Mediated Degradation

The ubiquitin-mediated degradation pathway promotes selective, controlled degradation of intracellular proteins in eukaryotic cells. One major function of the ubiquitin-mediated system is to control the half-lives of cellular proteins. The half-life of different proteins can range from, e.g., a few minutes to days or more, and can vary considerably depending on the type of protein, e.g., structural protein vs enzyme or regulatory protein, cell type, nutritional and environmental conditions, as well as the stage of the cell-cycle.

Proteins that undergo selective degradation, presumably through the actions of a ubiquitin-dependent proteasome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins, also known as ubiquitin ligases.

Depending on the ubiquitin-conjugating enzyme and the nature of the substrate, specific lysine residues of ubiquitin are used as acceptor sites for further ubiquitinations. This can lead to either a linear multiubiquitin chain (when a single lysine residue of ubiquitin is used) or multi-ubiquitin "trees" (when more than one lysine reside of ubiquitin is used). Although the attachment of a single ubiquitin moiety to a substrate can be sufficient for targeted degradation, multi-ubiquitination appears to be required in most cases.

Amino acids that are likely to be ubiquitinated (i.e., a ubiquitination site) can be identified, e.g., using ubiquitination site prediction software. Exemplary software includes UbPred: predictor of protein ubiquitination sites (found on the world wide web at www.ubpred.org), UbiSite (found on the world wide web at csb.cse.yzu.edu.tw/UbiSite/), BDM Pub (e.g., found on the world wide web at bdmpub.biocuckoo.org/). Methods for identifying ubiquitination sites are further reviewed in, e.g., He F., et al. BMC Systems Biol. 2018, 12(Supp 6):109; Radivojac, P., et al. Proteins. 2010 Feb. 1; 78(2): 365-380; and Yadav, S., et al. Advances in Fuzzy Systems. Volume 2018, Article ID 5125103, 10 pages; the contents of which are incorporated herein by reference in their entireties.

In one embodiment, mutations placed in the ubiquitin binding degron prevents, inhibits, or decreases conjugation of ubiquitin to Rrm2. In one embodiment, the mutations in the Rrm2 ubiquitin binding degron nucleotide sequence results in decreased ubiquitination levels of the encoded Rrm2 protein. In one embodiment, the level of ubiquitin of the encoded Rrm2 protein is decreased at least 10%, at least 20%, at least 30%, at least 40%, at least 50%, at least 60%, at least 70%, at least 80%, at least 90%, at least 95%, at least 99% or more as compared to ubiquitin level of a wild-type Rrm2 protein at that site. Assays for detecting the level of ubiquitination of a protein are known in the art, and include, for example, co-immunoprecipitation of the protein of interest under denaturing conditions and SDS-PAGE gel and western blotting techniques with an anti-ubiquitin antibody to visualize the level of ubiquitin on the protein of interest. Additional assays for determining the level of ubiquitination of a protein include Ubi-Detect protein ubiquitination detection kit (e.g., available from R&D Systems).

Mutations in the Rrm2 ubiquitin binding degron that decrease the level of ubiquitination result in an increased stability of the Rrm2 protein, as it is no longer targeted by the ubiquitin mediated degradation system. In one embodiment, the mutations in the Rrm2 ubiquitin binding degron nucleotide sequence results in increased stability of the of the encoded Rrm2 protein (i.e., an increased half-life of the protein). In one embodiment, the level of stability of the encoded Rrm2 protein is increased at least 10%, at least 20%, at least 30%, at least 40%, at least 50%, at least 60%, at least 70%, at least 80%, at least 90%, at least 95%, at least 99% or more, or at least 1-fold, at least 2-fold, at least 3-fold, at least 4-fold, at least 5-fold, at least 6-fold, at least 7-fold, at least 8-fold, at least 9-fold, at least 10-fold or more as compared to the stability level of a wild-type Rrm2 protein. Assays for detecting the stability of a protein are known in the art, and include, treating a cell lysate or an in vitro system having the protein of interest and components of the ubiquitin mediated degradation system with cyclohexamide to halt protein translation and measuring the level of the protein of interest over time (e.g., in a time course) via Western blotting. Alternatively, protein stability can be measured using a standard pulse-chase experiment.

2-deoxy-ATP (2-deoxyadenosine; dATP)

Deoxyadenosine is a derivative of the nucleoside adenosine. It is composed of adenine covalently attached to a deoxyribose moiety via an N9-glycosidic bond. Deoxyribose differs from ribose by the absence of oxygen in the 3' position of its ribose ring. Deoxyadenosine is a critical component of DNA; deoxyadenosine is the DNA nucleoside A, which pairs with deoxythymidine (T) in double-stranded DNA.

In one embodiment, cellular expression of an isolated rrm2 nucleic acid or an Rrm2 polypeptide encoded by the nucleic acid, or a composition thereof, increases dATP in the cell. For example, cellular expression of an isolated rrm2 nucleic acid or an Rrm2 polypeptide encoded by it, or a composition thereof increases intracellular dATP levels at least 10%, at least 20%, at least 30%, at least 40%, at least 50%, at least 60%, at least 70%, at least 80%, at least 90%, at least 95%, at least 99% or more, or at least 1-fold, at least 2-fold, at least 3-fold, at least 4-fold, at least 5-fold, at least 6-fold, at least 7-fold, at least 8-fold, at least 9-fold, at least 10-fold or more as compared to expression of wild-type Rrm2. Deoxyadenosine levels in a cell, such as a cell expressing an Rrm2 mutant polypeptide as described herein can be measured via e.g., HPLC or mass spectrometry using standard protocols.

In one embodiment, expression of an Rrm2 mutant as described herein can, on its own, provide an increase in dATP level; that is, increasing the stability of the normally unstable Rrm2 subunit of the Rrm1/Rrm2 RNR complex can provide an increase in RNR activity. Alternatively, expression of both Rrm1 and an Rrm2 mutant can be provided, either from two separate vectors or from a single vector encoding both factors. When both Rrm1 and a mutant Rrm2 as described herein are used, the additional expression of the Rrm1 can permit enhancement in RNR activity beyond that achievable by providing the stabilized Rrm2 mutant alone.

Vectors

Provided herein are vectors comprising any of the isolated nucleic acids described herein that encode Rrm2 mutants with increased intracellular half-life. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

In one embodiment, a vector is a viral vector. As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Exemplary viral vectors for delivery of a gene or gene product to a subject, include, but are not limited to an adeno associated virus (AAV), a lentivirus (LV), a herpes simplex virus (HSV), an adeno virus (AV), or a pox virus (PV). Protocols for producing recombinant viral vectors and for using viral vectors for nucleic acid delivery can be found, e.g., in Current Protocols in Molecular Biology, Ausubel, F. M. et al. (eds.) Greene Publishing Associates, (1989) and other standard laboratory manuals (e.g., Vectors for Gene Therapy. In: Current Protocols in Human Genetics. John Wiley and Sons, Inc.: 1997). Further, production of AAV vectors is further described, e.g., in U.S. Pat. No. 9,441,206, the contents of which is incorporated herein by reference in its entirety.

By "recombinant vector" is meant a vector that includes a heterologous nucleic acid sequence, or "transgene" that is capable of expression in vivo. It should be understood that the vectors described herein can, in some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

While it is generally considered that therapeutic approaches using Rrm2 mutant polypeptides as described herein will express the Rrm2 polypeptide in a cell, e.g., a cardiac cell, it is contemplated that the Rrm2 polypeptide mutants described herein can alternatively be used in purified protein form. Thus, in some embodiments, a vector drives polypeptide (i.e., protein) expression in insect cells using baculovirus expression vectors, which together provide very efficient expression of recombinant proteins, which can be isolated for direct use. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. Virology 170: 31-39).

In one embodiment, an isolated nucleic acid as described herein is operatively linked to a promotor for expression of the isolated nucleic acid. Exemplary promoters that can be used in the present technology include, but are not limited to, constitutive promoters, repressible promoters, and/or inducible promoters, some non-limiting examples of which include viral promoters (e.g., CMV, SV40), tissue specific promoters (e.g., muscle MCK), heart (e.g., NSE), eye (e.g., MSK) and synthetic promoters (SP1 elements) and the chicken beta actin promoter (CB or CBA).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195), and are further described in, e.g., U.S. Pat. Nos. 8,187,836; 8,455,219; 8,980,626; 7,384,776; and 6,451,539; the contents of which are incorporated herein by reference in their entireties. When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989; and Muller, D., et al. (2006) Microbial Cell Factories.

In some embodiments, the recombinant mammalian expression vector is capable of directing expression of the synthetic nucleic acid preferentially in a particular cell type (e.g., tissue-specific regulatory elements are used to express the nucleic acid in, for example, a hematopoietic cell). Tissue-specific regulatory elements are known in the art. Non-limiting examples of suitable cardiac tissue-specific promoters include the NCX1 promoter (e.g., as described in Nicholas S B., et al. Am J Physiol. 1998), the MLC-2v (e.g., as described Griscelli, F., et al. C R Acad Sci III. 1997 February; 320(2):103-12); cardiac troponin-I proximal promoter (TNN13) (e.g., as described in Gallo, P., et al. Gene Therapy. 15, pages 161-170 (2008); and the aMHC promoter. All citations provided herein are incorporated herein by reference in their entireties.

In one embodiment, the synthetic nucleic acid molecules described herein are introduced to a cell via a non-viral method. Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). In one embodiment, human IPS-derived cardiomyocytes are modified in vitro to express an Rrm2 mutant as described herein before being introduced to or transplanted into cardiac tissue in vivo.

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Compositions

Various aspects described herein provide a composition comprising, consisting of, or consisting essentially of any of the isolated nucleic acids, vectors, polypeptides, or RNR complexes described herein.

One aspect provided herein is a pharmaceutical composition comprising, consisting of, or consisting essentially of any of the isolated nucleic acids, vectors, polypeptides, or RNR complexes described herein. As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier in which the active ingredient would not be found to occur in nature.

Pharmaceutically acceptable or physiologically tolerable materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid, including, but not limited to, e.g., lyophilized, forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present technology can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

Method of Treating Cardiac Disease or Disorder

One aspect provided herein is a method of administering a composition or pharmaceutical composition described herein to a subject suffering from a cardiac disease or disorder, e.g., a disease or disorder characterized by insufficient cardiac function or defects in the heart structure. Exemplary cardiac diseases or disorders include congestive heart failure, cardiomyopathy, myocardial infarction, cardiac ischemia, vascular disease, acquired heart disease, congenital heart disease, atherosclerosis, cardiomyopathy, dysfunctional conduction systems, dysfunctional coronary arteries, and pulmonary hypertension. In some embodiments, the disease is selected from the group consisting of congestive heart failure, coronary artery disease, myocardial infarction, myocardial ischemia, atherosclerosis, cardiomyopathy, idiopathic cardiomyopathy, cardiac arrhythmias, muscular dystrophy, muscle mass abnormality, muscle degeneration, infective myocarditis, drug- or toxin-induced muscle abnormalities, hypersensitivity myocarditis, an autoimmune endocarditis and congenital heart disease. In one embodiment, the compositions and methods as disclosed herein are useful for treatment of a disease or disorder which is myocardial infarction or myocardial ischemia.

Other aspects relate to the use of a therapeutic agent as described herein (e.g., an isolated nucleic acid encoding an Rrm2 polypeptide mutant, a vector encoding an Rrm2 polypeptide mutant, a vector encoding Rrm1 and an Rrm2 polypeptide mutant, a cell comprising sequence encoding any of these, an Rrm2 polypeptide mutant, or a protein complex consisting of Rrm1 and an Rrm2 polypeptide mutant) in a method for the treatment of a cardiovascular disease or disorder in a subject. Other aspects of the present technology relate to a composition or pharmaceutical composition comprising said therapeutic agent, for use in the treatment of a cardiac disease or disorder. In alternative embodiments, a population of cardiac cells, e.g., a population of cardiomyocytes, or cardiomyocyte precursor cells (e.g., cardiac stem cells) can be contacted with a therapeutic agent or a composition thereof in vitro, in vivo or ex vivo, and in some embodiments, where the contact occurs in vitro or ex vivo, the population of cardiac cells, e.g., cardiomyocytes can be transplanted into a subject for the treatment and/or prevention of cardiac diseases, or for the treatment of existing cardiac muscle which is damaged by disease or injury, e.g., induced by a myocardial infarction.

In alternative embodiments, the present technology provides for methods to treat a cardiovascular disease or disorder in a subject comprising administering to the subject a composition comprising a population of cardiac cells, e.g., population of cardiac stem cells, ventricular cardiac stem cells or cardiac cells differentiated from human stem cells, e.g., IPS cells, where the population of cells comprises sequences encoding an Rrm2 mutant polypeptide as described herein, alone or together with an Rrm1 polypeptide. In some embodiments, the iPS cell is an autologous iPS cell e.g., an iPS cell which was reprogrammed from a somatic cell obtained from a subject to which the pharmaceutical composition is being administered. In some embodiments, a cardiac cell is a population of primordial or cardiac cell precursors, or their progeny, as disclosed in International Patent Applications, WO/2008/054819, WO2010/144678, WO2010/042856, and U.S. Patent Applications 2010/0166714, US2011/0033430, US2010/021713 and US2011/0003327, which are incorporated herein in their entirety by reference. In some embodiments, a cell population is a Isl1+ primordial cell, or progeny thereof as disclosed in WO2010/144678.

With reference to the treatment of, for example, a cardiovascular condition or disease in a subject, the term "therapeutically effective amount" refers to the amount of a therapeutic agent that is safe and sufficient to treat, prevent or delay the development of a cardiovascular disease or disorder. The amount can thus cure or cause the cardiovascular disease or disorder to go into remission, slow the course of cardiovascular disease progression, reduce or inhibit a symptom of a cardiovascular disease or disorder, slow or inhibit the establishment of secondary symptoms of a cardiovascular disease or disorder or inhibit the development of a secondary symptom of a cardiovascular disease or disorder. The effective amount for the treatment of the cardiovascular disease or disorder depends on the type of cardiovascular disease to be treated, the severity of the symptoms, the subject being treated, the age and general condition of the subject, the mode of administration and so forth. Thus, it is not possible to specify any exact "effective amount." However, for any given case, an appropriate "effective amount" can be determined by one of ordinary skill in the art using only routine experimentation.

Administering

As used herein, the terms "administering," "introducing" and "transplanting" are used interchangeably and refer to the placement of a pharmaceutical composition comprising a therapeutic agent described herein (e.g., an isolated nucleic acid encoding Rrm2 polypeptide mutant, an Rrm2 polypeptide mutant, or a protein complex consisting of Rrm1 and an Rrm2 polypeptide mutant), or a composition comprising a population of cells and therapeutic agent, or a composition comprising a population cells that have previously been contacted with a therapeutic agent as described herein, into a subject by a method or route which results in at least partial localization of any of the compositions, at a desired site or tissue location, e.g., cardiac tissue. In various embodiment, the terms "administering," "introducing" and "transplanting" are used interchangeably and refer to the placement of a pharmaceutical composition comprising a therapeutic agent, or a composition comprising a population of cardiac cells and a therapeutic agent, or a composition comprising a population of cardiomyocytes that have been previously contacted by a therapeutic agent as described herein, into a subject by a method or route which results in at least partial localization of the pharmaceutical composition, at a desired cardiac site or cardiac tissue location. In some embodiments, the pharmaceutical composition comprising a therapeutic agent can be administered by any appropriate route which results in effective treatment in the subject, i.e. administration results in delivery to a desired location or tissue in the subject where at least a portion of the therapeutic agent is located at a desired target tissue, e.g., cardiac tissue, or target cell (e.g., cardiac cell, such as a cardiomyocyte) location.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrases "systemic administration," "administered systemically", "peripheral administration" and "administered peripherally" as used herein mean the administration of pharmaceutical compositions comprising a therapeutic agent described herein other than directly into a target tissue or organ, such that it enters the animal's system and, thus, is subject to metabolism and other like processes.

These pharmaceutical preparations are a further object of the technology. Usually the amount of active ingredient (polypeptide, nucleic acid encoding polypeptide, vector, etc.) is between 0.1-95% by weight of the preparation, preferably between 0.2-20% by weight in preparations for parenteral use.

Combination Therapies

While it is contemplated herein that a pharmaceutical composition comprising a therapeutic agent described herein (e.g., an isolated nucleic acid encoding an Rrm2 polypeptide mutant, an Rrm2 polypeptide mutant, or a protein complex consisting of Rrm1 and an Rrm2 polypeptide mutant), or a composition comprising a population of cells and therapeutic agent, or a composition comprising a population of cells that have previously been contacted with a therapeutic agent as described herein can be administered as a monotherapy to a subject, combination therapy can be used to treat a cardiac disease or disorder in a subject. In various embodiments, the subject is further administered any other approved therapy for a cardiac disease or disorder. Such therapies include, but are not limited to ACE Inhibitors; Angiotension II Receptor Blockers; Antiarrhythmics; Antiplatelet Drugs; Aspirin Therapy; Beta-Blocker Therapy; Calcium Channel Blocker Drugs; Clot Buster Drugs (e.g., thrombolytic therapy); Digoxin; Diuretics; Nitrates; or Blood Thinners (e.g., Warfarin). Therapies can further include lifestyle changes (e.g., weight loss, increased exercise; change in diet (e.g., reduction in red meat); surgical procedures (e.g., coronary angioplasty, artificial heart valve surgery, atheretomy, cardiomyoplasty; limited access coronary artery surgery; transmyocardial revascularization; or coronary artery bypass graft surgery (CABG)); or placement of a therapeutic device (e.g., a stent).

Administered "in combination," as used herein, means that two (or more) different treatments are delivered to the subject during the course of the subject's affliction with the disorder, e.g., the two or more treatments are delivered after the subject has been diagnosed with a cardiac disorder or disease and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The therapeutic agents described herein and the at least one additional therapy can be administered simultaneously, in the same or in separate compositions, or sequentially. For sequential administration, the therapeutic agent described herein can be administered first, and the additional therapy can be administered second, or the order of administration can be reversed. The therapeutic agent and/or other therapy, e.g., procedures or modalities, can be administered during periods of active disorder, or during a period of remission or less active disease. The therapeutic agent can be administered before another treatment, concurrently with the treatment, post-treatment, or during remission of the disorder. It is understood that the therapeutic agent and an additional therapy are to be administered using appropriate means known in the art, and that these means can be the same or different. For example, a composition comprising cardiomyocytes that have previously been contacted by a therapeutic agent described herein will be administered locally to the cardiac tissue, and Warfarin will be administered orally for systemic administration.

Dosage

In some embodiments, a composition as described herein is administered in unit dosage form. "Unit dosage form" as the term is used herein refers to a dosage suitable for one administration. By way of example a unit dosage form can be an amount of therapeutic disposed in a delivery device, e.g., a syringe, catheter, e.g., a cardiac catheter, or intravenous drip bag. In one embodiment, a unit dosage form is administered in a single administration. In another, embodiment more than one unit dosage form can be administered simultaneously.

The dosage of the therapeutic agent as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytotoxic effects. The dosage can also be adjusted by the individual physician in the event of any complication.

The dosage range depends upon the potency, and includes amounts large enough to produce the desired effect, e.g., an improvement in cardiac function. Generally, the dosage will vary with the type of therapeutic agent given (e.g., an isolated nucleic acid encoding an Rrm2 polypeptide mutant, an Rrm2 polypeptide mutant, or a protein complex consisting of Rrm1 and an Rrm2 polypeptide mutant; or a composition comprising a population of cells and therapeutic agent; or a composition comprising a population cells that have previously been contacted with a therapeutic agent as described herein) and with the age, sex, and condition of the patient. Dosages for nucleic acids and vectors can be in the nanograms to micrograms range (e.g., 10 ng, 100 ng, 1 microgram, 10 micrograms, 100 micrograms, 1 milligram or more), particularly when administered directly, e.g., to cardiac tissue. Dosages for cells can be in the range of 1000 cells to $10^4$ cells, $5 \times 10^4$ cells, $10^5$ cells, $5 \times 10^5$ cells, $10^6$ cells, $5 \times 10^6$ cells, $10^7$ cells, $5 \times 10^7$ cells, $10^8$ cells, $5 \times 10^8$ cells, $10^9$ cells, $5 \times 10^9$ cells, $10^{10}$ cells or more, including ranges between these dosages (e.g., 1000-5,000 cells, 1000-10,000 cells, 1000-100,000 cells, 1000-$10^6$ cells, 1000-$10^7$ cells, 1000-$10^8$ cells, 1000-$10^9$ cells, 1000-$10^{10}$ cells, $10^6$ to $10^{10}$ cells, $10^6$-$10^9$ cells, $10^6$-$10^8$ cells, $10^6$-$10^7$ cells and all integer values within those ranges. If necessary, cell compositions can also be administered multiple times at these dosages. The cells can be administered by using injection or infusion techniques that are commonly known in the field (see, e.g., Rosenberg et al., New Eng. J. of Med. 319:1676, 1988). For injection or implantation, cells can be suspended in a biocompatible gel or polymer, or impregnated within a matrix or scaffold, e.g., to slow the rate of diffusion or wash-out of the cells from the site of administration.

Efficacy

The efficacy of treatment can be judged by an ordinarily skilled practitioner. For example, efficacy can be assessed by determining whether a composition or formulation leads to a decrease of at least one symptom of the disease or disorder as disclosed herein, e.g., cardiovascular disease. For example, any of increased heart ejection fraction, decreased rate of heart failure, decreased infarct size, decreased associated morbidity (pulmonary edema, renal failure, arrhythmias) improved exercise tolerance or other quality of life measures, and decreased mortality indicates effective treatment. Increased or efficient engraftment of transplanted cells (i.e., greater than or equal to 2%, greater than or equal to 4%, greater than or equal to 5% or more) including, but not limited to autologous cells bearing a nucleic acid or vector as described herein also indicates effective treatment. In embodiments where the compositions are used for the treatment of a cardiovascular disease or disorder, the efficacy of the composition can be judged using an experimental animal model of cardiovascular disease, e.g., animal models of ischemia-reperfusion injury (Headrick J P, Am J Physiol Heart circ Physiol 285; H1797; 2003) and animal models acute myocardial infarction. (Yang Z, Am J Physiol Heart Circ. Physiol 282:H949:2002; Guo Y, J Mol Cell Cardiol 33; 825-830, 2001).

As used herein, the term "treating" when used in reference to a treatment of a cardiovascular disease or disorder is used to refer to the reduction of a symptom and/or a biochemical marker of a cardiovascular disease or disorder, for example a reduction in at least one biochemical marker of a cardiovascular disease by at least about 10% would be considered an effective treatment. Examples of such biochemical markers of cardiovascular disease include a reduction of, for example, creatine phosphokinase (CPK), aspartate aminotransferase (AST), lactate dehydrogenase (LDH) in the blood, and/or a decrease in a symptom of cardiovascular disease and/or an improvement in blood flow and cardiac function as determined by someone of ordinary skill in the art as measured by electrocardiogram (ECG or EKG), or echocardiogram (heart ultrasound), Doppler ultrasound and nuclear medicine imaging. A reduction in a symptom of a cardiovascular disease by at least about 10% would also be considered effective treatment by the methods as disclosed herein. As alternative examples, a reduction in a symptom of cardiovascular disease, for example a reduction of at least one of the following; dyspnea, chest pain, palpitations, dizziness, syncope, edema, cyanosis etc. by at least about 10% or a cessation of such systems, or a reduction in the size one such symptom of a cardiovascular disease by at least about 10% would also be considered as affective treatments by the methods as disclosed herein. In some embodiments, it is preferred, but not required that the therapeutic agent actually eliminate the cardiovascular disease or disorder, rather just reduce a symptom to a manageable extent.

Subjects in need of treatment by the methods as disclosed herein can be identified by any method to diagnose myocardial infarction (commonly referred to as a heart attack). Methods of diagnosing these conditions are well known by persons of ordinary skill in the art. By way of non-limiting example, myocardial infarction can be diagnosed by (i) blood tests to detect levels of creatine phosphokinase (CPK), aspartate aminotransferase (AST), lactate dehydrogenase (LDH) and other enzymes released during myocardial infarction; (ii) electrocardiogram (ECG or EKG) which is a graphic recordation of cardiac activity, either on paper or a computer monitor. An ECG can be beneficial in detecting disease and/or damage; (iii) echocardiogram (heart ultrasound) used to investigate congenital heart disease and assessing abnormalities of the heart wall, including functional abnormalities of the heart wall, valves and blood vessels; (iv) Doppler ultrasound can be used to measure blood flow across a heart valve; (v) nuclear medicine imaging (also referred to as radionuclide scanning in the art) allows visualization of the anatomy and function of an organ, and can be used to detect coronary artery disease, myocardial infarction, valve disease, heart transplant rejection, check the effectiveness of bypass surgery, or to select patients for angioplasty or coronary bypass graft.

Methods described herein can be used to treat and/or prevent myocardial ischemia. As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The technology provided herein can further be described in the following numbered paragraphs:

1. An isolated nucleic acid molecule encoding an Rrm2 polypeptide that, together with Rrm1 polypeptide comprises ribonucleotide reductase activity, the encoded Rrm2 polypeptide comprising a mutation that increases the intracellular level of the polypeptide as compared to wild-type Rrm2 polypeptide.
2. The isolated nucleic acid of paragraph 1, wherein the mutation increases the intracellular stability of the Rrm2 polypeptide relative to wild-type.
3. The isolated nucleic acid molecule of paragraph 1, wherein the mutation is in a ubiquitin-binding degron.
4. The isolated nucleic acid molecule of paragraph 3, wherein the mutation in the ubiquitin-binding degron prevents or inhibits ubiquitin-mediated degradation of its gene product.
5. The isolated nucleic acid molecule of paragraph 1, wherein the Rrm2 gene sequence encodes an Rrm2 polypeptide having 2 to 10 amino acid changes as compared to wild-type Rrm2 polypeptide sequence.
6. The isolated nucleic acid molecule of paragraph 1, wherein the wild-type Rrm2 gene sequence is SEQ ID NO: 3 or 5.
7. The isolated nucleic acid molecule of paragraph 3, wherein the ubiquitin-binding degron is encoded at nucleotides 88-96, 97-99, and/or 145-153 of SEQ ID NO: 3 or SEQ ID NO: 5.
8. The isolated nucleic acid molecule of paragraph 1, wherein the mutation is an amino acid substitution, deletion, or insertion.
9. The isolated nucleic acid molecule of paragraph 1, wherein the mutation is a mutation of a nucleotide selected from the group consisting of: 88-96, 97-99, and/or 145-153 positions of SEQ ID NO: 3 or SEQ ID NO: 5.
10. The isolated nucleic acid molecule of any of paragraphs 1-9, wherein the sequence is selected from SEQ ID NO: 16-20.
11. The isolated nucleic acid molecule of paragraph 2, wherein stability of the encoded polypeptide is increased at least 50% as compared to wild-type Rrm2.
12. The isolated nucleic acid molecule of paragraph 1, wherein the mutation increases the level of cytosolic 2-deoxy-ATP (dATP) in a cell when the isolated nucleic acid molecule is expressed in a cell as compared to expression of wild-type Rrm2.
13. The isolated nucleic acid molecule of paragraph 12, wherein the level of cytosolic dATP is increased at least 50% as compared to wild-type Rrm2.
14. The isolated nucleic acid molecule of paragraph 1, operably linked to a sequence that permits expression of the encoded polypeptide in a cell.
15. The isolated nucleic acid molecule of paragraph 14, wherein the sequence that permits expression of the encoded polypeptide in a cell comprises a promoter.
16. The isolated nucleic acid molecule of paragraph 15, wherein the promoter is selected from the group consisting of: a constitutive promoter, a ubiquitous promoter, an inducible promoter, a viral promoter, a tissue specific promoter, and a synthetic promoter.
17. The isolated nucleic acid molecule of paragraph 16, wherein the tissue specific promoter is a cardiac tissue specific promoter.
18. A vector comprising the isolated nucleic acid molecule of any one of paragraphs 1-17.
19. The vector of paragraph 18, wherein the vector is a viral vector.
20. The vector of any one of paragraphs 18-19, wherein the vector is a DNA or RNA virus.
21. The vector of any one of paragraphs 18-20, wherein the viral vector is an adeno associated virus (AAV), a lentivirus (LV), a herpes simplex virus (HSV), an adeno virus (AV), or a pox virus (PV) vector.
22. A polypeptide encoded by the isolated nucleic acid of any one of paragraphs 1-17.
23. The polypeptide of paragraph 22, wherein the polypeptide sequence is selected from SEQ ID NO: 4, 21-25.
24. A protein complex comprising the polypeptide of paragraph 22 or 23 and at least one polypeptide of a different sequence.
25. The protein complex of paragraph 24, wherein the complex comprises an Rrm1 polypeptide.
26. A composition comprising an isolated nucleic acid molecule of any one of paragraphs 1-17, a vector of any one of paragraphs 20-23, or a polypeptide of any one of paragraphs 22-25.
27. The composition of paragraph 28, further comprising a pharmaceutically acceptable carrier.
28. A pharmaceutical composition comprising an isolated nucleic acid molecule of any one of paragraphs 1-17, a vector of any one of paragraphs 18-21, or a polypeptide of any one of paragraphs 22-25.
29. A method of treating a cardiac disease or disorder, the method comprising administering to a subject in need thereof a composition of any one of paragraphs 26-27, or the pharmaceutical composition of paragraph 28.
30. The method of paragraph 29, wherein the cardiac disease or disorder is myocardial infarction or myocardial ischemia.
31. The method of paragraph 29, wherein the composition is administered directly to a cardiac cell.
32. The method of paragraph 31, wherein the cardiac cell is a cardiomyocyte.
33. The method of paragraph 29, wherein administering increases dATP in a cardiac cell as compared to an appropriate control.
34. The method of paragraph 33, wherein dATP is increased at least 50% as compared to an appropriate control.

35. The method of paragraphs 33 and 34, wherein dATP levels are measured via HPLC and/or mass spectrometry.
36. The method of paragraph 29, wherein administering increases RNR enzymatic activity in a cell as compared to an appropriate control.
37. The method of paragraph 36, wherein RNR enzymatic activity is increased at least 50% as compared to an appropriate control.
38. The method of paragraph 29, further comprising, prior to administering, diagnosing a subject as having a cardiac disease or disorder.
39. The method of paragraph 29, further comprising, prior to administering, receiving the results of an assay that diagnoses a subject as having a cardiac disease or disorder.
40. The method of paragraph 29, further comprising administering at least a second therapeutic.
41. The method of paragraph 1, wherein the polypeptide comprises two mutations.
42. A method of treating myocardial infarction in a subject, comprising increasing the amount of dATP content in cardiomyocytes in the subject.
43. The method of paragraph 42, wherein the method comprises overexpression of ribonucleotide reductase (RNR) in the cardiomyocytes in the subject.
44. A method of increasing the amount of dATP content in cardiomyocytes in a subject, comprising administering to the subject an effective amount of a vector comprising mutants of Rrm2, wherein the mutants overexpress RNR in the cardiomyocytes.
45. The method of paragraph 44, wherein the mutants of Rrm2 contain one or more mutations in the ubiquitin-binding region of the Rrm2 amino acid sequence.
46. The method of any previous paragraph, wherein the increased amount of dATP is measured by HPLC.
47. The method of any previous paragraph, wherein the overexpression is of Rrm1 or Rrm2.
48. Other methods and compositions as described and paragraphed herein.

This technology is further illustrated by the following example which should not be construed as limiting. The contents of all references cited throughout this application, as well as the figures are incorporated herein by reference.

Example 1

As described herein, engineering mutations into the ubiquitin-binding motif of Rrm2 increases the amount of Rrm2 overexpression and results in greater cell levels of dATP than unmutated (wild type) Rrm2 in RNR complex. An improved RNR vector using these engineered Rrm2 construct can be developed that is resistant to degradation through the ubiquitin-proteasome pathway and therefore enable more stable and consistent RNR enzyme activity and deoxynucleotide levels of cardiomyocytes in the heart. Without engineering Rrm2, RNR levels after AAV transduction are highly variable in mouse models of cardiomyopathy.

2-deoxy-ATP (dATP) is a nucleotide used in DNA synthesis but present in extremely low levels in post-mitotic cells. Methods of increasing dATP levels in cardiomyocytes is a potential therapy for cardiomyopathies. As little as 1% dATP increases both the magnitude and rate of contraction (see e.g., FIG. 1A; Korte et al., J Mol Cell Cardiol. 2011 December; 51(6):894-901).

Figure 2:
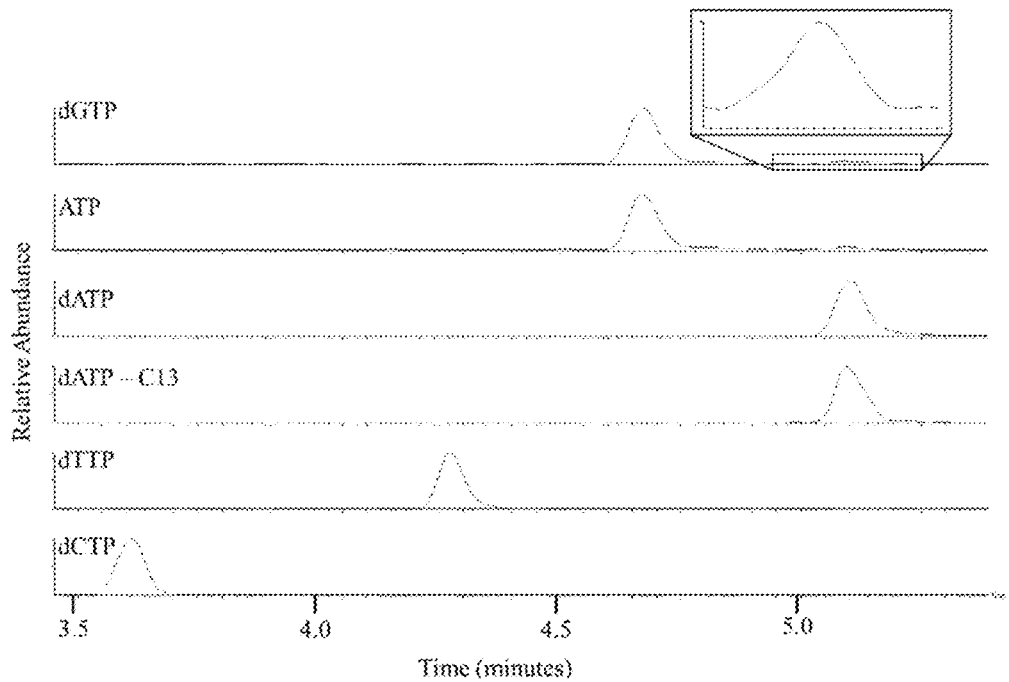
FIG. 2 is a series of line graphs showing quantification of deoxyribonucleotide triphosphates (dNTPs) in muscle tissues by high performance liquid chromatography with tandem mass spectrometry (HPLC-MS/MS). On the left are ion chromatograms showing relative abundance over time for dGTP, ATP, dATP, labeled C-13 dATP, dTTP, and dCTP upon injection of 62.5 fmol dNTPs, 1,250 fmol ATP, and 25,000 fmol of labeled C-13 dATP.

The concentration of dATP (i.e., [dATP]) can be elevated in cardiomyocytes by overexpression of ribonucleotide reductase (RNR). AAV-mediated overexpression of RNR in cardiomyocytes improved in vivo function in healthy mice and in rats subjected to myocardial infarction (see e.g., FIG. 1B-FIG. 1E; Kolwicz et al., Mol Ther. 2016 February; 24(2):240-250).

dNTPs can be quantified in muscle tissues by mass spectrometry. A fast and sensitive HPLC-MS/MS method has been developed for direct quantification of intracellular dNTPs from tissue (see e.g., FIG. 2). Exemplary dNTPs that can be detected by said HPLC-MS/MS method include but are not limited to deoxyguanosine triphosphate (dGTP), adenosine triphosphate (ATP), deoxyadenosine triphosphate dATP, deoxyadenosine triphosphate dATP containing carbon-13 isotope (dATP-C13), deoxythymidine triphosphate (dTTP), and deoxycytidine triphosphate (dCTP).

Figure 3:
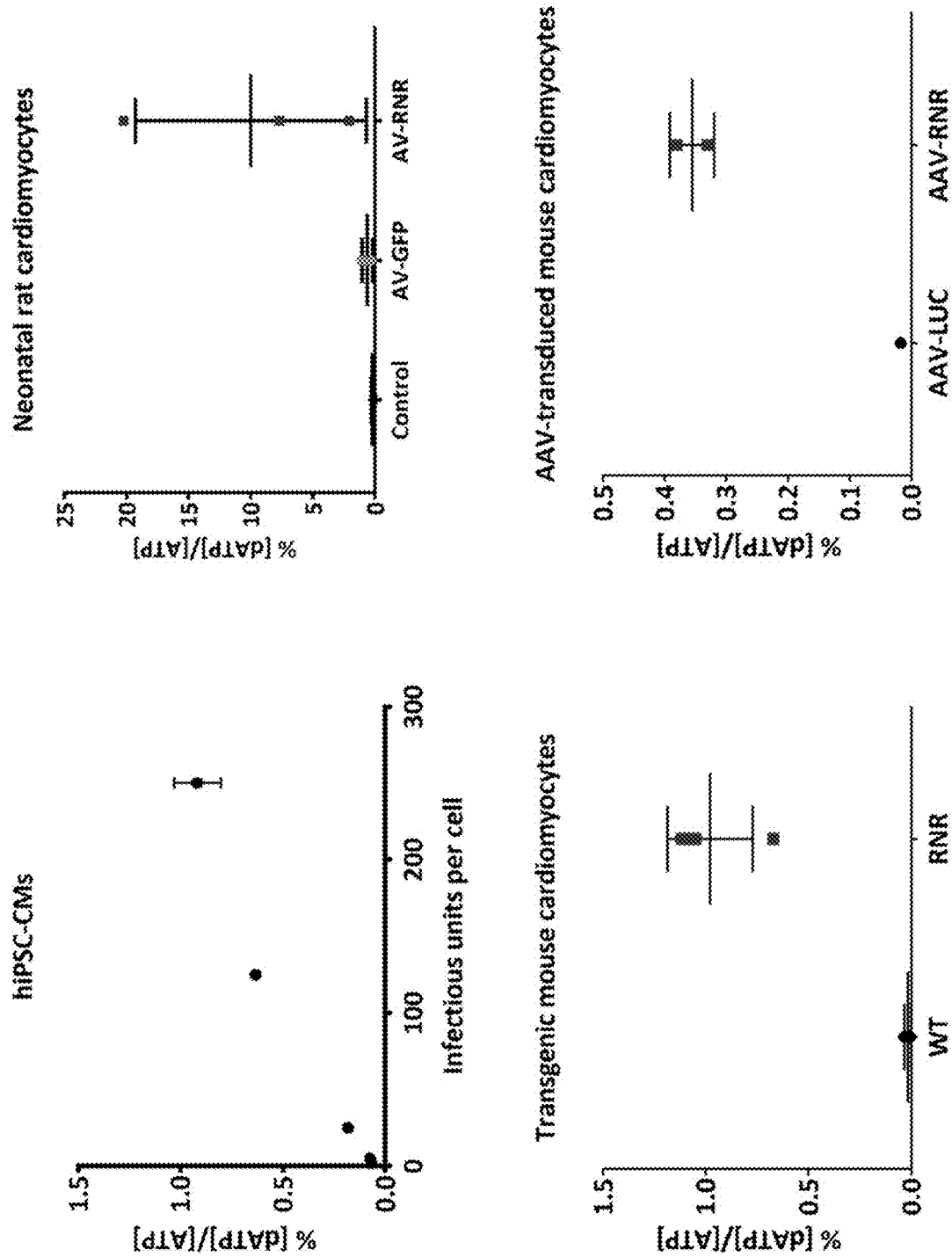
FIG. 3 is a series of dot plots showing that overexpression of RNR increases dATP content in cardiomyocytes. The term "hiPSC-CMs" denotes human induced pluripotent stem cell derived cardiomyocytes.

Overexpression of RNR increases dATP content in cardiomyocytes. Human induced pluripotent stem cell-derived cardiomyocytes, in vitro adenovirus-transduced neonatal rat cardiomyocytes, adult transgenic mouse cardiomyocytes, and in vivo AAV-transduced mouse cardiomyocytes all displayed elevated levels of dATP (see e.g., FIG. 3).

Figure 4:
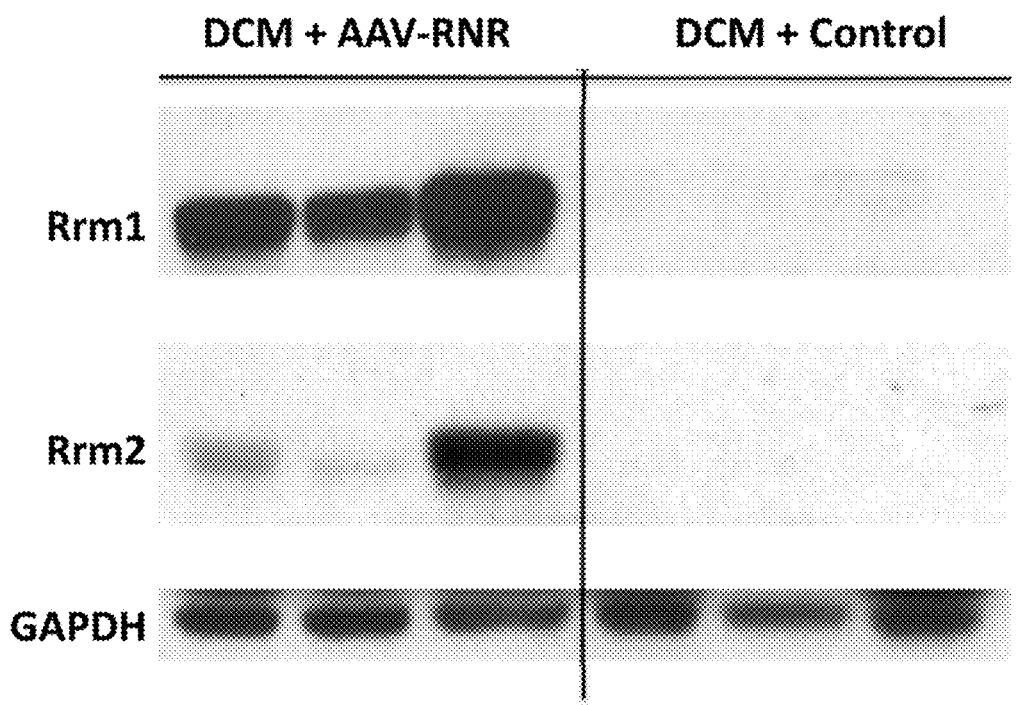
FIG. 4 shows a Western blot analysis of Rrm1 and Rrm2 proteins. Note that AAV-induced overexpression of Rrm2 can be highly variable.

AAV-induced overexpression of Rrm2 is highly variable. AAV-induced transduction of RNR is consistent in wild-type mice (see e.g., Kolwicz et al., Mol Ther. 2016 February; 24(2):240-250), but not in disease models. A transgenic mouse model of dilated cardiomyopathy showed overexpression of Rrm1 but inconsistent overexpression of Rrm2 (see e.g., FIG. 4).

Figure 5A:
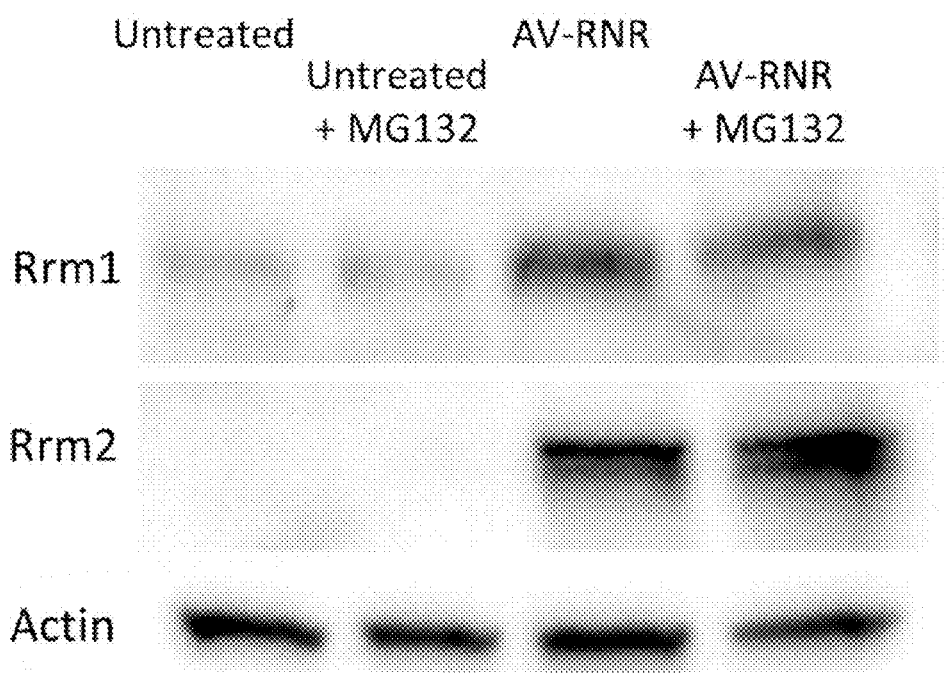
FIG. 5A-FIG. 5B is series and graphs showing that Rrm2 is degraded in cardiomyocytes by ubiquitin-proteasome activity.
Figure 5B:
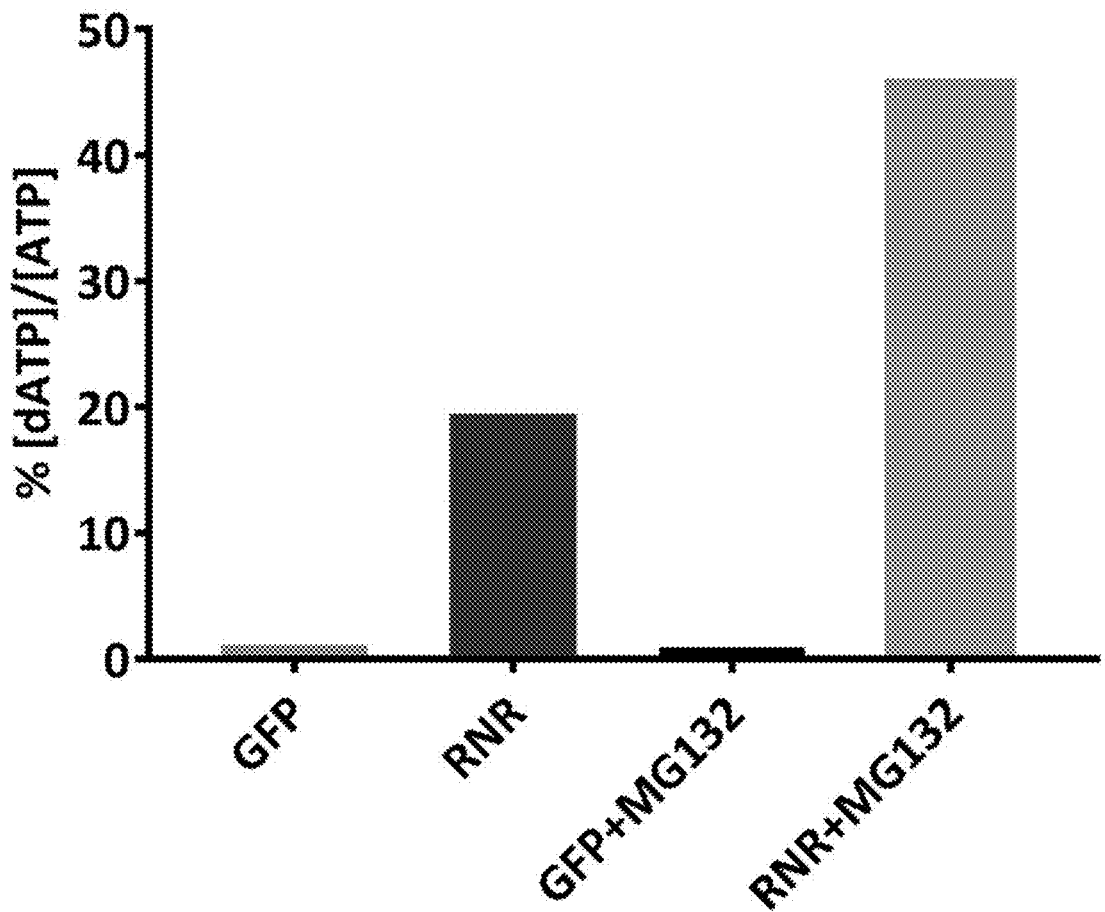

Rrm2 is degraded in cardiomyocytes by ubiquitin-proteasome activity. Neonatal rat cardiomyocytes transduced for three days in vitro with RNR have greater levels of Rrm2 after 3 hours of incubation in MG-132, a potent proteasome inhibitor (see e.g., FIG. 5A). MG132-treated cells also have higher [dATP] in preliminary measurements (see e.g., FIG. 5B).

Figure 6A:
FIG. 6A-FIG. 6C is series and graphs showing that engineered mutations in Rrm2 increase RNR levels in hiPSC-CMs. Exemplary Rrm2 mutants include but are not limited to 49ARA, 30AAA/49ARA double mutant, 30AAN, 30AAA, 33T/A (see e.g., FIG. 9).
Figure 6B:
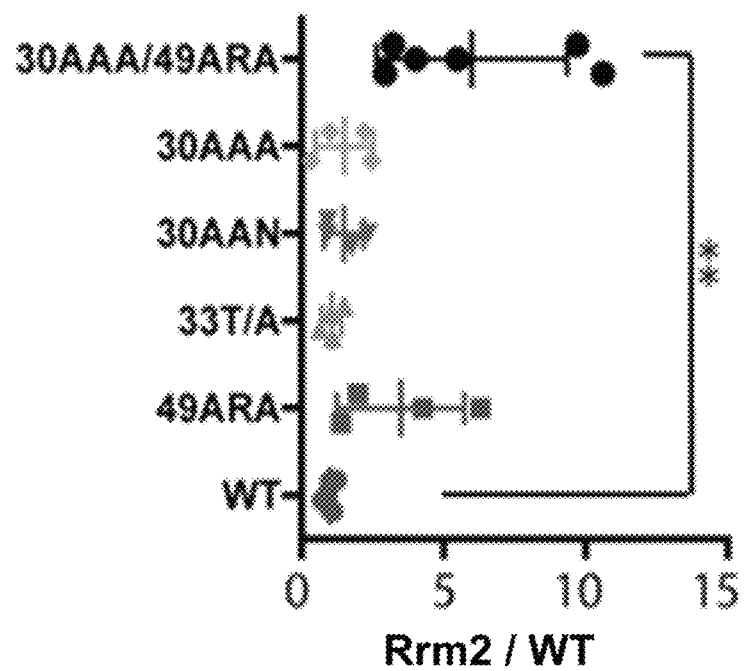
Figure 6C:
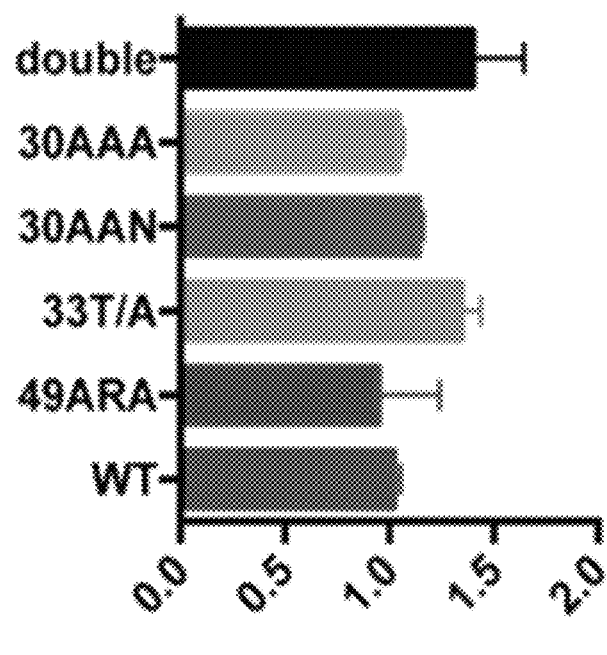
Figure 8:
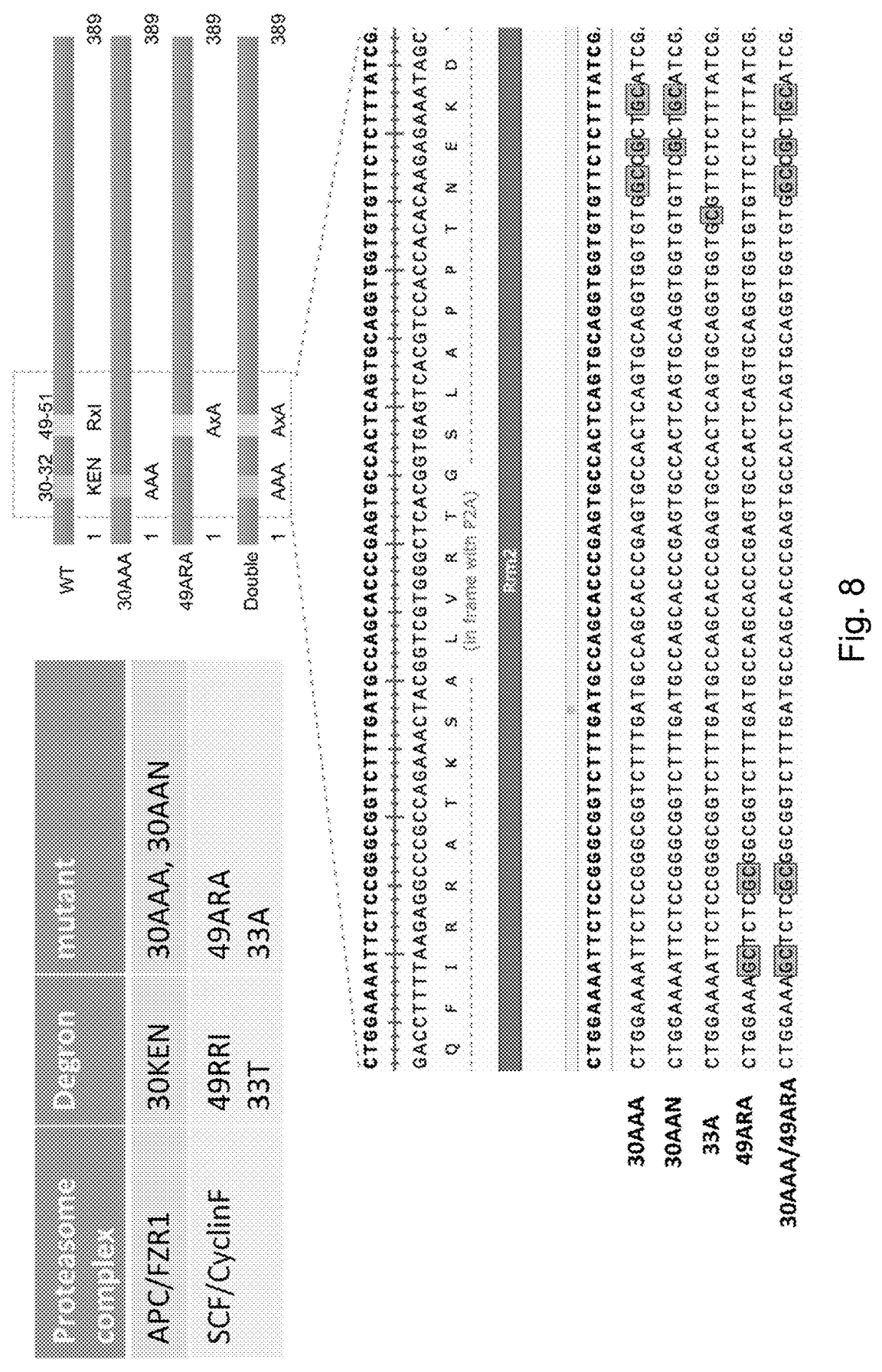

Engineered mutations in Rrm2 increase RNR levels in hiPSC-CMs. Human induced-pluripotent stem cells were transfected in vitro with plasmids for RNR containing mutations in the ubiquitin-binding region of Rrm2 (see e.g., FIG. 6A-FIG. 6C). A version containing two mutations was chosen for adenovirus production based on protein levels. FIG. 8 shows nucleotide sequences for 5 exemplary Rrm2 mutants compared to WT Rrm2.

Figure 7:
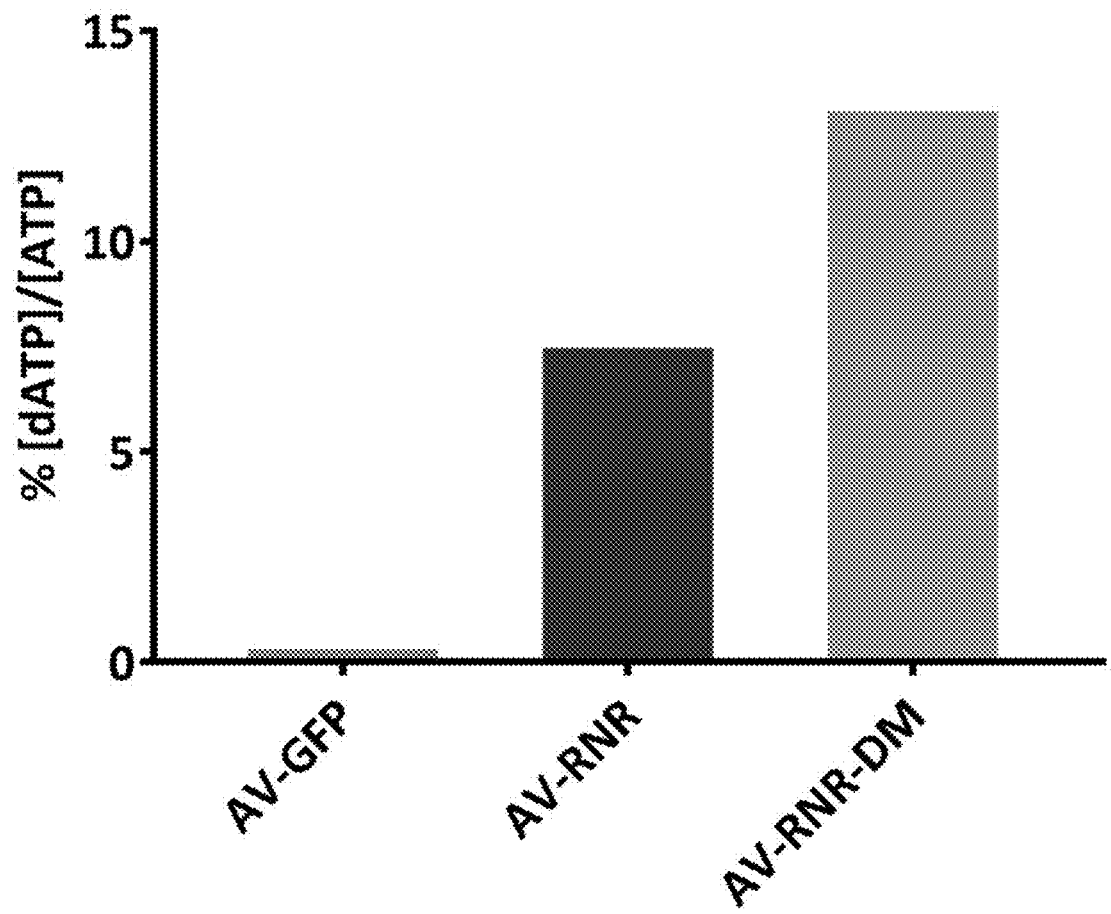
FIG. 7 is a bar graph showing that engineered Rrm2 elevates [dATP] in neonatal rat cardiomyocytes in vitro compared to WT Rrm2. DM designates the Rrm2 30AAA/49ARA double mutant.

Engineered Rrm2 elevates [dATP] in neonatal rat cardiomyocytes in vitro. Cardiomyocytes transduced by AV with Rrm1 and double-mutant Rrm2 (AV-RNR-DM) have elevated [dATP] as measured by mass spectrometry (see e.g., FIG. 7).

Degradation of Rrm2 via the ubiquitin-proteasome complex can be prevented in vitro by the introduction of engineered mutations in the ubiquitin-binding region. Pharmacological inhibition of proteasome activity in transduced cells leads to increased levels of Rrm2 protein and dATP. Without engineering Rrm2, RNR levels after AAV transduction are highly variable in mouse models of cardiomyopathy. dATP levels can be measured in cultured and adult cardiomyocytes with high sensitivity by HPLC/MS/MS and can be elevated by overexpressing RNR.

The proteasome thus plays a key role in cardiac disease. An improved RNR vector can be developed that is be resistant to degradation through the ubiquitin-proteasome pathway, therefore enabling more stable and consistent RNR enzyme activity and deoxynucleotide levels of cardiomyocytes. Double-mutant Rrm2 is one approach to titrate the amount of dATP produced in myocytes. An AAV can be created for muscle-specific transduction of RNR-DM in vivo.

The invention claimed is:

1. An isolated nucleic acid molecule encoding a mutant Rrm2 polypeptide, wherein the isolated nucleic acid molecule comprises a mutated version of SEQ ID NO: 3 or SEQ ID NO: 5, the version having at least a mutation of a nucleotide selected from the group consisting of: positions 88-96, 97-99, and 145-153 of SEQ ID NO: 3 or SEQ ID NO: 5, wherein the encoded mutant Rrm2 polypeptide comprises a mutation in a ubiquitin-binding degron relative to a wild-type Rrm2 polypeptide, wherein the ubiquitin-binding degron is encoded by wild-type nucleotides 88-96, 97-99, and/or 145-153 of SEQ ID NO: 3 or SEQ ID NO: 5, and wherein the mutation in the ubiquitin-binding degron increases the intracellular stability of the mutant Rrm2 polypeptide compared to the wild-type.

2. The isolated nucleic acid molecule of claim 1, wherein the mutation in the ubiquitin-binding degron prevents or inhibits ubiquitin-mediated degradation of its gene product.

3. The isolated nucleic acid molecule of claim 1, wherein the encoded mutant Rrm2 polypeptide comprises 2 to 10 amino acid changes as compared to wild-type Rrm2 polypeptide sequence.

4. The isolated nucleic acid molecule of claim 1, wherein the isolated nucleic acid molecule has a nucleic acid sequence selected from SEQ ID NO: 16-20.

5. The isolated nucleic acid molecule of claim 1, wherein the mutation in the ubiquitin-binding degron increases the level of cytosolic 2-deoxy-ATP (dATP) in a cell when the isolated nucleic acid molecule is expressed in a cell as compared to expression of wild-type Rrm2.

6. The isolated nucleic acid molecule of claim 1, wherein the isolated nucleic acid molecule is operably linked to a sequence that permits expression of the encoded polypeptide in a cell.

7. A vector comprising the isolated nucleic acid molecule of claim 1.

8. The vector of claim 7, wherein the vector is a viral vector.

9. The vector of claim 8, wherein the viral vector is an adeno associated virus (AAV), a lentivirus (LV), a herpes simplex virus (HSV), an adeno virus (AV), or a pox virus (PV) vector.

10. A composition comprising:
(i) the isolated nucleic acid molecule of claim 1; or
(ii) a vector comprising a nucleic acid molecule comprising the sequence of the isolated nucleic acid molecule of claim 1.

* * * * *

SEQUENCE LISTING

<160> NUMBER OF SEQ ID NOS: 32

<210> SEQ ID NO 1
<211> LENGTH: 2379
<212> TYPE: DNA
<213> ORGANISM: Homo sapiens

<400> SEQUENCE: 1

```
atgcatgtga tcaagcgaga tggccgccaa gaacgagtca tgtttgacaa aattacatct      60
cgaatccaga agctttgtta tggactcaat atggattttg ttgatcctgc tcagatcacc     120
atgaaagtaa tccaaggctt gtacagtggg gtcaccacag tggaactaga tactttggct     180
gctgaaacag ctgcaacctt gactactaag caccctgact atgctatcct ggcagccagg     240
atcgctgtct ctaacttgca caagaaaaca agaaagtgt tcagtgatgt gatggaagac      300
ctctataact acataaatcc acataatggc aaacactctc ccatggtggc caagtcaaca     360
ttggatattg ttctggccaa taagatcgc ctgaattctg ctattatcta tgaccgagat      420
ttctcttaca attacttcgg ctttaagacg ctagagcggt cttatttgtt gaagatcaat     480
ggaaaagtgg ctgaaagacc acaacatatg ttgatgagag tatctgttgg atccacaaa     540
gaagacattg atgcagcaat tgaaacatat aatcttcttt ctgagaggtg gtttactcat     600
gcttcgccca ctctcttcaa tgctggtacc aaccgcccac aactttctag ctgttttctt     660
ctgagtatga agatgacag cattgaaggc atttatgaca ctctaaagca atgtgcattg      720
atttctaagt ctgctggagg aattggtgtt gctgtgagtt gtattcgggc tactggcagc     780
tacattgctg gactaatgg caattccaat ggccttgtac cgatgctgag agtatataac      840
aacacagctc gatatgtgga tcaaggtggg aacaagcgtc tggggcatt tgctatttac      900
ctggagcctt ggcatttaga catctttgaa ttccttgatt aaagaagaa cacaggaaag      960
gaagagcagc gtgccagaga tcttttcttt gctctttgga ttccggatct cttcatgaaa    1020
cgagtggaga ctaatcagga ctggtctttg atgtgtccaa atgagtgtcc tggtctggat    1080
gaggtttggg gagaggaatt tgagaaacta tatgcaagtt atgagaaaca aggtcgtgtc    1140
cgcaaagttg taaaagctca gcagctttgg tatgccatca ttgagtctca gacggaaaca    1200
ggcaccccgt atatgctcta caagattcc tgtaatcgaa agagcaacca gcagaacctg    1260
ggaaccatca aatgcagcaa cctgtgcaca gaaatagtgg agtacaccag caaagatgag    1320
gttgctgttt gtaatttggc ttccctggcc ctgaatatgt atgtcacatc agaacacaca    1380
tacgacttta agaagttggc tgaagtcact aaagtcgttg tccgaaactt gaataaaatt    1440
attgatataa actactatcc tgtaccagag gcatgcctat caaataaacg ccatcgcccc    1500
attggaattg gggtacaagg tctggcagat gcttttatcc tgatgagata ccctttgag    1560
agtgcagaag cccagttact gaataagcag atctttgaaa ctatttatta tggtgctctg    1620
gaagccagct gtgaccttgc caaggagcag ggcccatacg aaacctatga gggctctcca    1680
gttagcaaag gaattcttca gtatgatatg tggaatgtta ctcctacaga cctatgggac    1740
tggaaggttc tcaaggagaa gattgcaaag tatggtataa gaaacagttt acttattgcc    1800
ccgatgccta cagcttccac tgctcagatc ctggggaata atgagtccat tgaaccttac    1860
accagcaaca tctatactcg cagagtcttg tcaggagaat tcagattgt aaatcctcac    1920
ttattgaaag atcttaccga gcggggccta tggcatgaag agatgaaaaa ccagattatt    1980
gcatgcaatg tgctctattca gagcatacca gaaattcctg atgacctgaa gcaacttat    2040
aaaactgtgt gggaaatctc tcagaaaact gttctcaaga tggcagctga gagaggtgct    2100
```

```
ttcattgatc aaagccaatc tttgaacatc cacattgctg agcctaacta tggcaaactc    2160
actagtatgc acttctacgg ctggaagcag ggtttgaaga ctgggatgta ttatttaagg    2220
acaagaccag cggctaatcc aatccagttc actctaaata aggagaagct aaaagataaa    2280
gaaaaggtat caaagagga agaagagaag gagaggaaca cagcagccat ggtgtgctct    2340
ttggagaata gagatgaatg tctgatgtgt ggatcctga                          2379
```

```
<210> SEQ ID NO 2
<211> LENGTH: 792
<212> TYPE: PRT
<213> ORGANISM: Homo sapiens

<400> SEQUENCE: 2
```

```
Met His Val Ile Lys Arg Asp Gly Arg Gln Glu Arg Val Met Phe Asp
1               5                   10                  15

Lys Ile Thr Ser Arg Ile Gln Lys Leu Cys Tyr Gly Leu Asn Met Asp
            20                  25                  30

Phe Val Asp Pro Ala Gln Ile Thr Met Lys Val Ile Gln Gly Leu Tyr
        35                  40                  45

Ser Gly Val Thr Thr Val Glu Leu Asp Thr Leu Ala Ala Glu Thr Ala
    50                  55                  60

Ala Thr Leu Thr Thr Lys His Pro Asp Tyr Ala Ile Leu Ala Ala Arg
65                  70                  75                  80

Ile Ala Val Ser Asn Leu His Lys Glu Thr Lys Lys Val Phe Ser Asp
                85                  90                  95

Val Met Glu Asp Leu Tyr Asn Tyr Ile Asn Pro His Asn Gly Lys His
            100                 105                 110

Ser Pro Met Val Ala Lys Ser Thr Leu Asp Ile Val Leu Ala Asn Lys
        115                 120                 125

Asp Arg Leu Asn Ser Ala Ile Ile Tyr Asp Arg Asp Phe Ser Tyr Asn
    130                 135                 140

Tyr Phe Gly Phe Lys Thr Leu Glu Arg Ser Tyr Leu Leu Lys Ile Asn
145                 150                 155                 160

Gly Lys Val Ala Glu Arg Pro Gln His Met Leu Met Arg Val Ser Val
                165                 170                 175

Gly Ile His Lys Glu Asp Ile Asp Ala Ala Ile Glu Thr Tyr Asn Leu
            180                 185                 190

Leu Ser Glu Arg Trp Phe Thr His Ala Ser Pro Thr Leu Phe Asn Ala
        195                 200                 205

Gly Thr Asn Arg Pro Gln Leu Ser Ser Cys Phe Leu Leu Ser Met Lys
    210                 215                 220

Asp Asp Ser Ile Glu Gly Ile Tyr Asp Thr Leu Lys Gln Cys Ala Leu
225                 230                 235                 240

Ile Ser Lys Ser Ala Gly Gly Ile Gly Val Ala Val Ser Cys Ile Arg
                245                 250                 255

Ala Thr Gly Ser Tyr Ile Ala Gly Thr Asn Gly Asn Ser Asn Gly Leu
            260                 265                 270

Val Pro Met Leu Arg Val Tyr Asn Asn Thr Ala Arg Tyr Val Asp Gln
        275                 280                 285

Gly Gly Asn Lys Arg Pro Gly Ala Phe Ala Ile Tyr Leu Glu Pro Trp
    290                 295                 300

His Leu Asp Ile Phe Glu Phe Leu Asp Leu Lys Lys Asn Thr Gly Lys
305                 310                 315                 320
```

-continued

```
Glu Glu Gln Arg Ala Arg Asp Leu Phe Phe Ala Leu Trp Ile Pro Asp
                325                 330                 335
Leu Phe Met Lys Arg Val Glu Thr Asn Gln Asp Trp Ser Leu Met Cys
            340                 345                 350
Pro Asn Glu Cys Pro Gly Leu Asp Glu Val Trp Gly Glu Glu Phe Glu
        355                 360                 365
Lys Leu Tyr Ala Ser Tyr Glu Lys Gln Gly Arg Val Arg Lys Val Val
    370                 375                 380
Lys Ala Gln Gln Leu Trp Tyr Ala Ile Ile Glu Ser Gln Thr Glu Thr
385                 390                 395                 400
Gly Thr Pro Tyr Met Leu Tyr Lys Asp Ser Cys Asn Arg Lys Ser Asn
            405                 410                 415
Gln Gln Asn Leu Gly Thr Ile Lys Cys Ser Asn Leu Cys Thr Glu Ile
        420                 425                 430
Val Glu Tyr Thr Ser Lys Asp Glu Val Ala Val Cys Asn Leu Ala Ser
    435                 440                 445
Leu Ala Leu Asn Met Tyr Val Thr Ser Glu His Thr Tyr Asp Phe Lys
    450                 455                 460
Lys Leu Ala Glu Val Thr Lys Val Val Arg Asn Leu Asn Lys Ile
465                 470                 475                 480
Ile Asp Ile Asn Tyr Tyr Pro Val Pro Glu Ala Cys Leu Ser Asn Lys
            485                 490                 495
Arg His Arg Pro Ile Gly Ile Gly Val Gln Gly Leu Ala Asp Ala Phe
        500                 505                 510
Ile Leu Met Arg Tyr Pro Phe Glu Ser Ala Glu Ala Gln Leu Leu Asn
    515                 520                 525
Lys Gln Ile Phe Glu Thr Ile Tyr Tyr Gly Ala Leu Glu Ala Ser Cys
    530                 535                 540
Asp Leu Ala Lys Glu Gln Gly Pro Tyr Glu Thr Tyr Glu Gly Ser Pro
545                 550                 555                 560
Val Ser Lys Gly Ile Leu Gln Tyr Asp Met Trp Asn Val Thr Pro Thr
            565                 570                 575
Asp Leu Trp Asp Trp Lys Val Leu Lys Glu Lys Ile Ala Lys Tyr Gly
        580                 585                 590
Ile Arg Asn Ser Leu Leu Ile Ala Pro Met Pro Thr Ala Ser Thr Ala
    595                 600                 605
Gln Ile Leu Gly Asn Asn Glu Ser Ile Glu Pro Tyr Thr Ser Asn Ile
    610                 615                 620
Tyr Thr Arg Arg Val Leu Ser Gly Glu Phe Gln Ile Val Asn Pro His
625                 630                 635                 640
Leu Leu Lys Asp Leu Thr Glu Arg Gly Leu Trp His Glu Glu Met Lys
            645                 650                 655
Asn Gln Ile Ile Ala Cys Asn Gly Ser Ile Gln Ser Ile Pro Glu Ile
        660                 665                 670
Pro Asp Asp Leu Lys Gln Leu Tyr Lys Thr Val Trp Glu Ile Ser Gln
    675                 680                 685
Lys Thr Val Leu Lys Met Ala Ala Glu Arg Gly Ala Phe Ile Asp Gln
    690                 695                 700
Ser Gln Ser Leu Asn Ile His Ile Ala Glu Pro Asn Tyr Gly Lys Leu
705                 710                 715                 720
Thr Ser Met His Phe Tyr Gly Trp Lys Gln Gly Leu Lys Thr Gly Met
            725                 730                 735
Tyr Tyr Leu Arg Thr Arg Pro Ala Ala Asn Pro Ile Gln Phe Thr Leu
```

740              745              750
Asn Lys Glu Lys Leu Lys Asp Lys Glu Lys Val Ser Lys Glu Glu Glu
            755                  760                  765

Glu Lys Glu Arg Asn Thr Ala Ala Met Val Cys Ser Leu Glu Asn Arg
        770                  775                  780

Asp Glu Cys Leu Met Cys Gly Ser
785                 790

<210> SEQ ID NO 3
<211> LENGTH: 1170
<212> TYPE: DNA
<213> ORGANISM: Homo sapiens

<400> SEQUENCE: 3
atgctctccc tccgtgtccc gctcgcgccc atcacggacc cgcagcagct gcagctctcg        60
ccgctgaagg ggctcagctt ggtcgacaag gagaacacgc cgccggcccct gagcgggacc      120 cgcgtcctgg ccagcaagac cgcgaggagg atcttccagg agcccacgga gccgaaaact      180
aaagcagctg ccccggcgt ggaggatgag ccgctgctga gagaaaaccc ccgccgcttt       240
gtcatcttcc ccatcgagta ccatgatatc tggcagatgt ataagaaggc agaggcttcc      300
ttttggaccg ccgaggaggt ggacctctcc aaggacattc agcactggga atccctgaaa      360
cccgaggaga gatattttat atcccatgtt ctggctttct ttgcagcaag cgatggcata      420
gtaaatgaaa acttggtgga gcgatttagc caagaagttc agattacaga gcccgctgt       480 ttctatggct tccaaattgc catggaaaac atacattctg aaatgtatag tcttcttatt      540
gacacttaca taaaagatcc caagaaagg gaatttctct tcaatgccat tgaaacgatg       600
ccttgtgtca agaagaaggc agactgggcc ttgcgctgga ttggggacaa agaggctacc      660
tatggtgaac gtgttgtagc ctttgctgca gtggaaggca ttttctttttc cggttctttt      720 gcgtcgatat tctggctcaa gaacgagga ctgatgcctg cctcacatt ttctaatgaa        780 cttattagca gagatgaggg tttacactgt gattttgctt gcctgatgtt caaacacctg      840
gtacacaaac catcggagga gagagtaaga gaaataatta tcaatgctgt tcggatagaa      900
caggagttcc tcactgaggc cttgcctgtg aagctcattg ggatgaattg cactctaatg      960
aagcaataca ttgagtttgt ggcagacaga cttatgctgg aactgggttt tagcaaggtt     1020
ttcagagtag agaacccatt tgactttatg gagaatatt cactggaagg aaagactaac      1080
ttctttgaga agagagtagg cgagtatcag aggatgggag tgatgtcaag tccaacagag     1140 aattcttta ccttggatgc tgacttctaa                                       1170

<210> SEQ ID NO 4
<211> LENGTH: 389
<212> TYPE: PRT
<213> ORGANISM: Homo sapiens

<400> SEQUENCE: 4

Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Lys Glu Asn
            20                  25                  30

Thr Pro Pro Ala Leu Ser Gly Thr Arg Val Leu Ala Ser Lys Thr Ala
        35                  40                  45

Arg Arg Ile Phe Gln Glu Pro Thr Glu Pro Lys Thr Lys Ala Ala Ala
    50                  55                  60

```
Pro Gly Val Glu Asp Glu Pro Leu Leu Arg Glu Asn Pro Arg Arg Phe
 65                  70                  75                  80

Val Ile Phe Pro Ile Glu Tyr His Asp Ile Trp Gln Met Tyr Lys Lys
                 85                  90                  95

Ala Glu Ala Ser Phe Trp Thr Ala Glu Val Asp Leu Ser Lys Asp
            100                 105                 110

Ile Gln His Trp Glu Ser Leu Lys Pro Glu Glu Arg Tyr Phe Ile Ser
        115                 120                 125

His Val Leu Ala Phe Phe Ala Ala Ser Asp Gly Ile Val Asn Glu Asn
    130                 135                 140

Leu Val Glu Arg Phe Ser Gln Glu Val Gln Ile Thr Glu Ala Arg Cys
145                 150                 155                 160

Phe Tyr Gly Phe Gln Ile Ala Met Glu Asn Ile His Ser Glu Met Tyr
                165                 170                 175

Ser Leu Leu Ile Asp Thr Tyr Ile Lys Asp Pro Lys Glu Arg Glu Phe
            180                 185                 190

Leu Phe Asn Ala Ile Glu Thr Met Pro Cys Val Lys Lys Lys Ala Asp
        195                 200                 205

Trp Ala Leu Arg Trp Ile Gly Asp Lys Glu Ala Thr Tyr Gly Glu Arg
    210                 215                 220

Val Val Ala Phe Ala Ala Val Glu Gly Ile Phe Phe Ser Gly Ser Phe
225                 230                 235                 240

Ala Ser Ile Phe Trp Leu Lys Lys Arg Gly Leu Met Pro Gly Leu Thr
                245                 250                 255

Phe Ser Asn Glu Leu Ile Ser Arg Asp Glu Gly Leu His Cys Asp Phe
            260                 265                 270

Ala Cys Leu Met Phe Lys His Leu Val His Lys Pro Ser Glu Glu Arg
        275                 280                 285

Val Arg Glu Ile Ile Ile Asn Ala Val Arg Ile Glu Gln Glu Phe Leu
    290                 295                 300

Thr Glu Ala Leu Pro Val Lys Leu Ile Gly Met Asn Cys Thr Leu Met
305                 310                 315                 320

Lys Gln Tyr Ile Glu Phe Val Ala Asp Arg Leu Met Leu Glu Leu Gly
                325                 330                 335

Phe Ser Lys Val Phe Arg Val Glu Asn Pro Phe Asp Phe Met Glu Asn
            340                 345                 350

Ile Ser Leu Glu Gly Lys Thr Asn Phe Phe Glu Lys Arg Val Gly Glu
        355                 360                 365

Tyr Gln Arg Met Gly Val Met Ser Ser Pro Thr Glu Asn Ser Phe Thr
    370                 375                 380

Leu Asp Ala Asp Phe
385

<210> SEQ ID NO 5
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgctgagtc tgagggtccc actggcacct atcaccgatc acagcagct gcagctgagc      60 ccactgaaag gcctgagtct ggtcgataaa gagaacacac cacctgcact gagtggcact    120
cgggtgctgg catcaaagac cgcccggaga attttccagg agccaaccga acccaaaaca    180
```

```
aaggccgctg cacctggggt cgaggacgaa ccactgctga gagagaatcc caggcgcttc     240 gtgattttc  ctatcgaata ccacgatatt tggcagatgt ataagaaagc tgaggcaagt    300
ttctggacag ctgaggaagt ggacctgagc aaagacatcc agcactggga atccctgaag    360
ccagaggaaa ggtacttcat ttctcatgtg ctggcattct tgccgctag  tgacgggatc    420 gtgaacgaga atctggtcga acgctttagc caggaggtgc agatcactga agcccgatgc    480
ttctatggat ttcagattgc tatggagaac atccattcag aaatgtacag cctgctgatt    540
gacacctata tcaaagatcc taaggagcgc gagttcctgt taatgccat  tgagacaatg    600 ccatgtgtga agaaaaaggc agactgggct ctgcgatgga tcggcgataa ggaggctact    660
tacggggaaa gagtggtcgc attcgcagcc gtggagggaa ttttctttc  tggcagtttc    720 gcttccatct tttggctgaa aaagcgaggc ctgatgcctg gctgaccttt tccaacgag     780 ctgatttctc gcgacgaagg cctgcactgc gatttcgcct gtctgatgtt taaacacctg    840
gtgcataagc cctctgagga acgagtccgg gagatcatta tcaacgcagt gaggatcgag    900
caggagttcc tgacagaagc cctgcctgtc aaactgattg gcatgaattg cactctgatg    960
aagcagtaca tcgagtttgt ggccgacagg ctgatgctgg aactgggatt ctcaaaggtg   1020
tttcgcgtcg agaacccatt cgattttatg gagaatatca gcctggaagg caaaacaaac   1080
ttctttgaga agagagtcgg ggaatatcag aggatgggcg tgatgagcag ccccactgag   1140
aatagcttca ccctggacgc cgatttttga                                    1170
```

<210> SEQ ID NO 6
<211> LENGTH: 3633
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
gctagcgaat tcgccaccat gcacgtcatc aagagagacg ggaggcagga aagagtcatg     60
ttcgataaaa tcacttcaag aatccagaaa ctgtgttacg ggctgaacat ggacttcgtc    120
gatcctgccc agattaccat gaaagtgatc cagggactgt actctggcgt caccacagtg    180
gagctggaca cactggccgc tgaaaccgca gccacactga ctaccaaaca cccagattat    240
gcaattctgg ctgcacggat cgccgtgagt aatctgcata aggagacaaa gaaagtcttc    300
tcagacgtga tggaggacct gtacaattat atcaaccctc acaatgggaa acattcacca    360
atggtcgcta agagcactct ggacattgtg ctggccaaca aagatcggct gaacagcgct    420
atcatctacg accgggattt cagttacaac tacttcggct ttaagacact ggagagatca    480
tatctgctga aaatcaatgg gaaggtggcc gaacggcctc agcacatgct gatgagagtc    540
agcgtgggca ttcataagga ggacattgat gccgctatcg aaacttacaa cctgctgagc    600
gagcgctggt tcacccacgc ttcccctaca ctgtttaacg caggaaccaa tcgaccacag    660
ctgagcagct gcttcctgct gagcatgaag gacgattcca tcgagggcat ctacgacacc    720
ctgaaacagt gcgcactgat ttctaagagt gccggcggga tcgagtcgc  tgtgagttgt    780 attcgggcaa ccggctcata tatcgccggc acaaacggca cagcaacgg  gctggtcccc    840 atgctgaggg tgtacaacaa tacagcccgc tatgtggatc agggaggcaa caagagacca    900
ggagcatttg ccatctacct ggaacccgg  cacctgaca ttttcgagtt tctggatctg    960
aagaaaaata ctggcaaaga ggaacagagg gctcgcgacc tgttctttgc actgtggatt   1020
```

```
cccgacctgt tcatgaagag ggtggagacc aaccaggact ggagcctgat gtgcccaat     1080 gagtgtcctg ggctggatga agtgtgggga gaggaatttg aaaaactgta cgccagttat    1140
gagaagcagg gccgagtgcg aaagtggtc aaggcccagc agctgtggta cgctatcatt     1200
gagagccaga cagaaactgg cacccctac atgctgtata agactcttg caaccgcaag      1260 agtaaccagc agaatctggg gaccatcaaa tgcagcaatc tgtgtacaga gattgtggaa    1320
tatacttcca aggatgaggt cgccgtgtgt aacctggcat cactggccct gaatatgtac    1380
gtcacaagcg agcacactta tgacttcaag aaactggctg aagtgaccaa agtggtcgtg   1440
aggaatctga acaagatcat tgacatcaac tactatcccg tgcctgaggc ctgcctgagc    1500
aataagagac ataggcccat cgggattgga gtgcagggcc tggctgacgc attcatcctg    1560
atgcgctacc cttttgagtc cgccgaagct cagctgctga caagcagat ttttgaaaca    1620 atctactacg gggctctgga ggcatcttgt gacctggcca agaacaggg accctacgag    1680 acttatgaag ctcccctgt gtctaagggc atcctgcagt acgatatgtg aacgtcaca     1740 ccaactgacc tgtgggattg aaagtgctg aaggagaaaa ttgcaaagta tggcatccgg    1800
aacagcctgc tgatcgcccc aatgcccact gcctctaccg ctcagattct gggcaacaat   1860
gagtccatcg aaccatacac ttctaacatc tacacccgga gagtcctgag cggggagttc    1920
cagatcgtga atccccacct gctgaaagac ctgaccgaac ggggactgtg gcatgaggaa    1980
atgaagaacc agatcattgc ctgcaatggc agtatccagt caattcctga gatcccagac    2040
gatctgaaac agctgtacaa gacagtctgg gagatcagcc agaaactgt gctgaagatg     2100 gcagccgaaa gagggctttt cattgatcag tcacagagcc tgaacatcca cattgccgag    2160
cccaattacg gaaagctgac ctccatgcat ttttatgggt ggaaacaggg actgaagact    2220
ggcatgtact atctgcgcac ccgaccagct gcaaacccca tccagtttac cctgaataag    2280
gagaaactga aggacaaaga aaaggtgtcc aagaaggaag aggaaaagga gagaaacaca    2340
gccgctatgg tgtgttctct ggagaatagg gatgaatgcc tgatgtgtgg cagtggaagc    2400
ggagctacta acttcagcct gctgaagcag gctggagacg tggaggagaa ccctggacct    2460
ctgagtctga gggtcccact ggcacctatc accgatccac agcagctgca gctgagccca    2520
ctgaaaggcc tgagtctggt cgataaagag aacacaccac ctgcactgag tggcactcgg    2580
gtgctggcat caaagaccgc ccggagaatt ttccaggagc aaccgaacc caaaacaaag    2640 gccgctgcac ctggggtcga ggacgaacca ctgctgagag agaatcccag gcgcttcgtg    2700
attttcccta tcgaatacca cgatatttgg cagatgtata agaaagctga ggcaagtttc    2760
tggacagctg aggaagtgga cctgagcaaa gacatccagc actgggaatc cctgaagcca    2820
gaggaaaggt acttcatttc tcatgtgctg gcattctttg ccgctagtga cgggatcgtg    2880
aacgagaatc tggtcgaacg ctttagccag gaggtgcaga tcactgaagc ccgatgcttc    2940
tatggatttc agattgctat ggagaacatc cattcagaaa tgtacagcct gctgattgac    3000
acctatatca aagatcctaa ggagcgcgag ttcctgttta atgccattga caatgccca     3060 tgtgtgaaga aaaaggcaga ctgggctctg cgatggatcg cgataagga ggctacttac     3120 ggggaaagag tggtcgcatt cgcagccgtg gagggaattt tctttctgg cagtttcgct     3180 tccatctttt ggctgaaaaa gcgaggcctg atgcctgggc tgaccttttc caacgagctg    3240
atttctcgcg acgaaggcct gcactgcgat ttcgcctgtc tgatgtttaa acacctggtg    3300
cataagccct ctgaggaacg agtccgggag atcattatca acgcagtgag gatcgagcag    3360
```

| | |
|---|---|
| gagttcctga cagaagccct gcctgtcaaa ctgattggca tgaattgcac tctgatgaag | 3420 |
| cagtacatcg agtttgtggc cgacaggctg atgctggaac tgggattctc aaaggtgttt | 3480 |
| cgcgtcgaga acccattcga ttttatggag aatatcagcc tggaaggcaa acaaacttc | 3540 |
| tttgagaaga gagtcgggga atatcagagg atgggcgtga tgagcagccc cactgagaat | 3600 |
| agcttcaccc tggacgccga ttttgagct agc | 3633 |

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7 gccacc                                                                    6

<210> SEQ ID NO 8
<211> LENGTH: 2376
<212> TYPE: DNA
<213> ORGANISM: Unknown
<220> FEATURE:
<223> OTHER INFORMATION: Description of Unknown:
Rrm1 sequence

<400> SEQUENCE: 8

| | |
|---|---|
| atgcacgtca tcaagagaga cgggaggcag gaaagagtca tgttcgataa aatcacttca | 60 |
| agaatccaga aactgtgtta cgggctgaac atggacttcg tcgatcctgc ccagattacc | 120 |
| atgaaagtga tccagggact gtactctggc gtcaccacag tggagctgga cacactggcc | 180 |
| gctgaaaccg cagccacact gactaccaaa cacccagatt atgcaattct ggctgcacgg | 240 |
| atcgccgtga gtaatctgca taaggagaca agaaagtct tctcagacgt gatggaggac | 300 |
| ctgtacaatt atatcaaccc tcacaatggg aaacattcac caatggtcgc taagagcact | 360 |
| ctggacattg tgctggccaa caaagatcgg ctgaacagcg ctatcatcta cgaccgggat | 420 |
| ttcagttaca actacttcgg ctttaagaca ctggagagat catatctgct gaaaatcaat | 480 |
| gggaaggtgg ccgaacggcc tcagcacatg ctgatgagag tcagcgtggg cattcataag | 540 |
| gaggacattg atgccgctat cgaaacttac aacctgctga gcgagcgctg gttcacccac | 600 |
| gcttccccta cactgtttaa cgcaggaacc aatcgaccac agctgagcag ctgcttcctg | 660 |
| ctgagcatga aggacgattc catcgagggc atctacgaca ccctgaaaca gtgcgcactg | 720 |
| atttctaaga gtgccggcgg gatcggagtc gctgtgagtt gtattcgggc aaccggctca | 780 |
| tatatcgccg gcacaaacgg caacagcaac gggctggtcc ccatgctgag ggtgtacaac | 840 |
| aatacagccc gctatgtgga tcagggaggc aacaagagac caggagcatt tgccatctac | 900 |
| ctggaacccct ggcacctgga cattttcgag tttctggatc tgaagaaaaa tactggcaaa | 960 |
| gaggaacaga gggctcgcga cctgttcttt gcactgtgga ttcccgacct gttcatgaag | 1020 |
| agggtggaga ccaaccagga ctggagcctg atgtgcccca atgagtgtcc tgggctggat | 1080 |
| gaagtgtggg gagaggaatt tgaaaaactg tacgccagtt atgagaagca gggccgagtg | 1140 |
| cggaaagtgg tcaaggccca gcagctgtgg tacgctatca ttgagagcca gacagaaact | 1200 |
| ggcacccct acatgctgta taagactct tgcaaccgca agagtaacca gcagaatctg | 1260 |
| gggaccatca aatgcagcaa tctgtgtaca gagattgtgg aatatacttc caaggatgag | 1320 |
| gtcgccgtgt gtaacctggc atcactggcc ctgaatatgt acgtcacaag cgagcacact | 1380 |

```
tatgacttca agaaactggc tgaagtgacc aaagtggtcg tgaggaatct gaacaagatc    1440
attgacatca actactatcc cgtgcctgag gcctgcctga gcaataagag acataggccc    1500
atcgggattg gagtgcaggg cctggctgac gcattcatcc tgatgcgcta ccctttttgag   1560 tccgccgaag ctcagctgct gaacaagcag attttttgaaa caatctacta cggggctctg   1620
gaggcatctt gtgacctggc caaagaacag ggaccctacg agacttatga aggctcccct   1680
gtgtctaagg gcatcctgca gtacgatatg tggaacgtca caccaactga cctgtgggat    1740
tggaaagtgc tgaaggagaa aattgcaaag tatggcatcc ggaacagcct gctgatcgcc    1800
ccaatgccca ctgcctctac cgctcagatt ctgggcaaca atgagtccat cgaaccatac    1860
acttctaaca tctacacccg gagagtcctg agcggggagt tccagatcgt gaatccccac    1920
ctgctgaaag acctgaccga acggggactg tggcatgagg aaatgaagaa ccagatcatt    1980
gcctgcaatg gcagtatcca gtcaattcct gagatcccag acgatctgaa acagctgtac    2040
aagacagtct gggagatcag ccagaaaact gtgctgaaga tggcagccga agaggggct    2100 ttcattgatc agtcacagag cctgaacatc cacattgccg agcccaatta cggaaagctg    2160
acctccatgc atttttatgg gtggaaacag ggactgaaga ctggcatgta ctatctgcgc    2220
acccgaccag ctgcaaaccc catccagttt accctgaata aggagaaact gaaggacaaa    2280
gaaaaggtgt ccaaagagga agaggaaaag gagagaaaca cagccgctat ggtgtgttct    2340
ctggagaata gggatgaatg cctgatgtgt ggcagt                              2376

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gctactaact tcagcctgct gaagcaggct ggagacgtgg aggagaaccc tggacct       57

<210> SEQ ID NO 10
<211> LENGTH: 9
<212> TYPE: DNA
<213> ORGANISM: Homo sapiens

<400> SEQUENCE: 10 aaggagaac                                                             9

<210> SEQ ID NO 11
<211> LENGTH: 3
<212> TYPE: DNA
<213> ORGANISM: Homo sapiens

<400> SEQUENCE: 11 acg                                                                   3

<210> SEQ ID NO 12
<211> LENGTH: 9
<212> TYPE: DNA
<213> ORGANISM: Homo sapiens

<400> SEQUENCE: 12 aggaggatc                                                             9
```

<210> SEQ ID NO 13
<211> LENGTH: 3
<212> TYPE: PRT
<213> ORGANISM: Homo sapiens

<400> SEQUENCE: 13

Lys Glu Asn
1

<210> SEQ ID NO 14
<211> LENGTH: 1
<212> TYPE: PRT
<213> ORGANISM: Homo sapiens

<400> SEQUENCE: 14

Thr
1

<210> SEQ ID NO 15
<211> LENGTH: 3
<212> TYPE: PRT
<213> ORGANISM: Homo sapiens

<400> SEQUENCE: 15

Arg Arg Ile
1

<210> SEQ ID NO 16
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgctgagtc tgagggtccc actggcacct atcaccgatc cacagcagct gcagctgagc      60
ccactgaaag gcctgagtct ggtcgatgca gcggccacac cacctgcact gagtggcact     120
cgggtgctgg catcaaagac cgcccggaga attttccagg agccaaccga acccaaaaca     180
aaggccgctg cacctggggt cgaggacgaa ccactgctga gagaatccc aggcgcttc      240 gtgattttc ctatcgaata ccacgatatt tggcagatgt ataagaaagc tgaggcaagt     300
ttctggacag ctgaggaagt ggacctgagc aaagacatcc agcactggga tccctgaag     360 ccagaggaaa ggtacttcat ttctcatgtg ctggcattct tgccgctag tgacgggatc     420 gtgaacgaga atctggtcga acgctttagc caggaggtgc agatcactga gcccgatgc     480 ttctatggat ttcagattgc tatggagaac atccattcag aaatgtacag cctgctgatt     540
gacacctata tcaaagatcc taaggagcgc gagttcctgt taatgccat gagacaatg     600 ccatgtgtga agaaaaaggc agactgggct ctgcgatgga tcggcgataa ggaggctact     660 tacgggaaa gagtggtcgc attcgcagcc gtggaggaa ttttcttttc tggcagtttc     720
gcttccatct tttggctgaa aaagcgaggc ctgatgcctg gctgacctt tccaacgag      780 ctgatttctc gcgacgaagg cctgcactgc gatttcgcct gtctgatgtt taaacacctg     840
gtgcataagc cctctgagga acgagtccgg agatcatta tcaacgcagt gaggatcgag     900
caggagttcc tgacagaagc cctgcctgtc aaactgattg gcatgaattg cactctgatg     960
aagcagtaca tcgagtttgt ggccgacagg ctgatgctgg aactgggatt ctcaaaggtg    1020
tttcgcgtcg agaacccatt cgattttatg gagaatatca gcctggaagg caaaacaaac    1080

```
ttctttgaga agagagtcgg ggaatatcag aggatgggcg tgatgagcag ccccactgag    1140
aatagcttca ccctggacgc cgattttga                                     1170
```

<210> SEQ ID NO 17
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atgctgagtc tgagggtccc actggcacct atcaccgatc cacagcagct gcagctgagc     60
ccactgaaag gcctgagtct ggtcgatgca gcgaacacac cacctgcact gagtggcact    120
cgggtgctgg catcaaagac cgcccggaga attttccagg agccaaccga acccaaaaca    180
aaggccgctg cacctggggt cgaggacgaa ccactgctga gagagaatcc caggcgcttc    240 gtgattttc ctatcgaata ccacgatatt tggcagatgt ataagaaagc tgaggcaagt    300
ttctggacag ctgaggaagt ggacctgagc aaagacatcc agcactggga atccctgaag    360
ccagaggaaa ggtacttcat ttctcatgtg ctggcattct ttgccgctag tgacgggatc    420
gtgaacgaga atctggtcga acgctttagc caggaggtgc agatcactga gcccgatgc    480 ttctatggat ttcagattgc tatggagaac atccattcag aaatgtacag cctgctgatt    540
gacacctata tcaaagatcc taaggagcgc gagttcctgt taatgccat tgagacaatg    600 ccatgtgtga agaaaaaggc agactgggct ctgcgatgga tcggcgataa ggaggctact    660 tacgggaaa gagtggtcgc attcgcagcc gtggagggaa ttttcttttc tggcagtttc    720
gcttccatct tttggctgaa aaagcgaggc ctgatgcctg gctgacctt ttccaacgag    780 ctgatttctc gcgacgaagg cctgcactgc gatttcgcct gtctgatgtt taaacacctg    840
gtgcataagc cctctgagga acgagtccgg gagatcatta tcaacgcagt gaggatcgag    900
caggagttcc tgacagaagc cctgcctgtc aaactgattg gcatgaattg cactctgatg    960
aagcagtaca tcgagtttgt ggccgacagg ctgatgctgg aactgggatt ctcaaaggtg   1020
tttcgcgtcg agaacccatt cgattttatg agaaatatca gcctggaagg caaaacaaac   1080
ttctttgaga gagagtcgg ggaatatcag aggatgggcg tgatgagcag ccccactgag   1140
aatagcttca ccctggacgc cgattttga                                    1170
```

<210> SEQ ID NO 18
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atgctgagtc tgagggtccc actggcacct atcaccgatc cacagcagct gcagctgagc     60
ccactgaaag gcctgagtct ggtcgataaa gagaacgcac cacctgcact gagtggcact    120
cgggtgctgg catcaaagac cgcccggaga attttccagg agccaaccga acccaaaaca    180
aaggccgctg cacctggggt cgaggacgaa ccactgctga gagagaatcc caggcgcttc    240 gtgattttc ctatcgaata ccacgatatt tggcagatgt ataagaaagc tgaggcaagt    300
ttctggacag ctgaggaagt ggacctgagc aaagacatcc agcactggga atccctgaag    360
ccagaggaaa ggtacttcat ttctcatgtg ctggcattct ttgccgctag tgacgggatc    420
```

```
gtgaacgaga atctggtcga acgctttagc caggaggtgc agatcactga agcccgatgc    480
ttctatggat ttcagattgc tatggagaac atccattcag aaatgtacag cctgctgatt    540
gacacctata tcaaagatcc taaggagcgc gagttcctgt ttaatgccat tgagacaatg    600
ccatgtgtga agaaaaaggc agactgggct ctgcgatgga tcggcgataa ggaggctact    660
tacggggaaa gagtggtcgc attcgcagcc gtggagggaa ttttcttttc tggcagtttc    720
gcttccatct tttggctgaa aaagcgaggc ctgatgcctg ggctgacctt ttccaacgag    780
ctgatttctc gcgacgaagg cctgcactgc gatttcgcct gtctgatgtt taaacacctg    840
gtgcataagc cctctgagga acgagtccgg gagatcatta tcaacgcagt gaggatcgag    900
caggagttcc tgacagaagc cctgcctgtc aaactgattg gcatgaattg cactctgatg    960
aagcagtaca tcgagtttgt ggccgacagg ctgatgctgg aactgggatt ctcaaaggtg   1020
tttcgcgtcg agaacccatt cgattttatg gagaatatca gcctggaagg caaaacaaac   1080
ttctttgaga agagagtcgg ggaatatcag aggatgggcg tgatgagcag ccccactgag   1140
aatagcttca ccctggacgc cgatttttga                                    1170

<210> SEQ ID NO 19
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgctgagtc tgagggtccc actggcacct atcaccgatc cacagcagct gcagctgagc     60
ccactgaaag gcctgagtct ggtcgataaa gagaacacac cacctgcact gagtggcact    120
cgggtgctgg catcaaagac cgccgcgaga gctttccagg agccaaccga acccaaaaca    180
aaggccgctg cacctggggt cgaggacgaa ccactgctga gagagaatcc caggcgcttc    240 gtgattttc ctatcgaata ccacgatatt tggcagatgt ataagaaagc tgaggcaagt    300
ttctggacag ctgaggaagt ggacctgagc aaagacatcc agcactggga atccctgaag    360
ccagaggaaa ggtacttcat ttctcatgtg ctggcattct ttgccgctag tgacgggatc    420
gtgaacgaga atctggtcga acgctttagc caggaggtgc agatcactga agcccgatgc    480
ttctatggat ttcagattgc tatggagaac atccattcag aaatgtacag cctgctgatt    540
gacacctata tcaaagatcc taaggagcgc gagttcctgt ttaatgccat tgagacaatg    600
ccatgtgtga agaaaaaggc agactgggct ctgcgatgga tcggcgataa ggaggctact    660
tacggggaaa gagtggtcgc attcgcagcc gtggagggaa ttttcttttc tggcagtttc    720
gcttccatct tttggctgaa aaagcgaggc ctgatgcctg ggctgacctt ttccaacgag    780
ctgatttctc gcgacgaagg cctgcactgc gatttcgcct gtctgatgtt taaacacctg    840
gtgcataagc cctctgagga acgagtccgg gagatcatta tcaacgcagt gaggatcgag    900
caggagttcc tgacagaagc cctgcctgtc aaactgattg gcatgaattg cactctgatg    960
aagcagtaca tcgagtttgt ggccgacagg ctgatgctgg aactgggatt ctcaaaggtg   1020
tttcgcgtcg agaacccatt cgattttatg gagaatatca gcctggaagg caaaacaaac   1080
ttctttgaga agagagtcgg ggaatatcag aggatgggcg tgatgagcag ccccactgag   1140
aatagcttca ccctggacgc cgatttttga                                    1170
```

<210> SEQ ID NO 20
<211> LENGTH: 1170
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
atgctgagtc tgagggtccc actggcacct atcaccgatc cacagcagct gcagctgagc      60
ccactgaaag gcctgagtct ggtcgatgca gcggccacac cacctgcact gagtggcact     120
cgggtgctgg catcaaagac cgccgcgaga gctttccagg agccaaccga acccaaaaca     180
aaggccgctg cacctggggt cgaggacgaa ccactgctga gagaatcc caggcgcttc       240
gtgattttc ctatcgaata ccacgatatt tggcagatgt ataagaaagc tgaggcaagt      300
ttctggacag ctgaggaagt ggacctgagc aaagacatcc agcactggga atccctgaag     360
ccagaggaaa ggtacttcat ttctcatgtg ctggcattct tgccgctag tgacgggatc      420
gtgaacgaga atctggtcga acgctttagc caggaggtgc agatcactga gcccgatgc      480
ttctatggat tcagattgc tatggagaac atccattcag aaatgtacag cctgctgatt      540
gacacctata tcaaagatcc taaggagcgc gagttcctgt ttaatgccat tgagacaatg     600
ccatgtgtga agaaaaaggc agactgggct ctgcgatgga tcggcgataa ggaggctact     660
tacgggaaa gagtggtcgc attcgcagcc gtggagggaa ttttctttc tggcagtttc       720
gcttccatct tttggctgaa aaagcgaggc ctgatgcctg gctgacctt tccaacgag       780
ctgatttctc gcgacgaagg cctgcactgc gatttcgcct gtctgatgtt taaacacctg     840
gtgcataagc cctctgagga acgagtccgg gagatcatta tcaacgcagt gaggatcgag     900
caggagttcc tgacagaagc cctgcctgtc aaactgattg gcatgaattg cactctgatg     960
aagcagtaca tcgagtttgt ggccgacagg ctgatgctgg aactgggatt ctcaaaggtg    1020
tttcgcgtcg agaacccatt cgattttatg gagaatatca gcctggaagg caaaacaaac    1080
ttctttgaga agagagtcgg ggaatatcag aggatgggcg tgatgagcag ccccactgag    1140
aatagcttca ccctggacgc cgattttga                                      1170
```

<210> SEQ ID NO 21
<211> LENGTH: 389
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Ala Ala Ala
            20                  25                  30

Thr Pro Pro Ala Leu Ser Gly Thr Arg Val Leu Ala Ser Lys Thr Ala
        35                  40                  45

Arg Arg Ile Phe Gln Glu Pro Thr Glu Pro Lys Thr Lys Ala Ala Ala
    50                  55                  60

Pro Gly Val Glu Asp Glu Pro Leu Leu Arg Glu Asn Pro Arg Arg Phe
65                  70                  75                  80

Val Ile Phe Pro Ile Glu Tyr His Asp Ile Trp Gln Met Tyr Lys Lys
                85                  90                  95
```

```
Ala Glu Ala Ser Phe Trp Thr Ala Glu Val Asp Leu Ser Lys Asp
            100                 105                 110

Ile Gln His Trp Glu Ser Leu Lys Pro Glu Glu Arg Tyr Phe Ile Ser
            115                 120                 125

His Val Leu Ala Phe Phe Ala Ala Ser Asp Gly Ile Val Asn Glu Asn
            130                 135                 140

Leu Val Glu Arg Phe Ser Gln Glu Val Gln Ile Thr Glu Ala Arg Cys
145                 150                 155                 160

Phe Tyr Gly Phe Gln Ile Ala Met Glu Asn Ile His Ser Glu Met Tyr
                    165                 170                 175

Ser Leu Leu Ile Asp Thr Tyr Ile Lys Asp Pro Lys Glu Arg Glu Phe
                180                 185                 190

Leu Phe Asn Ala Ile Glu Thr Met Pro Cys Val Lys Lys Lys Ala Asp
            195                 200                 205

Trp Ala Leu Arg Trp Ile Gly Asp Lys Glu Ala Thr Tyr Gly Glu Arg
210                 215                 220

Val Val Ala Phe Ala Ala Val Glu Gly Ile Phe Phe Ser Gly Ser Phe
225                 230                 235                 240

Ala Ser Ile Phe Trp Leu Lys Lys Arg Gly Leu Met Pro Gly Leu Thr
                245                 250                 255

Phe Ser Asn Glu Leu Ile Ser Arg Asp Glu Gly Leu His Cys Asp Phe
                260                 265                 270

Ala Cys Leu Met Phe Lys His Leu Val His Lys Pro Ser Glu Glu Arg
            275                 280                 285

Val Arg Glu Ile Ile Asn Ala Val Arg Ile Glu Gln Glu Phe Leu
            290                 295                 300

Thr Glu Ala Leu Pro Val Lys Leu Ile Gly Met Asn Cys Thr Leu Met
305                 310                 315                 320

Lys Gln Tyr Ile Glu Phe Val Ala Asp Arg Leu Met Leu Glu Leu Gly
                325                 330                 335

Phe Ser Lys Val Phe Arg Val Glu Asn Pro Phe Asp Phe Met Glu Asn
                340                 345                 350

Ile Ser Leu Glu Gly Lys Thr Asn Phe Phe Glu Lys Arg Val Gly Glu
            355                 360                 365

Tyr Gln Arg Met Gly Val Met Ser Ser Pro Thr Glu Asn Ser Phe Thr
370                 375                 380

Leu Asp Ala Asp Phe
385

<210> SEQ ID NO 22
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Ala Ala Asn
            20                  25                  30

Thr Pro Pro Ala Leu Ser Gly Thr Arg Val Leu Ala Ser Lys Thr Ala
            35                  40                  45

Arg Arg Ile Phe Gln Glu Pro Thr Glu Pro Lys Thr Lys Ala Ala Ala
50                  55                  60
```

Pro Gly Val Glu Asp Glu Pro Leu Leu Arg Glu Asn Pro Arg Arg Phe
 65                  70                  75                  80

Val Ile Phe Pro Ile Glu Tyr His Asp Ile Trp Gln Met Tyr Lys Lys
                 85                  90                  95

Ala Glu Ala Ser Phe Trp Thr Ala Glu Glu Val Asp Leu Ser Lys Asp
            100                 105                 110

Ile Gln His Trp Glu Ser Leu Lys Pro Glu Glu Arg Tyr Phe Ile Ser
        115                 120                 125

His Val Leu Ala Phe Phe Ala Ala Ser Asp Gly Ile Val Asn Glu Asn
    130                 135                 140

Leu Val Glu Arg Phe Ser Gln Glu Val Gln Ile Thr Glu Ala Arg Cys
145                 150                 155                 160

Phe Tyr Gly Phe Gln Ile Ala Met Glu Asn Ile His Ser Glu Met Tyr
                165                 170                 175

Ser Leu Leu Ile Asp Thr Tyr Ile Lys Asp Pro Lys Glu Arg Glu Phe
            180                 185                 190

Leu Phe Asn Ala Ile Glu Thr Met Pro Cys Val Lys Lys Lys Ala Asp
        195                 200                 205

Trp Ala Leu Arg Trp Ile Gly Asp Lys Glu Ala Thr Tyr Gly Glu Arg
    210                 215                 220

Val Val Ala Phe Ala Ala Val Glu Gly Ile Phe Phe Ser Gly Ser Phe
225                 230                 235                 240

Ala Ser Ile Phe Trp Leu Lys Lys Arg Gly Leu Met Pro Gly Leu Thr
                245                 250                 255

Phe Ser Asn Glu Leu Ile Ser Arg Asp Glu Gly Leu His Cys Asp Phe
            260                 265                 270

Ala Cys Leu Met Phe Lys His Leu Val His Lys Pro Ser Glu Glu Arg
        275                 280                 285

Val Arg Glu Ile Ile Ile Asn Ala Val Arg Ile Glu Gln Glu Phe Leu
    290                 295                 300

Thr Glu Ala Leu Pro Val Lys Leu Ile Gly Met Asn Cys Thr Leu Met
305                 310                 315                 320

Lys Gln Tyr Ile Glu Phe Val Ala Asp Arg Leu Met Leu Glu Leu Gly
                325                 330                 335

Phe Ser Lys Val Phe Arg Val Glu Asn Pro Phe Asp Phe Met Glu Asn
            340                 345                 350

Ile Ser Leu Glu Gly Lys Thr Asn Phe Phe Glu Lys Arg Val Gly Glu
        355                 360                 365

Tyr Gln Arg Met Gly Val Met Ser Ser Pro Thr Glu Asn Ser Phe Thr
    370                 375                 380

Leu Asp Ala Asp Phe
385

<210> SEQ ID NO 23
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Lys Glu Asn

```
                20              25              30
Ala Pro Pro Ala Leu Ser Gly Thr Arg Val Leu Ala Ser Lys Thr Ala
            35              40              45
Arg Arg Ile Phe Gln Glu Pro Thr Glu Pro Lys Thr Lys Ala Ala Ala
        50              55              60
Pro Gly Val Glu Asp Glu Pro Leu Leu Arg Glu Asn Pro Arg Arg Phe
65              70              75              80
Val Ile Phe Pro Ile Glu Tyr His Asp Ile Trp Gln Met Tyr Lys Lys
                85              90              95
Ala Glu Ala Ser Phe Trp Thr Ala Glu Val Asp Leu Ser Lys Asp
            100             105             110
Ile Gln His Trp Glu Ser Leu Lys Pro Glu Glu Arg Tyr Phe Ile Ser
            115             120             125
His Val Leu Ala Phe Phe Ala Ala Ser Asp Gly Ile Val Asn Glu Asn
        130             135             140
Leu Val Glu Arg Phe Ser Gln Glu Val Gln Ile Thr Glu Ala Arg Cys
145             150             155             160
Phe Tyr Gly Phe Gln Ile Ala Met Glu Asn Ile His Ser Glu Met Tyr
                165             170             175
Ser Leu Leu Ile Asp Thr Tyr Ile Lys Asp Pro Lys Glu Arg Glu Phe
            180             185             190
Leu Phe Asn Ala Ile Glu Thr Met Pro Cys Val Lys Lys Lys Ala Asp
        195             200             205
Trp Ala Leu Arg Trp Ile Gly Asp Lys Glu Ala Thr Tyr Gly Glu Arg
    210             215             220
Val Val Ala Phe Ala Ala Val Glu Gly Ile Phe Phe Ser Gly Ser Phe
225             230             235             240
Ala Ser Ile Phe Trp Leu Lys Lys Arg Gly Leu Met Pro Gly Leu Thr
                245             250             255
Phe Ser Asn Glu Leu Ile Ser Arg Asp Glu Gly Leu His Cys Asp Phe
            260             265             270
Ala Cys Leu Met Phe Lys His Leu Val His Lys Pro Ser Glu Glu Arg
        275             280             285
Val Arg Glu Ile Ile Ile Asn Ala Val Arg Ile Glu Gln Glu Phe Leu
    290             295             300
Thr Glu Ala Leu Pro Val Lys Leu Ile Gly Met Asn Cys Thr Leu Met
305             310             315             320
Lys Gln Tyr Ile Glu Phe Val Ala Asp Arg Leu Met Leu Glu Leu Gly
                325             330             335
Phe Ser Lys Val Phe Arg Val Glu Asn Pro Phe Asp Phe Met Glu Asn
            340             345             350
Ile Ser Leu Glu Gly Lys Thr Asn Phe Glu Lys Arg Val Gly Glu
        355             360             365
Tyr Gln Arg Met Gly Val Met Ser Ser Pro Thr Glu Asn Ser Phe Thr
    370             375             380
Leu Asp Ala Asp Phe
385

<210> SEQ ID NO 24
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 24

```
Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Lys Glu Asn
            20                  25                  30

Thr Pro Pro Ala Leu Ser Gly Thr Arg Val Leu Ala Ser Lys Thr Ala
        35                  40                  45

Ala Arg Ala Phe Gln Glu Pro Thr Glu Pro Lys Thr Lys Ala Ala Ala
    50                  55                  60

Pro Gly Val Glu Asp Glu Pro Leu Leu Arg Glu Asn Pro Arg Arg Phe
65                  70                  75                  80

Val Ile Phe Pro Ile Glu Tyr His Asp Ile Trp Gln Met Tyr Lys Lys
                85                  90                  95

Ala Glu Ala Ser Phe Trp Thr Ala Glu Val Asp Leu Ser Lys Asp
            100                 105                 110

Ile Gln His Trp Glu Ser Leu Lys Pro Glu Glu Arg Tyr Phe Ile Ser
            115                 120                 125

His Val Leu Ala Phe Phe Ala Ala Ser Asp Gly Ile Val Asn Glu Asn
130                 135                 140

Leu Val Glu Arg Phe Ser Gln Glu Val Gln Ile Thr Glu Ala Arg Cys
145                 150                 155                 160

Phe Tyr Gly Phe Gln Ile Ala Met Glu Asn Ile His Ser Glu Met Tyr
                165                 170                 175

Ser Leu Leu Ile Asp Thr Tyr Ile Lys Asp Pro Lys Gly Arg Glu Phe
            180                 185                 190

Leu Phe Asn Ala Ile Glu Thr Met Pro Cys Val Lys Lys Lys Ala Asp
            195                 200                 205

Trp Ala Leu Arg Trp Ile Gly Asp Lys Glu Ala Thr Tyr Gly Glu Arg
210                 215                 220

Val Val Ala Phe Ala Ala Val Glu Gly Ile Phe Phe Ser Gly Ser Phe
225                 230                 235                 240

Ala Ser Ile Phe Trp Leu Lys Lys Arg Gly Leu Met Pro Gly Leu Thr
                245                 250                 255

Phe Ser Asn Glu Leu Ile Ser Arg Asp Glu Gly Leu His Cys Asp Phe
            260                 265                 270

Ala Cys Leu Met Phe Lys His Leu Val His Lys Pro Ser Glu Glu Arg
            275                 280                 285

Val Arg Glu Ile Ile Asn Ala Val Arg Ile Glu Gln Glu Phe Leu
290                 295                 300

Thr Glu Ala Leu Pro Val Lys Leu Ile Gly Met Asn Cys Thr Leu Met
305                 310                 315                 320

Lys Gln Tyr Ile Glu Phe Val Ala Asp Arg Leu Met Leu Glu Leu Gly
                325                 330                 335

Phe Ser Lys Val Phe Arg Val Glu Asn Pro Phe Asp Phe Met Glu Asn
            340                 345                 350

Ile Ser Leu Glu Gly Lys Thr Asn Phe Phe Glu Lys Arg Val Gly Glu
            355                 360                 365

Tyr Gln Arg Met Gly Val Met Ser Ser Pro Thr Glu Asn Ser Phe Thr
            370                 375                 380

Leu Asp Ala Asp Phe
385
```

-continued

```
<210> SEQ ID NO 25
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Leu Ser Leu Arg Val Pro Leu Ala Pro Ile Thr Asp Pro Gln Gln
1               5                   10                  15

Leu Gln Leu Ser Pro Leu Lys Gly Leu Ser Leu Val Asp Ala Ala Ala
            20                  25                  30

Thr Pro Pro Ala Leu Ser Gly Thr Arg Val Leu Ala Ser Lys Thr Ala
        35                  40                  45

Ala Arg Ala Phe Gln Glu Pro Thr Glu Pro Lys Thr Lys Ala Ala Ala
    50                  55                  60

Pro Gly Val Glu Asp Glu Pro Leu Leu Arg Glu Asn Pro Arg Arg Phe
65                  70                  75                  80

Val Ile Phe Pro Ile Glu Tyr His Asp Ile Trp Gln Met Tyr Lys Lys
                85                  90                  95

Ala Glu Ala Ser Phe Trp Thr Ala Glu Glu Val Asp Leu Ser Lys Asp
            100                 105                 110

Ile Gln His Trp Glu Ser Leu Lys Pro Glu Glu Arg Tyr Phe Ile Ser
        115                 120                 125

His Val Leu Ala Phe Phe Ala Ala Ser Asp Gly Ile Val Asn Glu Asn
    130                 135                 140

Leu Val Glu Arg Phe Ser Gln Glu Val Gln Ile Thr Glu Ala Arg Cys
145                 150                 155                 160

Phe Tyr Gly Phe Gln Ile Ala Met Glu Asn Ile His Ser Glu Met Tyr
                165                 170                 175

Ser Leu Leu Ile Asp Thr Tyr Ile Lys Asp Pro Lys Glu Arg Glu Phe
            180                 185                 190

Leu Phe Asn Ala Ile Glu Thr Met Pro Cys Val Lys Lys Lys Ala Asp
        195                 200                 205

Trp Ala Leu Arg Trp Ile Gly Asp Lys Glu Ala Thr Tyr Gly Glu Arg
    210                 215                 220

Val Val Ala Phe Ala Ala Val Glu Gly Ile Phe Phe Ser Gly Ser Phe
225                 230                 235                 240

Ala Ser Ile Phe Trp Leu Lys Lys Arg Gly Leu Met Pro Gly Leu Thr
                245                 250                 255

Phe Ser Asn Glu Leu Ile Ser Arg Asp Glu Gly Leu His Cys Asp Phe
            260                 265                 270

Ala Cys Leu Met Phe Lys His Leu Val His Lys Pro Ser Glu Glu Arg
        275                 280                 285

Val Arg Glu Ile Ile Ile Asn Ala Val Arg Ile Glu Gln Glu Phe Leu
    290                 295                 300

Thr Glu Ala Leu Pro Val Lys Leu Ile Gly Met Asn Cys Thr Leu Met
305                 310                 315                 320

Lys Gln Tyr Ile Glu Phe Val Ala Asp Arg Leu Met Leu Glu Leu Gly
                325                 330                 335

Phe Ser Lys Val Phe Arg Val Glu Asn Pro Phe Asp Phe Met Glu Asn
            340                 345                 350

Ile Ser Leu Glu Gly Lys Thr Asn Phe Phe Glu Lys Arg Val Gly Glu
        355                 360                 365
```

```
Tyr Gln Arg Met Gly Val Met Ser Ser Pro Thr Glu Asn Ser Phe Thr
        370                 375                 380

Leu Asp Ala Asp Phe
385

<210> SEQ ID NO 26
<211> LENGTH: 76
<212> TYPE: DNA
<213> ORGANISM: Homo sapiens

<400> SEQUENCE: 26
ctggaaaatt ctccgggcgg tctttgatgc cagcacccga gtgccactca gtgcaggtgg    60
tgtgttctct ttatcg                                                   76

<210> SEQ ID NO 27
<211> LENGTH: 25
<212> TYPE: PRT
<213> ORGANISM: Homo sapiens

<400> SEQUENCE: 27

Asp Lys Glu Asn Thr Pro Pro Ala Leu Ser Gly Thr Arg Val Leu Ala
1               5                   10                  15

Ser Lys Thr Ala Arg Arg Ile Phe Gln
            20                  25

<210> SEQ ID NO 28
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctggaaaatt ctccgggcgg tctttgatgc cagcacccga gtgccactca gtgcaggtgg    60
tgtggccgct gcatcg                                                   76

<210> SEQ ID NO 29
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctggaaaatt ctccgggcgg tctttgatgc cagcacccga gtgccactca gtgcaggtgg    60
tgtgttcgct gcatcg                                                   76

<210> SEQ ID NO 30
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctggaaaatt ctccgggcgg tctttgatgc cagcacccga gtgccactca gtgcaggtgg    60
tgcgttctct ttatcg                                                   76

<210> SEQ ID NO 31
```

```
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctggaaagct ctcgcggcgg tctttgatgc cagcacccga gtgccactca gtgcaggtgg      60
tgtgttctct ttatcg                                                     76

<210> SEQ ID NO 32
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctggaaagct ctcgcggcgg tctttgatgc cagcacccga gtgccactca gtgcaggtgg      60
tgtggccgct gcatcg                                                     76
```